(12) United States Patent
Willard

(10) Patent No.: US 6,258,060 B1
(45) Date of Patent: Jul. 10, 2001

(54) URETHRAL APPARATUS WITH POSITION INDICATOR AND METHODS OF USE THEREOF

(75) Inventor: Lloyd K. Willard, Miltona, MN (US)

(73) Assignee: AbbeyMoon Medical, Inc., Miltona, MN (US)

( * ) Notice: Subject to any disclaimer, the term of this patent is extended or adjusted under 35 U.S.C. 154(b) by 0 days.

(21) Appl. No.: 09/340,491

(22) Filed: Jun. 30, 1999

Related U.S. Application Data

(62) Division of application No. 08/993,818, filed on Dec. 18, 1997, now Pat. No. 5,964,732.
(60) Provisional application No. 60/036,944, filed on Feb. 7, 1997.

(51) Int. Cl.[7] .............................. A61M 5/00; A61N 1/00; A61F 6/06

(52) U.S. Cl. .......................... 604/117; 604/517; 128/840; 607/138; 607/143
(58) Field of Search ................................. 604/57, 66, 117, 604/50, 514, 93, 100, 907, 515, 517; 128/839, 841; 623/24, 26; 600/377, 423, 424, 29–31; 607/138, 143

(56) References Cited

U.S. PATENT DOCUMENTS

| | | |
|---|---|---|
| 207,932 | 9/1878 | Alvord . |
| 547,047 | 10/1895 | Thornton et al. . |
| 707,775 | 8/1902 | Harris . |
| 1,045,326 | 11/1912 | Ruflin . |
| 1,589,056 | 6/1926 | Drummond . |
| 1,644,919 | 10/1927 | Hayes . |
| 1,688,795 | 10/1928 | Aas . |
| 1,714,741 | 5/1929 | Urquhart . |

(List continued on next page.)

FOREIGN PATENT DOCUMENTS

| | | |
|---|---|---|
| 268 055 | 5/1989 | (DE) . |
| 0 753 289 A1 | 1/1997 | (EP) . |
| 564832 | 1/1924 | (FR) . |
| 2 219 941 | 12/1989 | (GB) . |
| 2 219 943 | 12/1989 | (GB) . |
| WO 95/17862 | 7/1995 | (WO) . |
| WO 97/06758 | 2/1997 | (WO) . |
| WO 97/25090 | 7/1997 | (WO) . |
| WO 98/06354 | 2/1998 | (WO) . |

OTHER PUBLICATIONS

Hayes, O., M.D., "Spiral Urethral Dilator," *Jour. A. M. A.,* Sep. 18, 1926, vol. 87, No. 12, pp. 939–940.

Pending AbbeyMoor patent application No.: 09/411,491, Inventor: Willard., Filing Date: Oct. 4, 1999.

*Primary Examiner*—Sharon Kennedy
(74) *Attorney, Agent, or Firm*—Brinks Hofer Gilson & Lione

(57) ABSTRACT

An apparatus and method for placement of a tubular body in the urethra. The tubular body includes a proximal portion adapted for placement toward a bladder end and bladder neck end of the urethra and a distal portion opposite from the proximal portion. A sensor component located on the tubular body is responsive to a feature of the urethra and outputs a first signal indicating proper placement of the proximal portion of the tubular body relative to the bladder and bladder neck. Preferably, an insertion tool is used during positioning of the urethral apparatus. The insertion tool is coupled to the distal end of the urethral apparatus and is used to push the urethral apparatus proximally in the urethra. The first signal can be transmitted from the urethral apparatus through the insertion tool from which it is perceivable by the person positioning the urethral device. Upon proper placement, the insertion tool is decoupled from the urethral apparatus and withdrawn leaving the urethral apparatus in place in the urethra with the proximal portion properly positioned relative to the bladder neck and bladder.

9 Claims, 36 Drawing Sheets

U.S. PATENT DOCUMENTS

| | | | |
|---|---|---|---|
| 2,078,686 | 4/1937 | Rowe . | |
| 2,450,217 | 9/1948 | Alcorn . | |
| 3,136,316 | 6/1964 | Beall . | |
| 3,331,371 | 7/1967 | Rocchi et al. . | |
| 3,419,008 | 12/1968 | Plishner . | |
| 3,428,046 | 2/1969 | Remer et al. . | |
| 3,498,286 | 3/1970 | Polanyi et al. . | |
| 3,503,400 | 3/1970 | Osthagen et al. . | |
| 3,630,206 | 12/1971 | Gingold . | |
| 3,642,004 | 2/1972 | Osthagen et al. . | |
| 3,731,670 | 5/1973 | Loe . | |
| 3,742,958 | 7/1973 | Rundles . | |
| 3,768,102 | 10/1973 | Kwan-Gett et al. . | |
| 3,786,810 | 1/1974 | Pannier, Jr. et al. . | |
| 3,788,327 | 1/1974 | Donowitz et al. . | |
| 3,797,478 | 3/1974 | Walsh et al. . | |
| 3,799,172 | 3/1974 | Szpur . | |
| 3,810,259 * | 5/1974 | Summers | 128/898 |
| 3,812,841 | 5/1974 | Isaacson . | |
| 3,815,608 | 6/1974 | Spinosa et al. . | |
| 3,831,588 | 8/1974 | Rindner . | |
| 3,863,622 | 2/1975 | Buuck . | |
| 3,876,234 | 4/1975 | Harms . | |
| 3,902,501 | 9/1975 | Citron et al. . | |
| 3,924,631 | 12/1975 | Mancusi, Jr. . | |
| 3,939,821 | 2/1976 | Roth . | |
| 3,946,724 | 3/1976 | La Balme . | |
| 4,024,855 | 5/1977 | Bucalo . | |
| 4,249,536 | 2/1981 | Vega . | |
| 4,266,815 | 5/1981 | Cross . | |
| 4,269,192 | 5/1981 | Matsuo . | |
| 4,344,435 | 8/1982 | Aubin . | |
| 4,350,161 | 9/1982 | Davis, Jr. . | |
| 4,356,826 | 11/1982 | Kubota . | |
| 4,432,757 | 2/1984 | Davis, Jr. . | |
| 4,501,580 | 2/1985 | Glassman . | |
| 4,553,533 | 11/1985 | Leighton . | |
| 4,571,749 * | 2/1986 | Fischell | 623/14 |
| 4,579,554 | 4/1986 | Glassman . | |
| 4,670,008 | 6/1987 | Von Albertini . | |
| 4,679,546 | 7/1987 | van Wallwijk van Doorn et al. . | |
| 4,711,249 | 12/1987 | Brooks . | |
| 4,757,194 | 7/1988 | Simms . | |
| 4,760,847 | 8/1988 | Vaillancourt . | |
| 4,795,439 | 1/1989 | Guest . | |
| 4,801,293 | 1/1989 | Jackson . | |
| 4,809,709 | 3/1989 | Brooks . | |
| 4,815,472 | 3/1989 | Wise et al. . | |
| 4,820,288 | 4/1989 | Isono . | |
| 4,822,333 | 4/1989 | Lavarenne . | |
| 4,909,263 | 3/1990 | Norris . | |
| 4,909,785 | 3/1990 | Burton et al. . | |
| 4,919,653 | 4/1990 | Martinez et al. . | |
| 4,934,999 | 6/1990 | Bader . | |
| 4,946,449 | 8/1990 | Davis, Jr. . | |
| 4,955,858 | 9/1990 | Drews . | |
| 4,969,896 | 11/1990 | Shors . | |
| 5,004,454 | 4/1991 | Beyar et al. . | |
| 5,018,529 | 5/1991 | Tenerz et al. . | |
| 5,030,199 | 7/1991 | Barwick et al. . | |
| 5,030,227 | 7/1991 | Rosenbluth et al. . | |
| 5,041,092 | 8/1991 | Barwick . | |
| 5,087,252 | 2/1992 | Denard . | |
| 5,088,980 | 2/1992 | Leighton . | |
| 5,129,910 | 7/1992 | Phan et al. . | |
| 5,140,999 | 8/1992 | Ardito . | |
| 5,159,920 | 11/1992 | Condon et al. . | |
| 5,188,111 | 2/1993 | Yates et al. . | |
| 5,239,982 | 8/1993 | Trauthen . | |
| 5,246,445 | 9/1993 | Yachia et al. . | |
| 5,257,636 | 11/1993 | White . | |
| 5,271,735 | 12/1993 | Greenfeld et al. . | |
| 5,275,169 | 1/1994 | Afromowitz et al. . | |
| 5,279,567 | 1/1994 | Ciaglia et al. . | |
| 5,312,430 | 5/1994 | Rosenbluth et al. . | |
| 5,334,185 | 8/1994 | Giesy et al. . | |
| 5,366,506 | 11/1994 | Davis . | |
| 5,380,268 | 1/1995 | Wheeler . | |
| 5,383,866 | 1/1995 | Chang . | |
| 5,389,077 | 2/1995 | Melinyshyn et al. . | |
| 5,423,809 | 6/1995 | Klicek . | |
| 5,425,382 | 6/1995 | Golden et al. . | |
| 5,427,114 | 6/1995 | Colliver et al. . | |
| 5,437,290 | 8/1995 | Bolger et al. . | |
| 5,437,604 | 8/1995 | Kulisz et al. . | |
| 5,445,144 | 8/1995 | Wodicka et al. . | |
| 5,470,350 | 11/1995 | Buchholtz et al. . | |
| 5,472,405 | 12/1995 | Buchholtz et al. . | |
| 5,476,434 * | 12/1995 | Kalb et al. | 600/30 |
| 5,483,832 | 1/1996 | Pauser et al. . | |
| 5,486,191 | 1/1996 | Pasricha et al. . | |
| 5,492,131 | 2/1996 | Galel . | |
| 5,507,731 | 4/1996 | Hernandez et al. . | |
| 5,509,888 | 4/1996 | Miller . | |
| 5,512,032 | 4/1996 | Kulisz et al. . | |
| 5,514,178 | 5/1996 | Torchio . | |
| 5,520,650 | 5/1996 | Zadini et al. . | |
| 5,520,665 | 5/1996 | Fleetwood . | |
| 5,524,336 | 6/1996 | Rosenbluth et al. . | |
| 5,549,577 | 8/1996 | Siegel et al. . | |
| 5,558,091 | 9/1996 | Acker et al. . | |
| 5,601,537 | 2/1997 | Frassica . | |
| 5,618,257 | 4/1997 | Kulisz et al. . | |
| 5,701,916 | 12/1997 | Kulisz et al. . | |
| 5,704,353 * | 1/1998 | Kalb et al. | 128/634 |
| 5,711,314 | 1/1998 | Ardito . | |
| 5,713,877 | 2/1998 | Davis . | |
| 5,718,686 | 2/1998 | Davis . | |
| 5,722,932 | 3/1998 | Kulisz et al. . | |
| 5,749,826 | 5/1998 | Faulkner . | |
| 5,759,162 * | 6/1998 | Oppelt et al. | 601/2 |
| 5,795,288 | 8/1998 | Cohen et al. . | |
| 5,807,265 * | 9/1998 | Itoigawa et al. | 600/486 |
| 5,876,417 | 3/1999 | Devonec et al. . | |
| 5,954,701 * | 9/1999 | Matalon | 604/272 |
| 5,964,732 | 10/1999 | Willard . | |
| 5,971,967 | 10/1999 | Willard . | |
| 5,984,879 * | 11/1999 | Wallace et al. | 600/587 |
| 6,012,781 * | 2/2000 | Thompson et al. | 128/898 |
| 6,019,728 * | 2/2000 | Iwata et al. | 600/486 |
| 6,019,729 * | 2/2000 | Itoigawa et al. | 600/488 |

* cited by examiner

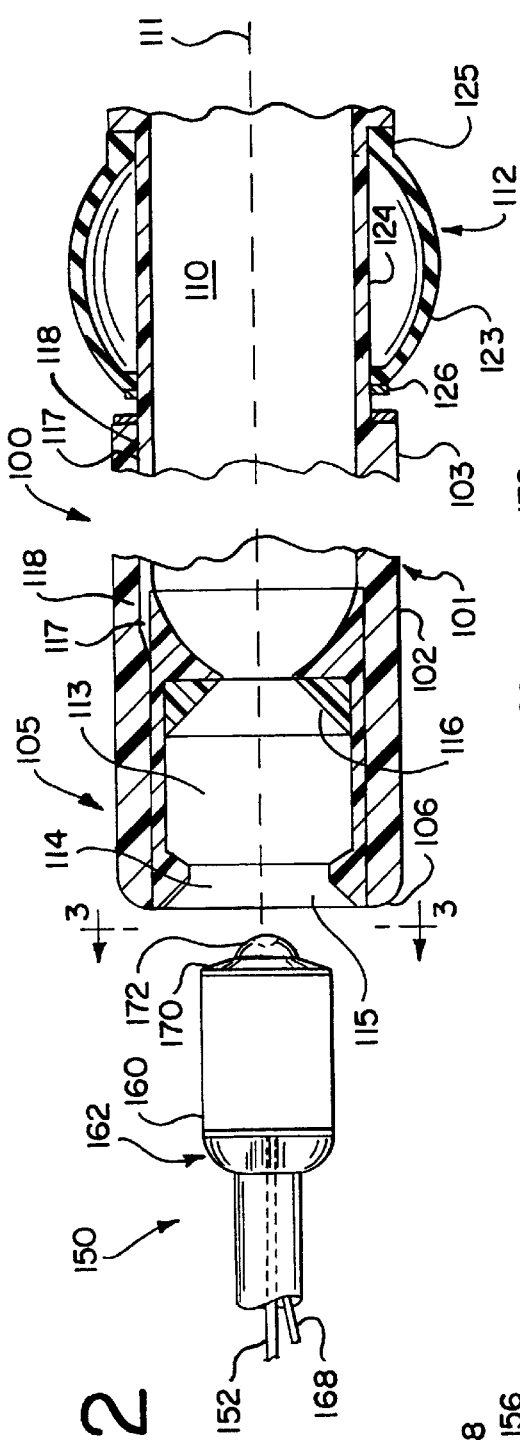

RELEASED POSITION

LOCKED POSITION

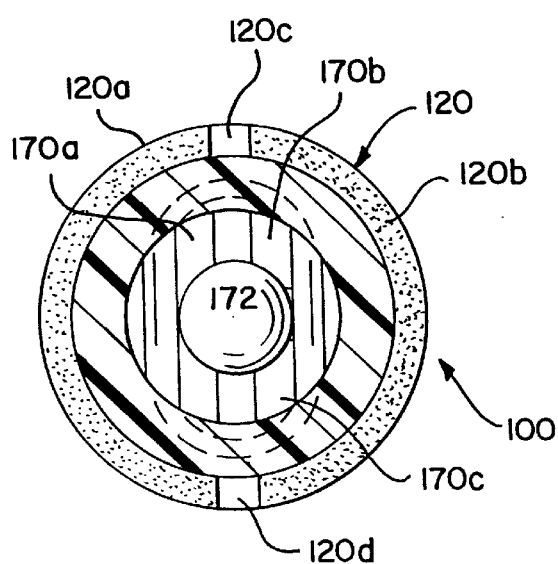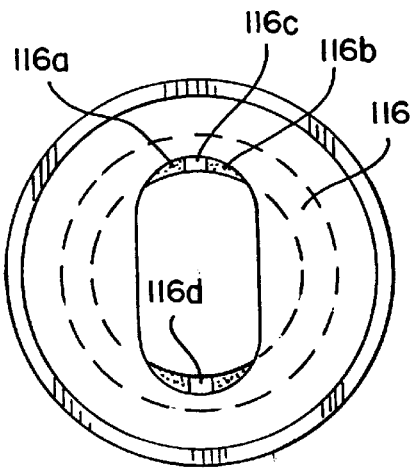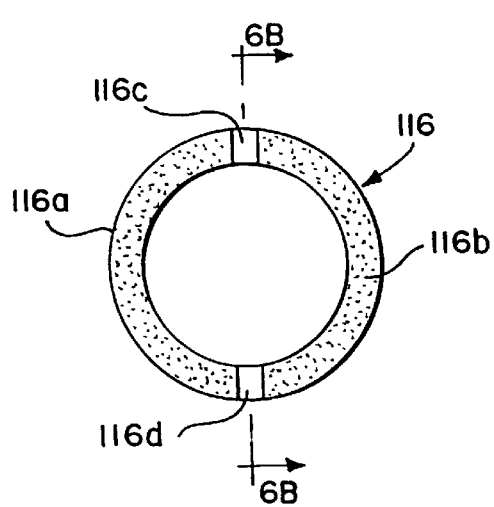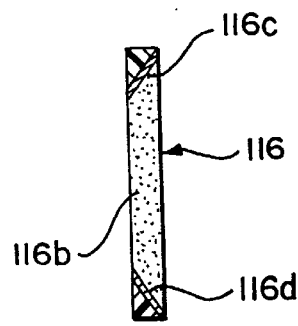

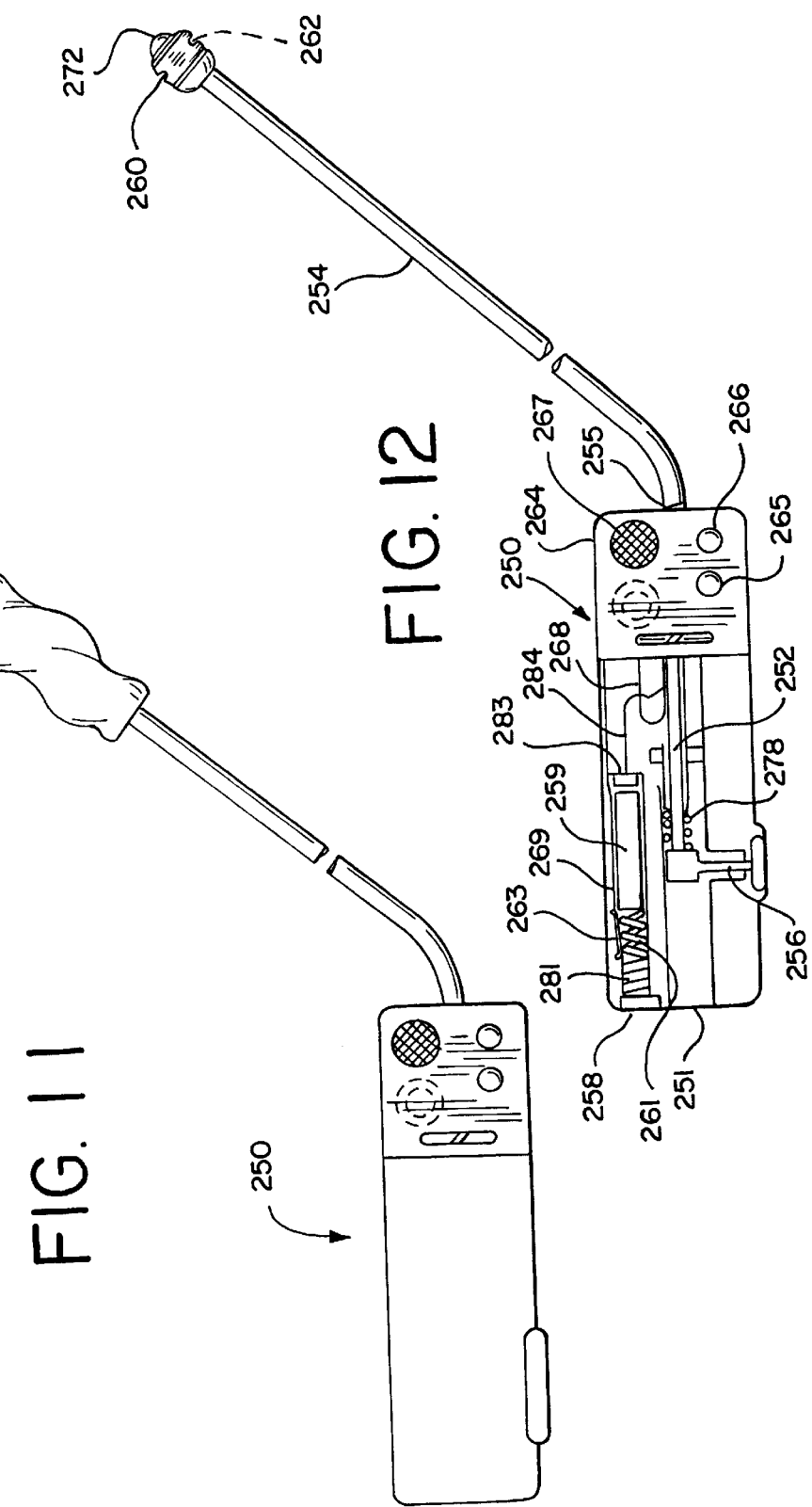

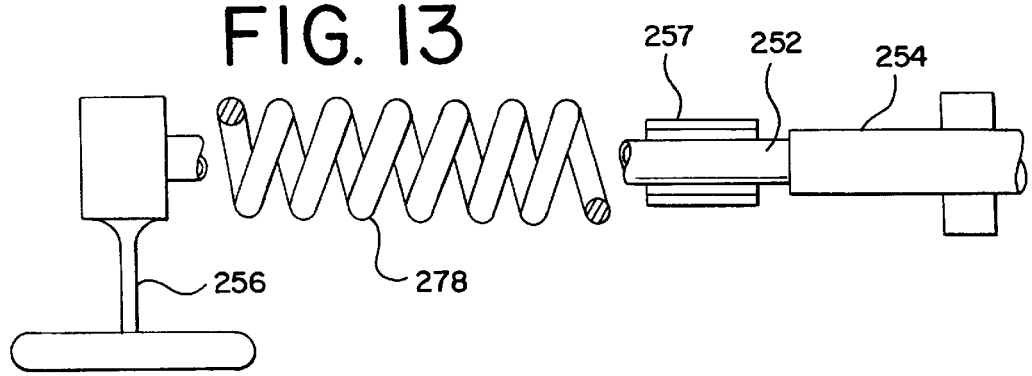
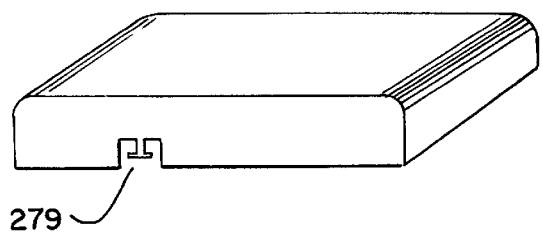
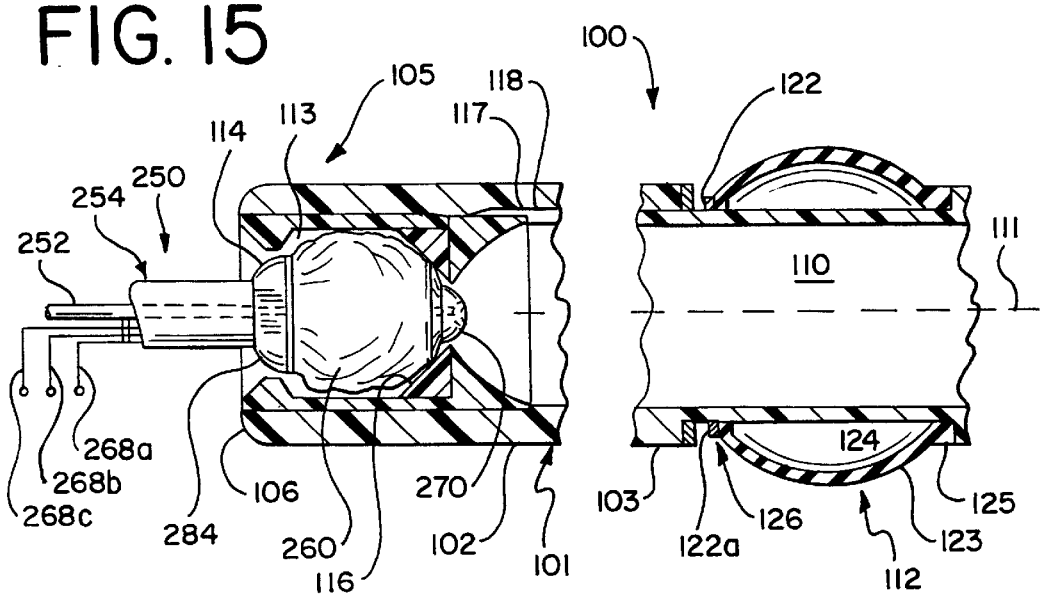

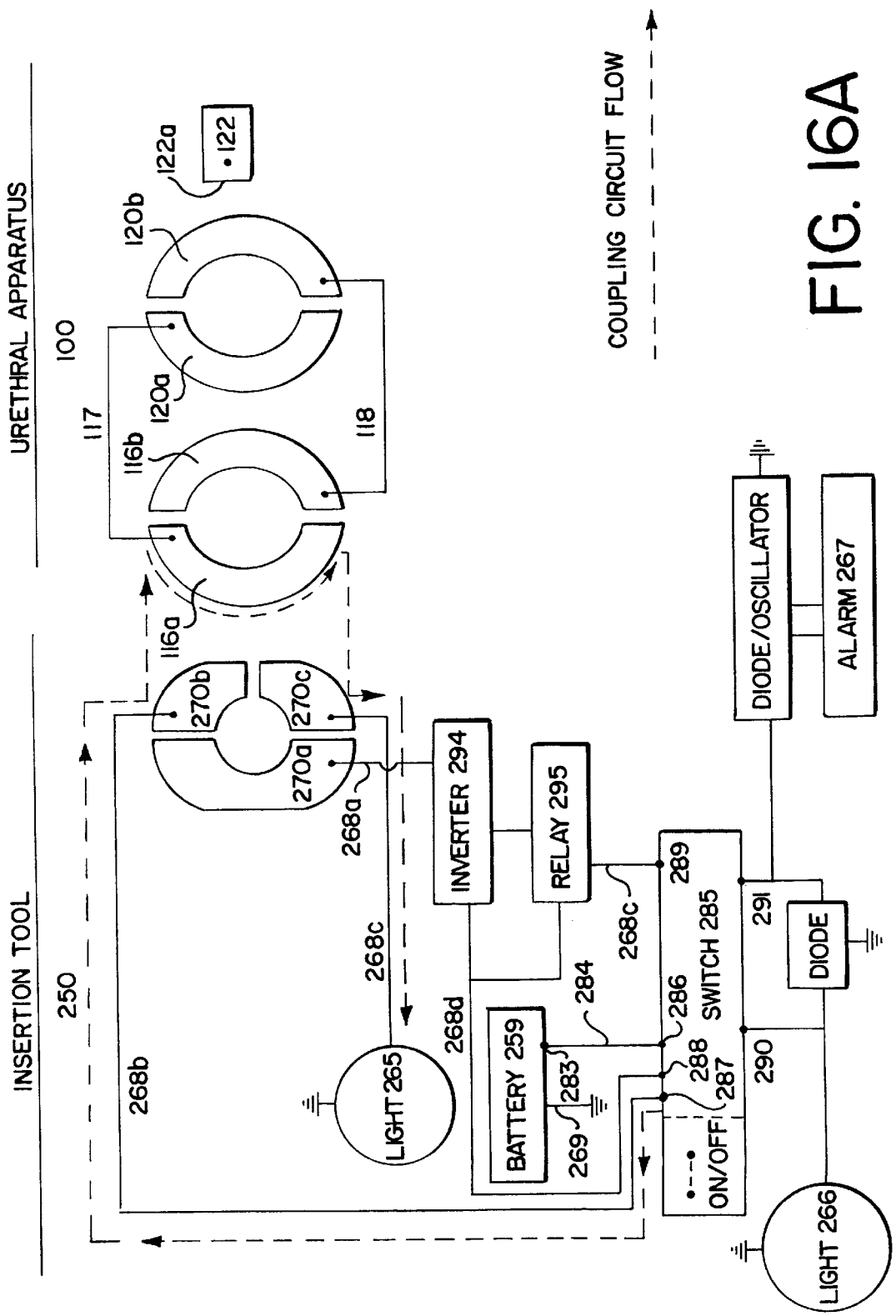

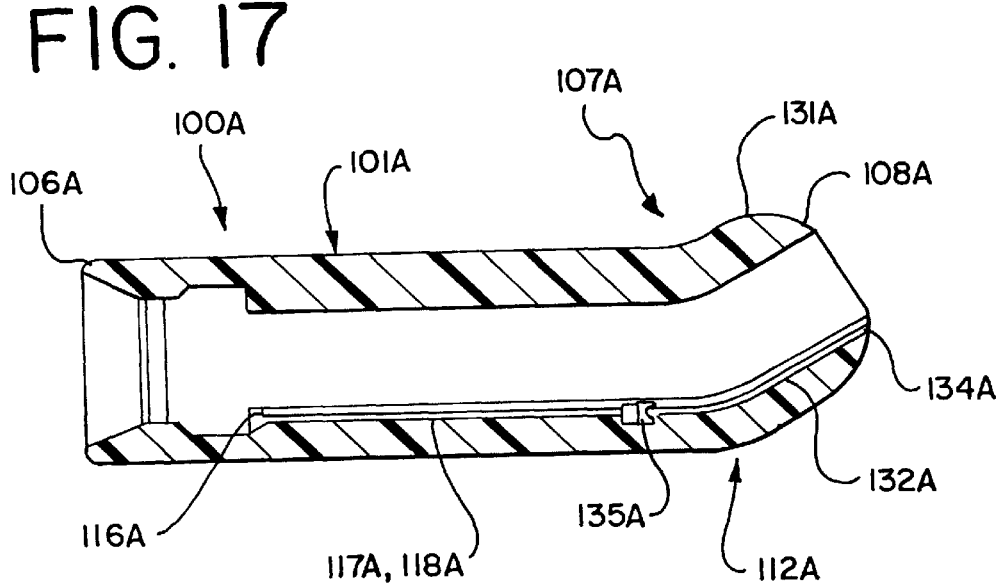
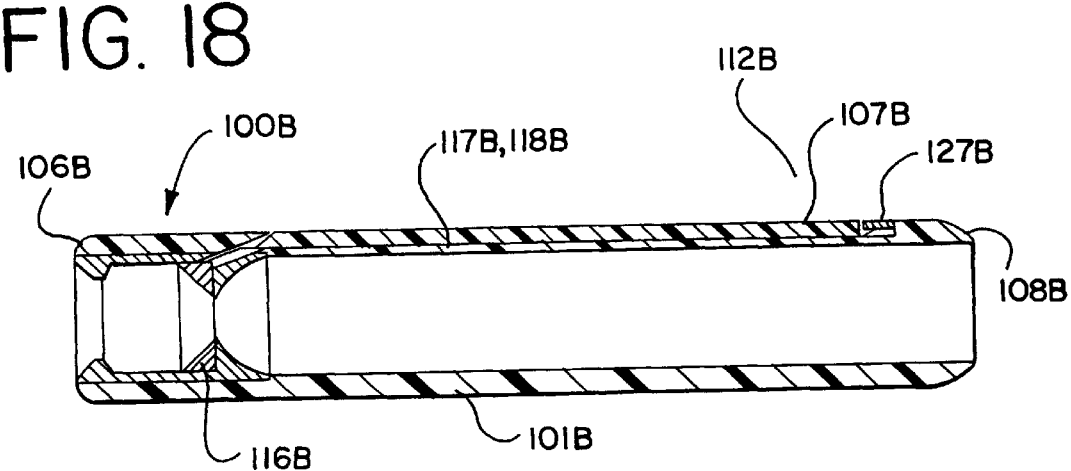
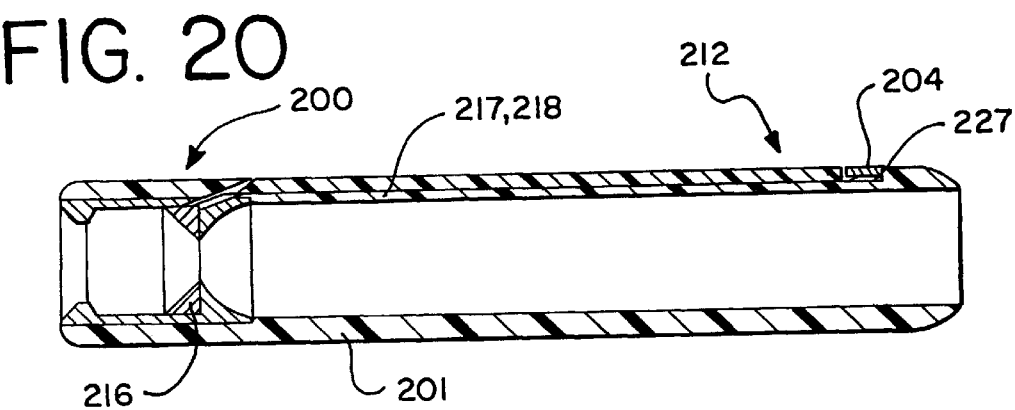

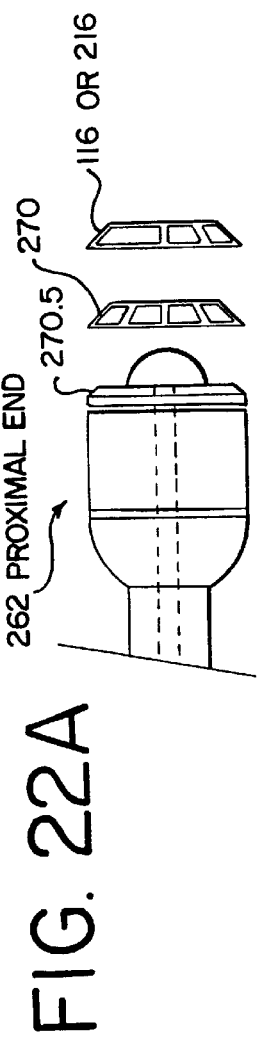
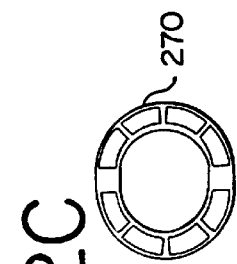
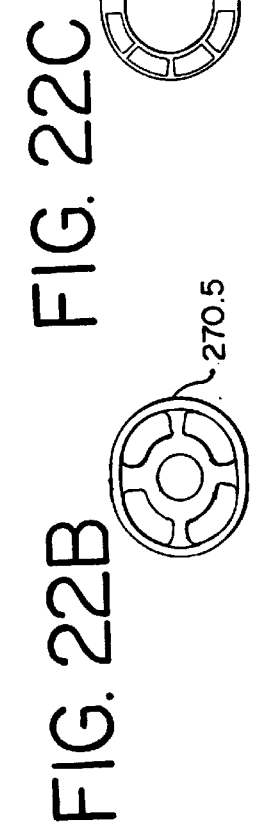
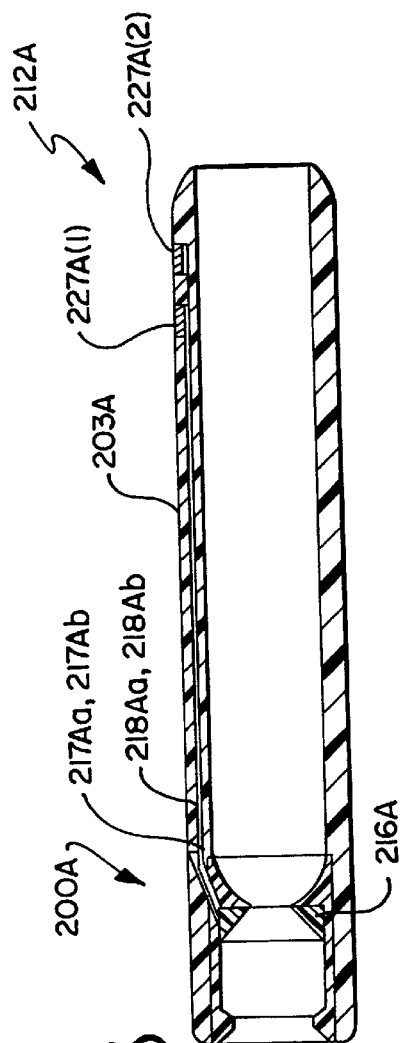

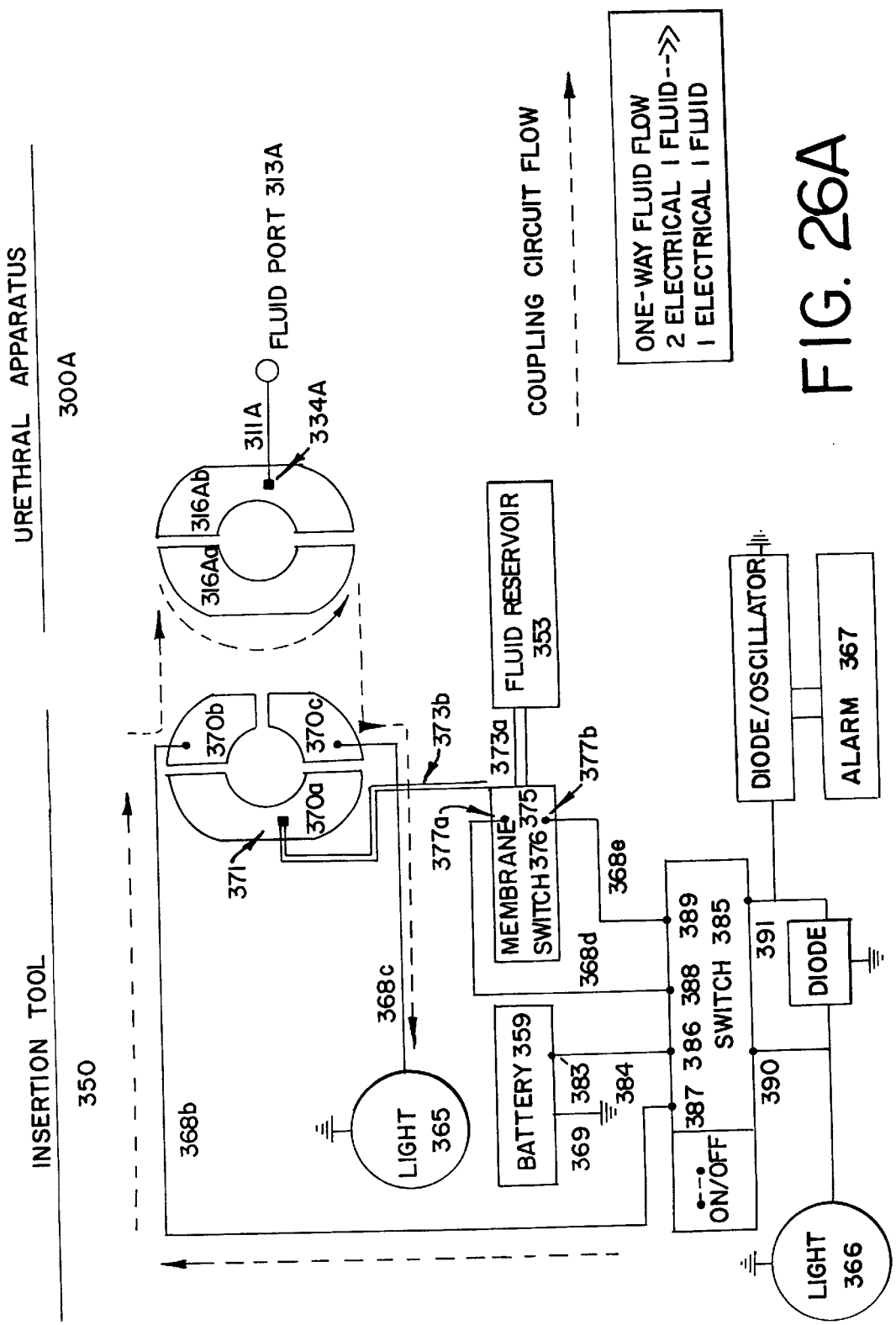

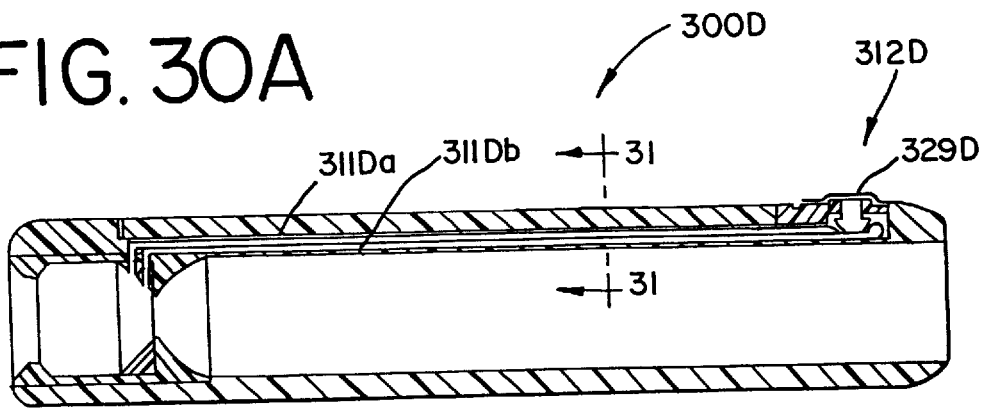
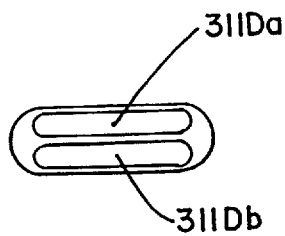 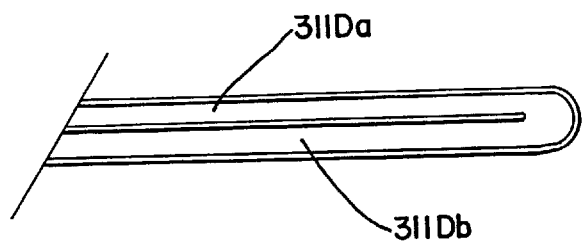
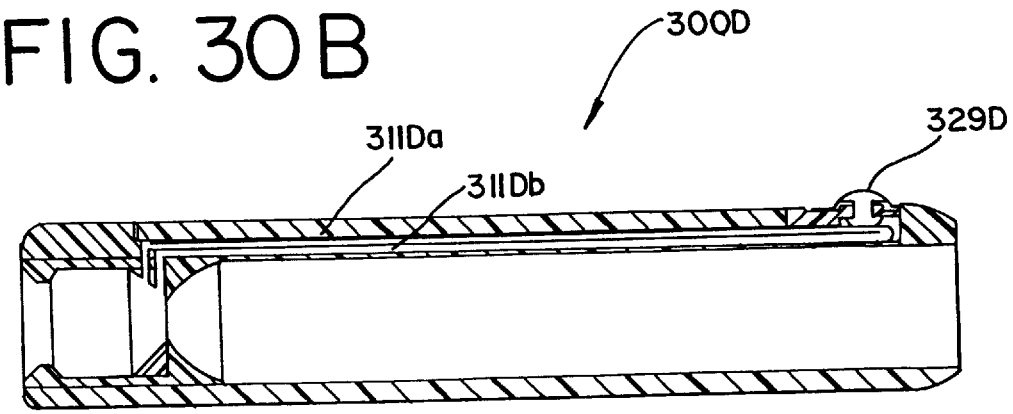

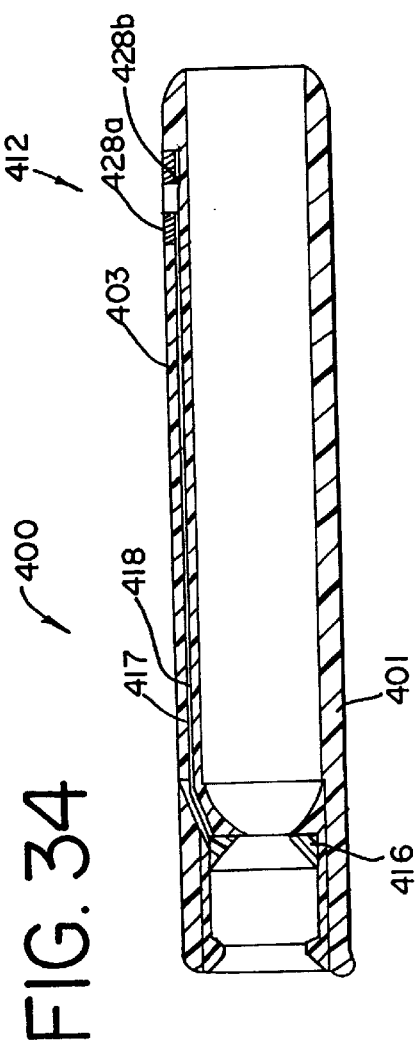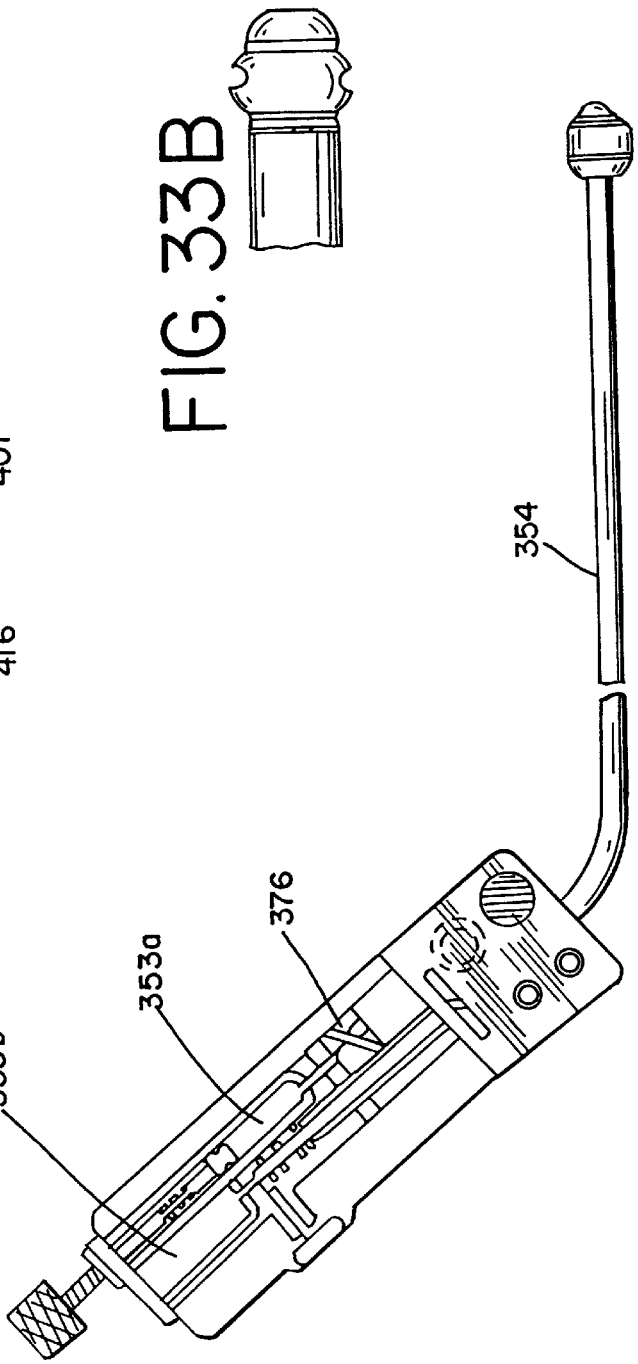

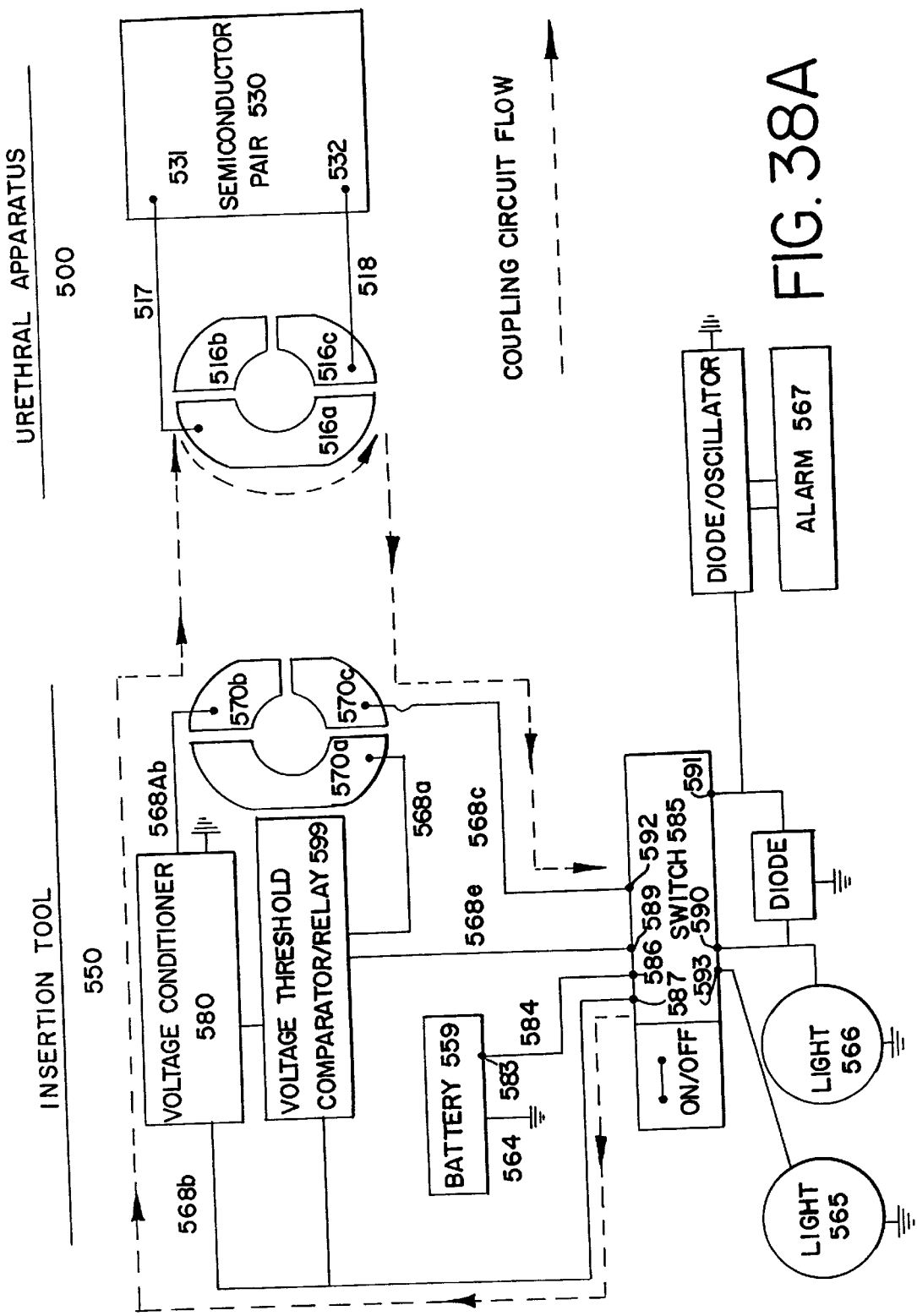

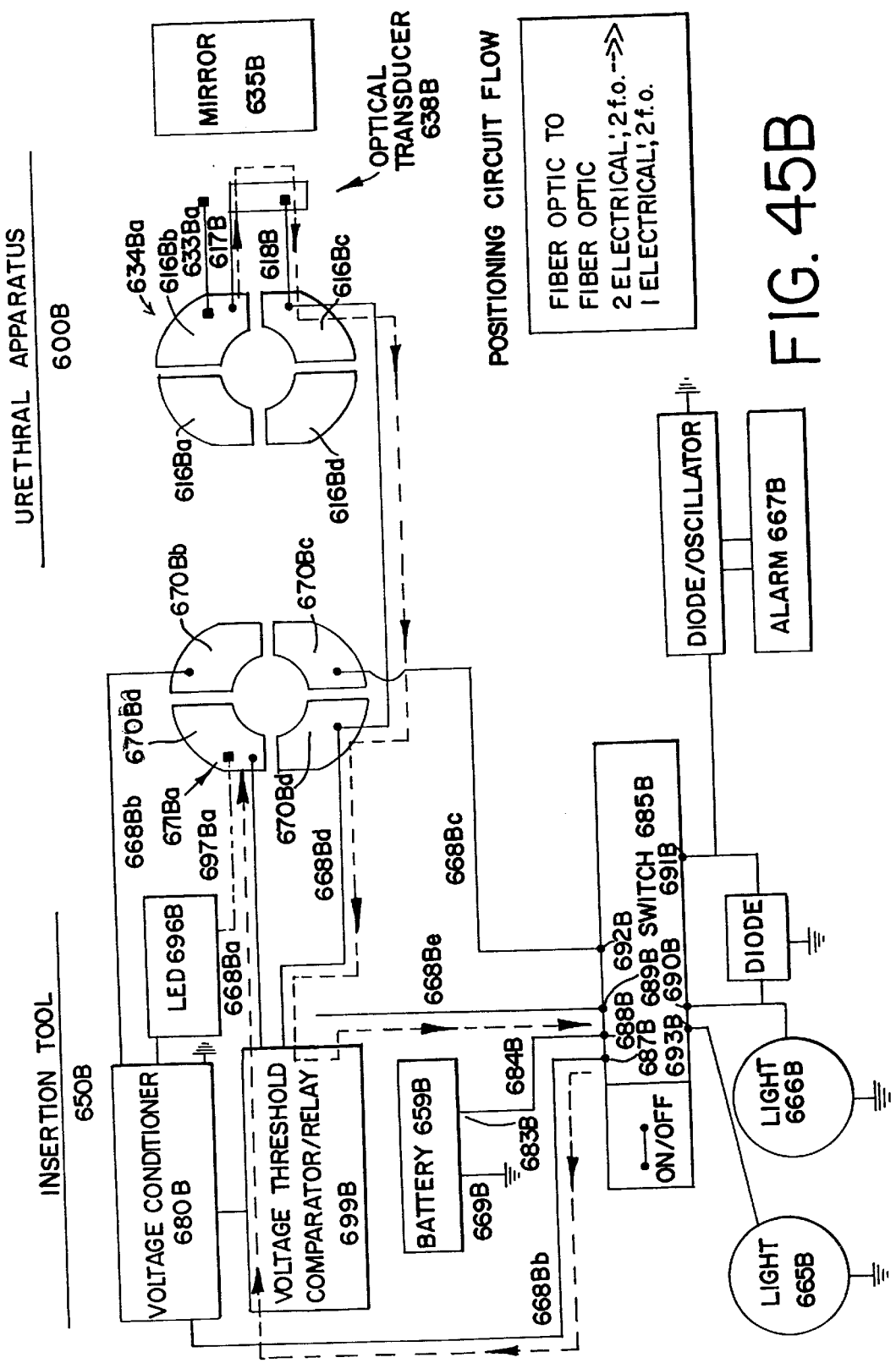

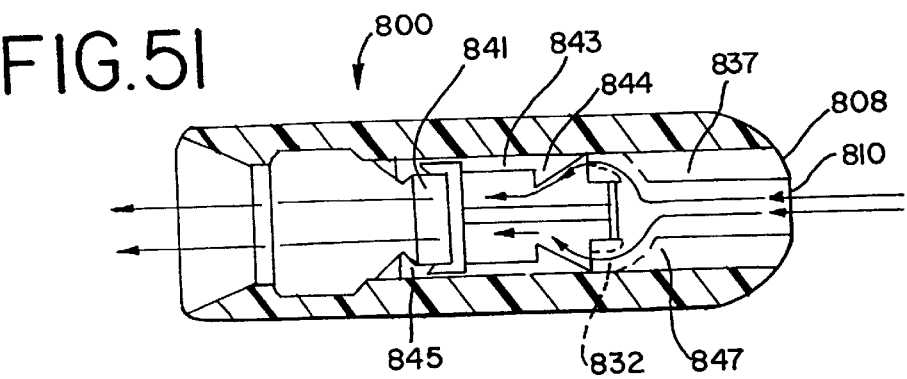
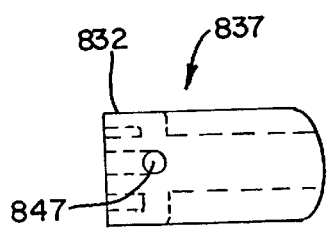 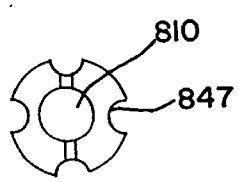
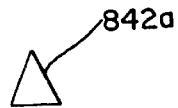 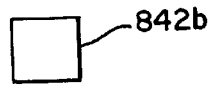
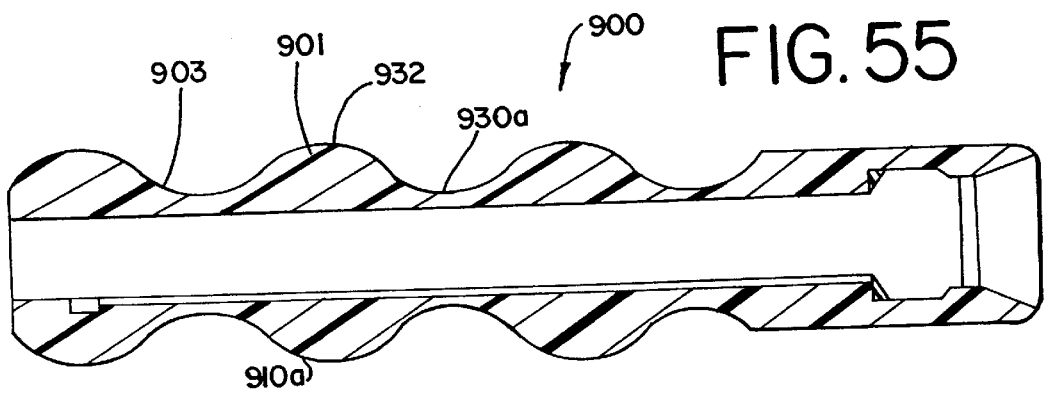

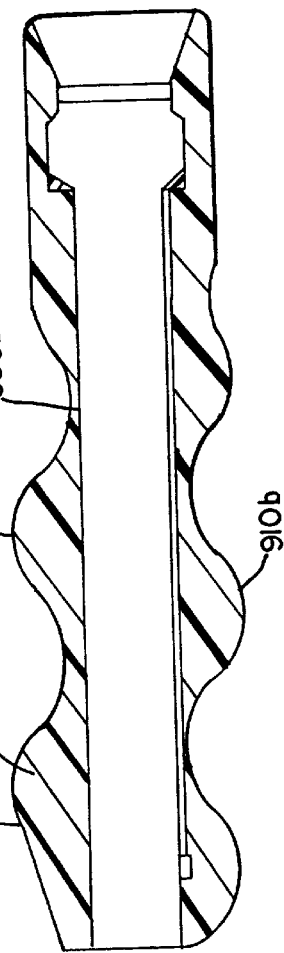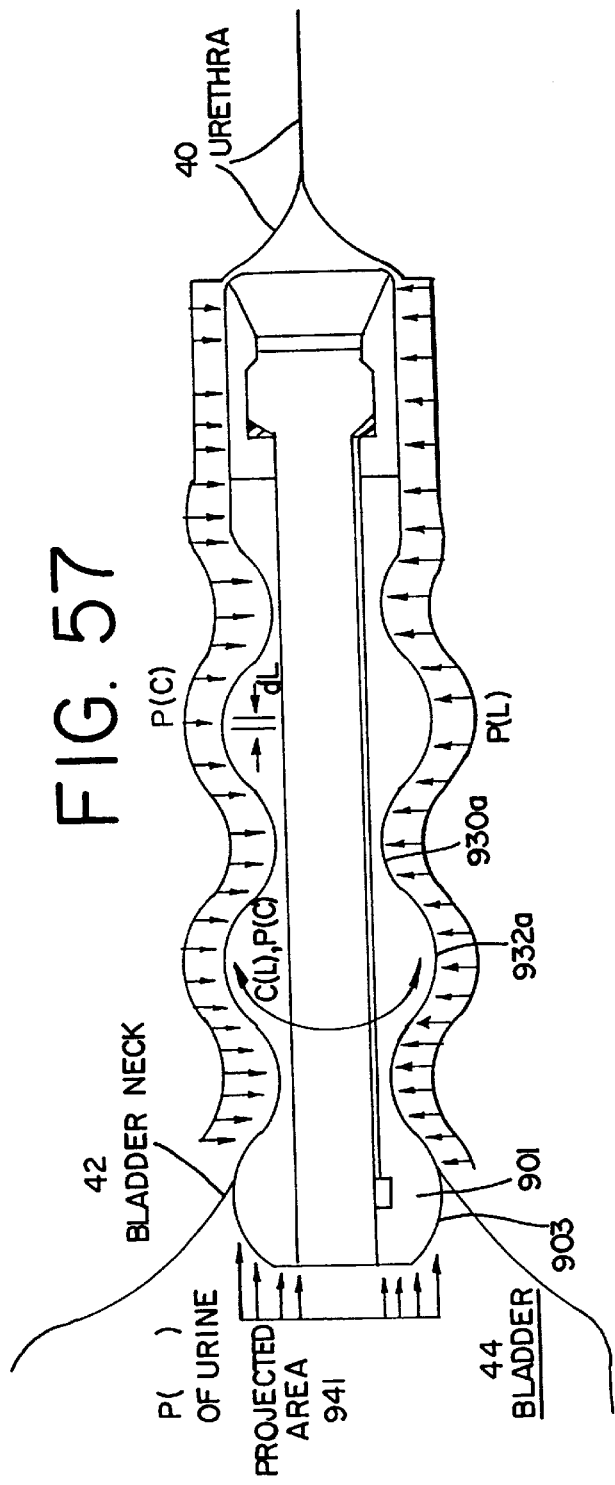
FIG. 56
FIG. 57

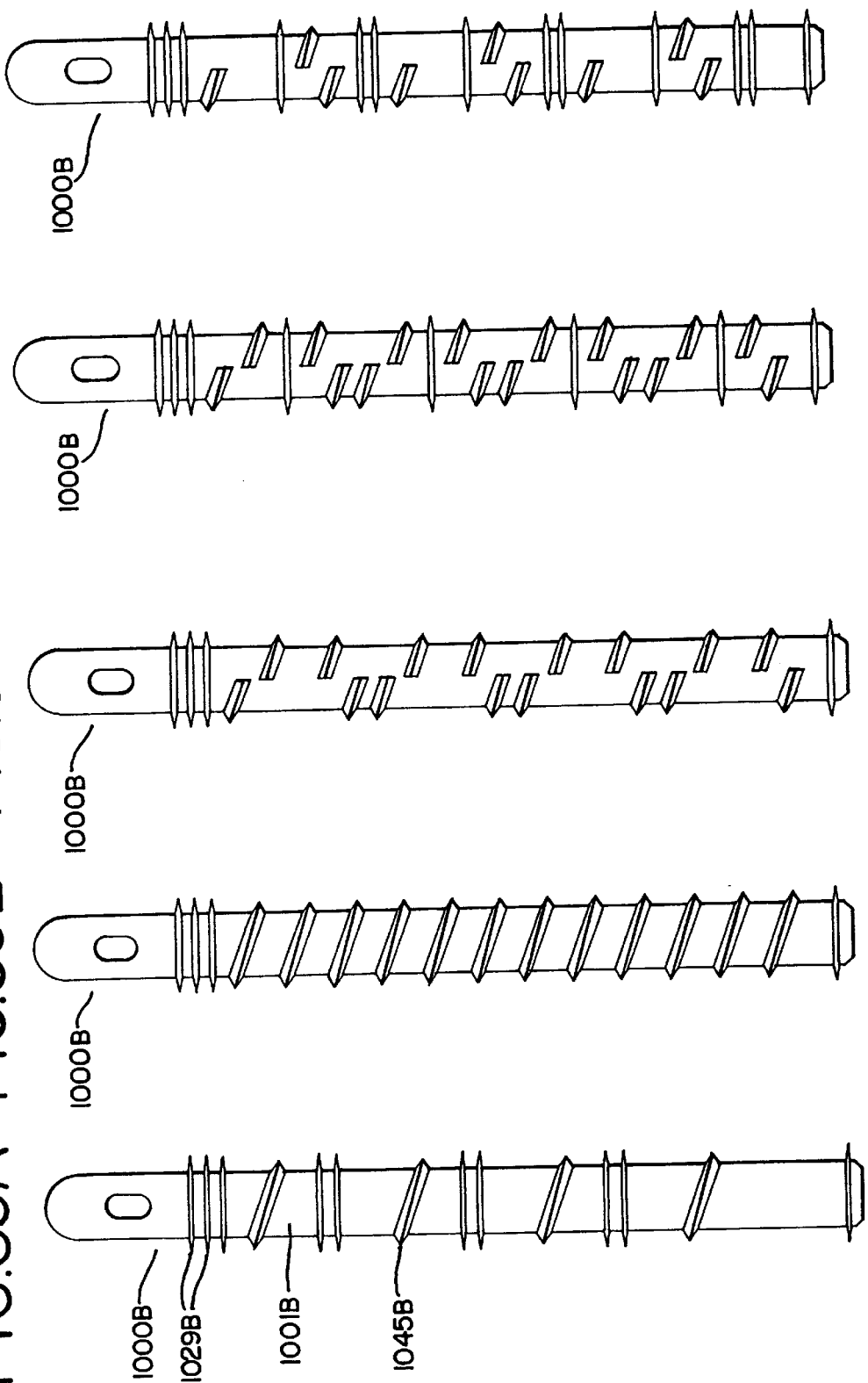

URETHRAL APPARATUS WITH POSITION INDICATOR AND METHODS OF USE THEREOF

REFERENCE TO RELATED APPLICATIONS

This application is a division of U.S. application Ser. No. 08/993,818 U.S. Pat. No. 5,964,732 issued Oct. 12, 1999.

The present application claims priority to U.S. provisional application Ser. No. 60/036,944, filed Feb. 7, 1997, the entire disclosure of which is incorporated herein by reference, U.S. Pat. No. 5,971,967 issued Oct. 26,1999, the entire disclosure of which is incorporated herein by reference, and the U.S. patent application entitled "URETHRAL APPARATUS WITH HIGH FLOW VALVE AND METHODS OF USE THEREOF" filed on even date herewith, the entire disclosure of which is incorporated herein by reference.

FIELD OF THE INVENTION

The present invention relates generally to apparatuses for placement in the urethra and methods of using such apparatuses, and more particularly to apparatuses that can be positioned in the urethra for short-term or long-term use and that provide functions such as valving for flow control or that provide introduction passageways for the placement of diagnostic or therapeutic equipment into the urinary tract.

BACKGROUND OF THE INVENTION

Urine flow problems include urine retention, incontinence, and difficult urination. These problems, especially retention and ischuria, can have serious consequences. Retention can result from any of a number of causes, including without limitation, spinal cord injury or tumors, coma, typhoid, peritonitis, prostatic enlargement, urethral stricture, urethritis, cystitis, bladder tumors, urethral calculus, Parkinson's disease, prostatitis, or multiple sclerosis. Patients suffering from these and other conditions often require some interventional means to periodically drain the bladder. Failure to do so can result in damage of the epithelium and detrusor muscles associated with the bladder, and an increased potential for bacterial invasion and urinary tract infection.

The urine flow problem of incontinence is the inability to retain urine. Incontinence can result from paralysis or relaxation of the sphincters or contraction of the longitudinal muscular layers of the bladder. Incontinence can also occur in coma, epileptic seizure, spinal cord injury or tumors associated with the spinal cord, spinal meningitis, or local irritation of the bladder. Incontinence may be categorized as either stress incontinence, in which urine is expelled during stresses such as exercise, coughing, and laughing; urge incontinence, in which the patient in unable to control the urge to urinate in part due to uninhibited bladder contractions; or mixed incontinence, in which the patient experiences both stress and urge incontinence.

Difficult urination or dysuria can result from urethral strictures, enlarged prostates, atony and impairment of the bladder's muscular power, and inflammatory conditions involving the urethra, bladder, or lower ureter.

Devices have been developed to be positioned in the urethra and/or bladder to correct the problems of urine flow. These devices, including urinary drainage catheters, have been used for many years. A device of this type requires proper placement in the urethra in order to operate correctly and with minimal discomfort. It can be difficult to properly position a urine-control device in the urethra. Some of these urethral devices require that a physician use a cystoscope or rely on ultrasound, fluoroscopy, X-ray, or similar technology for position information to properly place a device in the urethra. These techniques require relatively expensive equipment. Another way that it can be determined that a urethral device has been positioned into the bladder is to observe the flow of urine through the device which is an indication that the bladder has been entered. This method requires that a through-lumen or valve can be maintained in an open position during insertion and that the bladder be sufficiently full so that a flow of fluid is readily observable. Therefore, this method may not be available if the patient's bladder is empty. Accordingly, devices for placement in the urethra are relatively hard to properly position and have often required that a skilled physician position the device using expensive equipment.

Accordingly, it is an object to provide a urethral device that can be positioned relatively easily.

SUMMARY OF THE INVENTION

To address the above concerns, the present invention provides an apparatus and method for placement of a tubular body in the urethra. The tubular body includes a proximal portion adapted for placement in the urethra toward a bladder and bladder neck and a distal portion opposite from the proximal portion. A sensor component located on the tubular body is responsive to a feature of the urethra and outputs a first signal indicating proper placement of the proximal portion of the tubular body relative to the bladder and bladder neck. Preferably, an insertion tool is used during positioning of the urethral apparatus. The insertion tool is coupled to the distal end of the urethral apparatus and is used to push the urethral apparatus proximally in the urethra. The first signal can be transmitted from the urethral apparatus through the insertion tool from which it is perceivable by the person positioning the urethral device. Upon proper placement, the insertion tool is decoupled from the urethral apparatus and withdrawn leaving the urethral apparatus in place in the urethra with the proximal portion properly positioned relative to the bladder neck and bladder.

BRIEF DESCRIPTION OF THE DRAWINGS

In the drawings, in which like reference numerals indicate corresponding parts through the several views;

FIG. 1 shows a side view of a first embodiment of a urethral apparatus and an insertion tool showing the insertion tool partially cutaway.

FIG. 2 is a side sectional view of a distal portion and sensing component of the urethral apparatus of FIG. 1 and a partially cutaway view of a proximal portion of the insertion tool, uncoupled from the urethral apparatus.

FIG. 3 is an end view of the insertion tool of FIG. 2 taken from line 3–3'.

FIG. 5B is a sectional view of the urethral apparatus taken along line 5B–5B' of FIG. 5A.

FIG. 5C is a sectional view of the urethral apparatus taken along line 5C–5C' of FIG. 5A.

FIG. 6A is an end view of the apparatus first contact collar of FIG. 5A.

FIG. 6B is a sectional side view of the apparatus first contact collar of FIG. 5A.

FIG. 11 is a side view of the urethral apparatus of FIG. 1 coupled to an alternate embodiment of an insertion tool.

FIG. 12 is a side view partially in section of the insertion tool of FIG. 11.

FIG. 13 is an exploded view of components of the insertion tool shown in FIG. 12.

FIG. 14 is a side view of the removable cover with the stop component of the insertion tool shown in FIGS. 11–13.

FIG. 15 is a side sectional view of the urethral apparatus of FIG. 1 and a partially cutaway view of a proximal portion of the insertion tool of FIGS. 11–14, coupled to the urethral apparatus.

FIG. 16A is a schematic flow diagram illustrating the electrical flow during coupling of the insertion tool and urethral apparatus of FIG. 15.

FIG. 17 is a sectional view of another embodiment of a urethral apparatus having a preformed portion.

FIG. 18 is a sectional view of still another embodiment of a urethral apparatus, utilizing a piezoelectric transducer or membrane switch.

FIG. 20 is a sectional view of an alternate embodiment of a urethral apparatus, utilizing acoustic sensing.

FIG. 22A is a side view of the proximal end of an embodiment of the insertion tool illustrating the contact collar assembly and its interface with the contact collar of the urethral apparatus.

FIG. 22B is an end view of the contact collar housing of FIG. 22A.

FIG. 22C is an end view of the contact collar of FIG. 22A.

FIG. 22D is an end view of the contact collar housing of the urethral apparatus of FIG. 22A.

FIG. 23 is a sectional view of another alternate embodiment of a urethral apparatus that utilizes acoustic sensing.

FIG. 26A is a schematic flow diagram illustrating the electrical flow during coupling of the insertion tool and urethral apparatus of FIG. 24.

FIG. 26B is a schematic flow diagram illustrating the electrical flow during positioning of the insertion tool and urethral apparatus of FIG. 24.

FIG. 30A is a sectional view of a fourth alternate embodiment of a urethral apparatus that utilizes fluid flow sensing shown in a closed mode.

FIG. 30B is a sectional view of the embodiment of the urethral apparatus shown in FIG. 30A shown in an open mode.

FIG. 31 is an expanded cross sectional view of the fluid passages shown in FIG. 30, taken along lines 31–31'.

FIG. 32 is a close-up sectional view of the proximal portion of the fluid passageways shown in FIGS. 30 and 31.

FIG. 33A is a partially cutaway side view of an insertion tool for use with the embodiment of the urethral apparatus in FIG. 32

FIG. 33B is a close-up view of the proximal portion of the insertion tool of FIG. 33A.

FIG. 34 is a sectional view of an alternate embodiment of a urethral apparatus that uses electrical resistance measurement for position sensing.

FIG. 38A is a schematic flow diagram illustrating the electrical flow during coupling of the insertion tool and urethral apparatus of FIG. 36.

FIG. 45B is a schematic flow diagram illustrating the electrical flow during positioning of the insertion tool and urethral apparatus of FIG. 45A.

FIG. 51 is a sectional view of the embodiment of FIG. 48 showing the fluid flow path.

FIG. 52 is a side view of the fluid flow director of FIG. 48.

FIG. 53 is an end view of the fluid flow director of FIG. 48.

FIG. 54A is an end view of an embodiment of the magnet of FIG. 48.

FIG. 54B is an end view of an alternative embodiment of the magnet of FIG. 54A.

FIG. 55 is a sectional view of an alternate embodiment of a urethral apparatus that includes anchoring features for securing the apparatus in the urethra.

FIG. 56 is a sectional view of an alternate embodiment of a urethral apparatus having anchoring features.

FIG. 57 is a sectional view of the embodiment of FIG. 55 positioned within the urethra with lines illustrating forces applied to the apparatus.

FIGS. 59A, 59B, 59C, 59D, and 59E show alternative embodiments for males of urethral apparatuses having anchoring structures.

DETAILED DESCRIPTION OF THE PRESENTLY PREFERRED EMBODIMENTS

I. General Overview

Figure 4A:
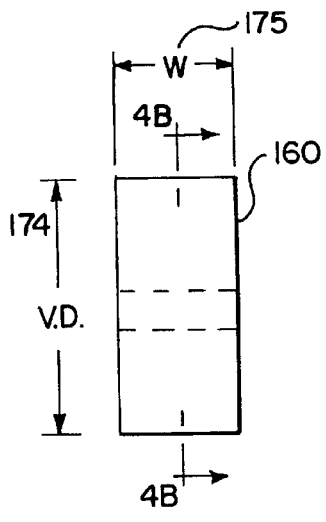
FIG. 4A is a side view of the deformable coupling of FIG. 3 in a released position.

Disclosed below are various embodiments of apparatuses for urethral placement. The disclosed embodiments provide functions that require proper placement of the apparatus in the urethra. For example, in embodiments that are used for control of incontinence, it is required that a proximal part of the apparatus be in or close to the bladder so that urine can flow into an opening in the proximal end of the apparatus. These embodiments described below include a feature that facilitates proper placement of the apparatus.

II. Embodiments with Mechanical Sensing

A. First Embodiment of a Urethral Apparatus

FIGS. 1–10 show a first embodiment of an apparatus 100. The apparatus 100 is intended to be positioned in a urethra (shown in FIGS. 7–10) and to extend partially into a bladder (shown in FIGS. 7 and 9) of a patient. The patient may be either a male or female human, or alternatively, embodiments of the apparatus may be used in other mammals or even in non-mammals, with suitable changes in dimensions.

Referring to FIGS. 1 and 2, the apparatus 100 includes a body 101 having a wall 102 with an exterior surface 103. The body 101 has a generally tubular shape around axis 111. The body 101 has a distal portion 105 terminating in a distal end 106 and a proximal portion 107 terminating in a proximal end 108. (As used herein, the term "proximal" refers to the end which is at or close to the bladder and the term "distal" refers to the end opposite the proximal end and farther away from the bladder when the apparatus is in place. The proximal end would be inserted first. This terminology convention applies as well to the insertion tool, described below.)

The cross sectional shape of the body 101 may be generally circular or may be flattened to conform to the anatomical shape of the urethra. The body 101 has a generally tubular shape around an axis 111. The proximal portion 107 of the body 101 has at least one port 109 which may be located at the proximal portion 107 or proximal end 108 to allow for urine flow into and through the apparatus. Alternately, the proximal end 108 may have an open through-lumen to allow the apparatus to be used as an introducer for fluids, stents, or other apparatuses or to function as a temporary stent itself for diagnostic and therapeutic procedures in the lower or upper urinary tract. The body 101 defines a passageway or lumen 110 that extends through the length of the body 101 from the proximal port 109 to a distal opening 115.

In one embodiment the apparatus 100 is produced using a composite construction of a base tube and cast external features. A base tube is constructed as a braid reinforced silicone tube using a stainless steel wire braid and Shore A 60 durometer silicone compound as the tube polymer (tubing produced by New England Electric Wire Corp. Lisbon, N.H.). The internal diameter of the base tube is 0.160 inches using a braid core diameter of 0.180 inches. The external diameter of the base tube is 0.210 inches.

In one class of embodiments of the urethral apparatus 100, the body 101 has an overall length such that the body 101 resides entirely within the urinary tract of the patient, preferably primarily within the urethra, except to the extent to which the proximal end 108 extends partially or completely into either the bladder or the bladder neck. In these embodiments, the distal end 106 of the body 101 of the apparatus 100 does not extend outside the urethra after it is positioned. In these embodiments that are retained entirely within the patients' bodies, additional elements or capabilities may be provided, such as a fluid valving or drug delivery, as described more fully below. In present embodiments, the body 101 is less than 10 cm in length in versions for adult-sized male users and 5 cm in length for adult-sized female users, but more preferably less than 5 cm in length for female users.

In certain applications, such as certain short-term applications, alternate embodiments of the apparatus 100 can be employed in which the overall length of the body 101 is greater than the above dimensions. In these embodiments, the distal end 106 of the body 101 extends outside the urethra while the proximal end 108 is positioned within the bladder or the bladder neck. In embodiments of the apparatus in which the distal end extends outside the body, the distal end 106 can be connected to a fluid collection or introducer system.

The body 101 may be sized from about 10 French to 34 French to accommodate the large range of urethral sizes from infants to adults. The exterior surface 103 of the body 101 is constructed of molded silicone or alternatively of latex. Alternative materials include molded polyurethane, polyethylene, polycarbonate, or other biocompatible materials.

B. First Embodiment of Insertion Tool.

Referring to FIGS. 1 and 2, the urethral apparatus 100 is releasably coupled with an insertion tool 150 for placement and removal. The insertion tool 150 provides three functions. First, the insertion tool 150 couples to the urethral apparatus 100 and aids insertion of the apparatus 100 into the urethra, bladder neck, or bladder. Second, the insertion tool 150 completes the respective electrical circuits to provide feedback that the urethral apparatus 100 is coupled with the insertion tool 150. Third, the insertion tool 150 interfaces with the urethral apparatus 100 and completes the various electrical, optical, fluid, or mechanical circuits, channels, or linkages of the urethral apparatus 100 to provide feedback to the caregiver that the urethral apparatus 100 is properly positioned in relation to the bladder neck or bladder. These functions of the insertion tool 150 are described below.

Referring to FIGS. 1 and 2, the insertion tool 150 has a handle 151 and a linkage 152 that passes through a shaft 154. The linkage 152 is connected to an actuating mechanism, such as a plunger 156, at a distal end 158 of the insertion tool and is connected to a deformable coupling 160 at a proximal end 162 of the insertion tool 150. (In an alternative embodiment (not shown) the locking mechanism can be a bayonet-type mechanism, which engages the alternate locking mechanism to maintain the plunger in a depressed position.) The deformable coupling 160 fits into an inner recess 113 in an entrance channel 114 in the distal portion 105 of the body 101 of the urethral apparatus 100, thereby locking the insertion tool 150 with the apparatus 100. FIG. 2 shows the insertion tool 150 uncoupled from the apparatus 100 with the deformable coupling 160 at the proximal end 162 of the insertion tool 150 in an uncompressed mode, and FIG. 5A shows the insertion tool 150 coupled to the urethral apparatus 100 with the deformable coupling 160 in a compressed mode.

C. Sensing Component.

Referring again to FIG. 1, the urethral apparatus 100 includes a sensing component 112. In this embodiment, the sensing component 112 is associated with the body 101, and in particular, the sensing component 112 is located along the axial length of the body 101. The sensing component 112 senses a change in the environment of the urethra or a change in a feature of the urethra as the apparatus is being positioned in the urethra. For example, the sensing component 112 may respond to changes in anatomical features of the urethra as a portion of the apparatus 100 moves along the urethra and enters the bladder neck and bladder. The sensing component 112 does not necessarily measure any particular condition or feature but instead detects a change in a condition, parameter, or feature. For example, the sensing component 112 may detect a change from a compressed state to an uncompressed state or to a less-compressed state, from an environment where outward force is registered to an environment where the same force is either no longer registered or is contained with less resistance, or from having one light or sound reflection quality or parameter to an environment having a different reflection quality (e.g., the urethra versus the bladder neck or the bladder). As such, the sensing component 112 can be a tactile sensor, a pre-loaded spring, a force-sensitive contact, a photo cell interacting with a fiber optic strand by radiating and receiving reflected light, a pair of fiber optic strands, a piezoelectric transducer or a membrane switch, a pneumatic or hydraulic electrical or mechanical indicator, a strain gauge, an acoustical-reflection sensor, a thermal couple, a thermistor, or a fluid-introduction port or fluid circuit in combination with a movable element actuating electrical or mechanical components. Utilizing any of these or other sensing technologies to sense any of the features or conditions in the urethral environment, the sensing component 112 includes appropriate scaling so that it can provide a positive indication when the apparatus is properly positioned relative to the features of the urethral environment. By appropriate scaling, the sensitivity of the sensing component is established so that it outputs a signal (preferably a single signal) indicating proper placement of the tubular body relative to the bladder neck and bladder. In this manner the sensing component distinguishes the change in the sensed feature from the urethral background environment to provide a signal indicating that the bladder neck or bladder have been reached.

Figure 5A:
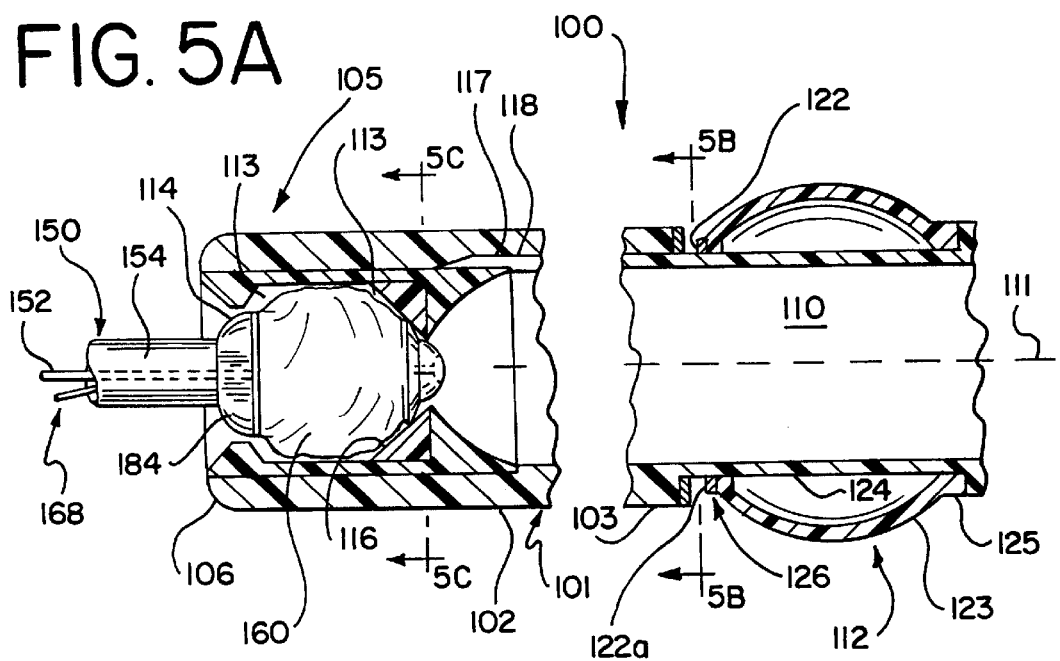
FIG. 5A is a side sectional view of the urethral apparatus of FIG. 1 and a partially cutaway view of a proximal portion of the insertion tool, coupled to the urethral apparatus.

One embodiment of the sensing component 112 is described in conjunction with FIGS. 5A through 5C. This embodiment of the sensing component is a mechanical-type sensor or pressure sensor. This embodiment of the sensing component 112 is responsive to compressive forces applied to a portion of the body 101 of the urethral apparatus 100.

The sensing component 112 comprises a first wall 123 and a second wall 124. The first and second walls are formed of tubular parts of the body 101 of the urethral apparatus 100 close to the proximal end 108. The first wall 123 has shape-memory characteristics and assumes at least first and second positions (compare, for example, FIGS. 7 and 8 with FIGS. 9 and 10). In this embodiment, the first wall 123 is resilient and flexible. The first wall 123 is formed so that it bows outward, as shown in FIG. 5A, in its at-rest condition. In this bowed condition, the first wall 123 is spaced away form the second wall 124, as shown in FIG. 5A. However, when compressive forces are applied to the first wall 123, it deflects to the flattened condition shown in FIG. 7. Movement from the bowed-out condition to the flattened condition causes a corresponding movement of axial length of the first wall 123. Because the proximal end 125 of the first wall is fixed, the distal end 126 of the first wall 123 is caused to move proximally or distally as a result of the bowing out or flattening of the first wall 123.

Referring to FIGS. 5A, 5B, and 5C, lead wires 117 and 118 interconnect conducting surfaces 116a and 116b of the apparatus first contact collar 116 to conducting surfaces 120a and 120b, respectively, of an apparatus second contact collar 120. As shown in FIG. 5B, the apparatus conducting surfaces 120a and 120b are separated by apparatus non-conducting surfaces 120c and 120d. The distal end 126 of the first wall 123 has an apparatus third contact component 122 which has a continuous metalized conducting surface 122a. Completion of an electrical circuit between the apparatus second contact collar 120 and the apparatus third contact component 122 provides a feedback signal to the person positioning the apparatus, such as the caregiver, that the urethral apparatus is in the urethra. Conversely, opening the electrical circuit between the apparatus second contact collar 120 and the apparatus third contact component 122 provides a feedback signal that the urethral apparatus is properly positioned in the bladder neck or bladder (explained in more detail below). This allows the circuit between the apparatus second contact collar 120 and the apparatus third contact component 122 to be alternately opened or closed, depending on the position of the urethral apparatus 100 along the urinary tract.

FIGS. 6A and 6B show the apparatus first contact collar 116 in more detail and show conductive surfaces 116a and 116b separated by nonconductive surfaces 116c and 116d. In an alternative embodiment, the apparatus first contact collar 116 can be replaced with a contact film having conducting areas corresponding to the conductive surfaces 116a and 116b and non-conducting areas corresponding to the surfaces 116c and 116d.

D. Insertion Tool Indicator Unit.

The sensing component 112 in the urethral apparatus 100 works in conjunction with the insertion tool 150. Referring to FIGS. 2 and 3, the proximal end 162 of the insertion tool 150 includes an atraumatic proximal tip 172 and an insertion tool contact collar 170. The tool contact collar 170 is composed of three conductive areas 170a, 170b, and 170c. The contact collar 170 has an oval cross-sectional shape.

The insertion tool 150 includes an indicator unit 164 (FIG. 1). The indicator unit 164 uses any of various visual, audible, or other signaling indicators (e.g., a first light 165, a second light 166, and an alarm 167) that (1) receive electrical feedback that the urethral apparatus 100 and the insertion tool 150 are coupled and (2) receive feedback from the sensing component 112 that the apparatus 100 is properly positioned. This information is relayed along the tool shaft 154 through a lead bundle 168, for example, to the indicator unit 164 where it is observable by the caregiver or the patient. The indicator unit in the insertion tool 150 is powered by a battery (not shown).

(In alternative embodiments, all or part of the functions of the indicator unit may be located at the distal end of the urethral apparatus. Such embodiments may be used in conjunction with an insertion tool that is used to facilitate positioning or may be used without insertion tools. In embodiments of the urethral apparatus in which the distal portion of the body of the urethral apparatus extends outside of the urethra during use, the indicator unit may be incorporated into the distal portion and may include appropriate audible, visual, or other signaling to indicate that the apparatus is properly positioned.)

E. Operation—placement.

Figure 4B:
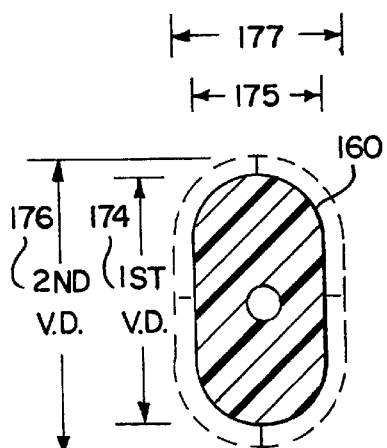
FIG. 4B is an end view of the deformable coupling of FIG. 4A.
Figure 4C:
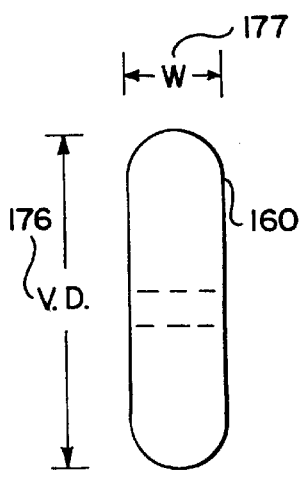
FIG. 4C is a side view of the deformable coupling of FIG. 4A in a locked position.

Referring to FIG. 2, in the uncoupled mode, the deformable coupling 160 of the insertion tool 150 has a first diameter 174 and a first width 175 (as shown in FIGS. 4A and 4B) and is able to pass through the tapered distal end 106 of the tubular body 101. The proximal end 162 of the insertion tool 150 is inserted into the entrance channel 114 and into the inner recess 113, which has a greater vertical cross-sectional area. The deformable coupling 160 is compressed by an actuating linkage 152 using the plunger 156. The vertical diameter of the coupling 160 is extended to a second, larger diameter 176 and a second width 177 (FIG. 4B and 4C), thereby pressing the deformable coupling 160 into the outer extremities of the inner recess 113 of the urethral apparatus and pressing the conductive areas 170a, 170b, and 170c of the insertion tool contact collar 170 against the conductive surfaces 116a and 116b of the apparatus first contact collar 116 (FIG. 5A). This contact activates the first light 165 of the indicator unit 164 providing a feedback signal that the insertion tool 150 and the urethral apparatus 100 are coupled. The two units are now securely engaged together and are ready for insertion into the urethra. As shown in FIG. 1, a biasing force applied to the plunger 156 (and thereby to the linkage 152) by the spring 178 helps to maintain the deformable coupling 160 in a locked or coupled mode, and the stop 179 aids to limit travel of the plunger 156 thereby controlling the diameter of the deformable coupling 160. Further, a locking mechanism can be provided, such as a simple screw 180 and nut 181 combination, to secure the plunger shaft 182 in an uncompressed mode.

Figure 7:
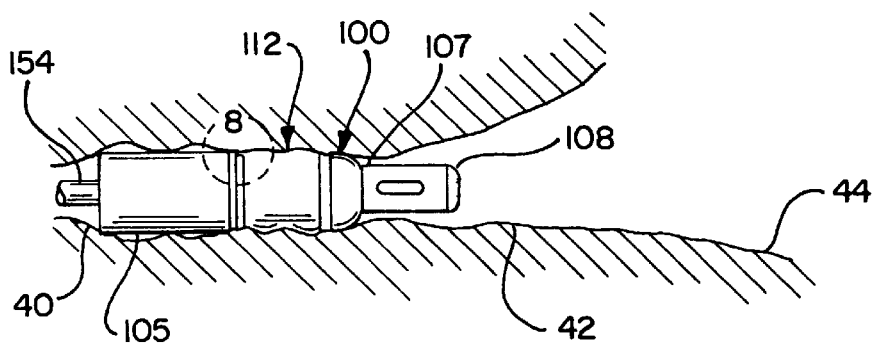
FIG. 7 is a side view of the proximal segment of the coupled urethral apparatus and insertion tool of FIG. 1 in one stage of being positioned in a urethra.
Figure 8:
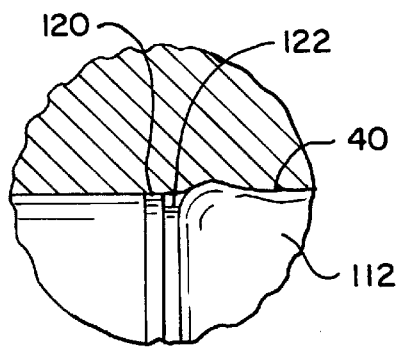
FIG. 8 is a close-up view of a distal end of the sensing component of the urethral apparatus during the stage of positioning shown in FIG. 7.

FIGS. 7 and 8 show the coupled insertion tool 150 and urethral apparatus 100 being inserted into the urethra 40. In FIGS. 7 and 8, the urethral apparatus 100 is passing through the urethra 40 and approaching the bladder neck 42. In this position, the sensing component 112 is responsive to an environment that is relatively consistent within the urethra 40. In this example, the sensing component 112 is in a flattened configuration, and the apparatus second contact collar 120 is in contact with the apparatus third contact component 122, which is part of the sensing component 112. This circuit between the apparatus second contact collar 120 and the apparatus third contact component 122 is maintained while the proximal end 108 of the urethral apparatus 100 is still within the urethra 40. As the coupled urethral apparatus 100 and insertion tool 150 are advanced through the urethra 40, the sensing component 112 is deformed due to the compressive forces exerted by the continuous surface of the urethra 40.

Figure 10:
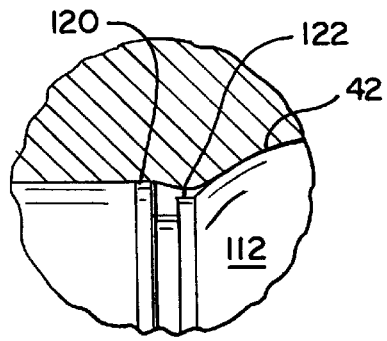
FIG. 10 is a close-up view of a distal end of the sensing component of the urethral apparatus during the stage of positioning shown in FIG. 9.
Figure 9:
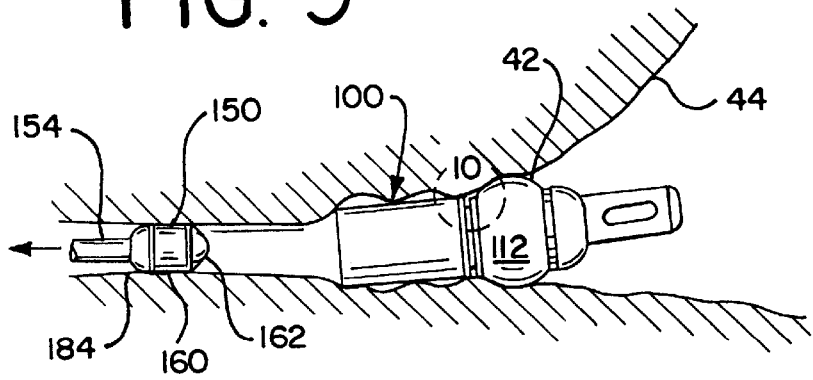
FIG. 9 is a side view of the coupled urethral apparatus and insertion tool of FIG. 7 in another stage of being positioned in the urethra.

As shown in FIGS. 9 and 10, when the urethral apparatus 100 moves into the larger diameter channel of the bladder neck 42 or bladder 44, the sensing component 112 undergoes a change in shape. This change causes the apparatus third contact component 122 to move away from the apparatus second contact collar 120, opening that circuit and thereby sending a feedback signal to the person positioning the urethral apparatus, such as the caregiver, that the urethral apparatus 100 is in proper position in relation to the bladder neck 42. The insertion tool 150 can now be uncoupled from the urethral apparatus 100. FIG. 9 shows the insertion tool 150 uncoupled from the urethral apparatus 100, leaving the urethral apparatus 100 in proper position in relation to the bladder neck 42 and bladder 44. The proximal end 162 of the insertion tool 150 may have a tapered transition 184 from the shaft 154 to the deformable coupling 160 to ease withdrawal of the insertion tool 150.

F. Operation—Removal of apparatus.

Removal of the urethral apparatus 100 is accomplished using the above steps in reverse order. The linkage 152 of the insertion tool 150 is actuated by the plunger 156 and locked to maintain the deformable coupling 160 in the first diameter 174 and the first width 175. The insertion tool 150 is inserted into the urethra until it engages the distal end 106 of the urethral apparatus 100. The proximal end 162 of the insertion tool 150 is further inserted into the entrance channel 114 of the distal end 106 of the urethral apparatus 100 until the tool contact collar 170 of the insertion tool 150 engages the apparatus first contact collar 116. This engagement can be confirmed by observing actuation of the first light 165. The deformable coupling 160 is then changed to the second, larger diameter 176 and the second width 177 by releasing the plunger 156 thereby locking the insertion tool 150 to the urethral apparatus 100. Once coupled, removal of the tool and urethral apparatus can proceed by pulling on the distal end of the tool.

G. Use of an Insertion Sleeve.

In alternative embodiments, the coupled or joined urethral apparatus 100 and insertion tool 150 can be inserted in the urethra with the aid of an insertion sleeve (not shown), which is inserted in the urethra 40 either prior to or simultaneously with the joined urethral apparatus and tool. The insertion sleeve can be a short or a long sleeve, or an everting sleeve that may aid in reducing the introduction of bacteria higher into the urethra or bladder. The sleeve has a length such that it does not interfere with the sensing component 112 on the body of the urethral apparatus. The sleeve may also have a longitudinal line of weakness to facilitate removal of the sleeve, for example by tearing. Those skilled in the art will realize that a coating on the sleeve, preferably including lubricating and antibacterial substances, may be used to aid in insertion within the urinary tract.

H. Alternative Embodiment of Insertion Tool

FIGS. 11 through 15 show an alternative embodiment 250 of the insertion tool, which can be used for placement of the urethral apparatus 100. The insertion tool 250 provides for an axial orientation of the caregiver's hand during insertion and removal. In this embodiment of the insertion tool 250, the plunger and locking mechanism are integrated within a hand-piece housing 251. A proximal end 262 of the insertion tool 250 has an atraumatic distal tip 272, which is interconnected with a cable or other linkage 252 that passes through a shaft 254 of the insertion tool 250. The linkage 252 is connected to a plunger 256 and has a biasing spring 278 (best shown in FIG. 12). A sleeve 257 serves to center the spring 278 over the linkage 252 (FIG. 13). As the plunger 256 is moved forward and backward, it engages a stop 279 (FIG. 14), which secures a deformable coupling 260 either in an engaged or disengaged position with the urethral apparatus 100. A battery 259, which supplies power for the insertion tool 250, is inserted through a distal end 258 of the insertion tool 250 and is held in place with a nut 281 and a battery spring 261. A ground contact strip 263 for the battery 259 is located adjacent to and in contact with the battery spring 261 and with a ground lead 269. A positive contact 283 for the battery 259 is connected to a positive lead 284 and is connected to the circuitry in an indicator unit 264. FIG. 12 also shows a lead bundle 268 consisting of individual leads 268a, 268b, and 268c (best shown in FIG. 15) that carry feedback signals indicating proper coupling and positioning. The individual leads terminate within the indicator unit 264 which is further detailed in the circuit flow diagrams and descriptions discussed below.

The indicator unit 264 is joined to the shaft 254 of the insertion tool 250 with a slip connector 255. The slip connector 255 allows the distal end 258 to be rotated to aid in coupling the insertion tool 250 with the urethral apparatus 100 and to aid insertion of the coupled tool and urethral apparatus through the urethra.

Referring to FIG. 15, the insertion tool 250 has an insertion tool contact collar 270 close to its proximal end 262. (This contact collar 270 may be similar to the contact collar 170 of the insertion tool 150 in the previously described embodiment.) The contact collar 270 includes three conducting surfaces 270a, 270b and 270c (FIG. 16B), which interface with the conducting surfaces 16a and 16b of the first contact collar 116 of the urethral apparatus 100 to complete a circuit that indicates proper coupling of the insertion tool 250 with the urethral apparatus 100. The conductive surfaces 270a, 270b, and 270c are connected to the three electrical leads, 268a, 268b, and 268c, respectively. These leads are located within the shaft 254 of the insertion tool 250 and terminate within the indicator unit 264 at electrical contacts that communicate with a first light 265, a second light 266, and an alarm 267.

Figure 16B:
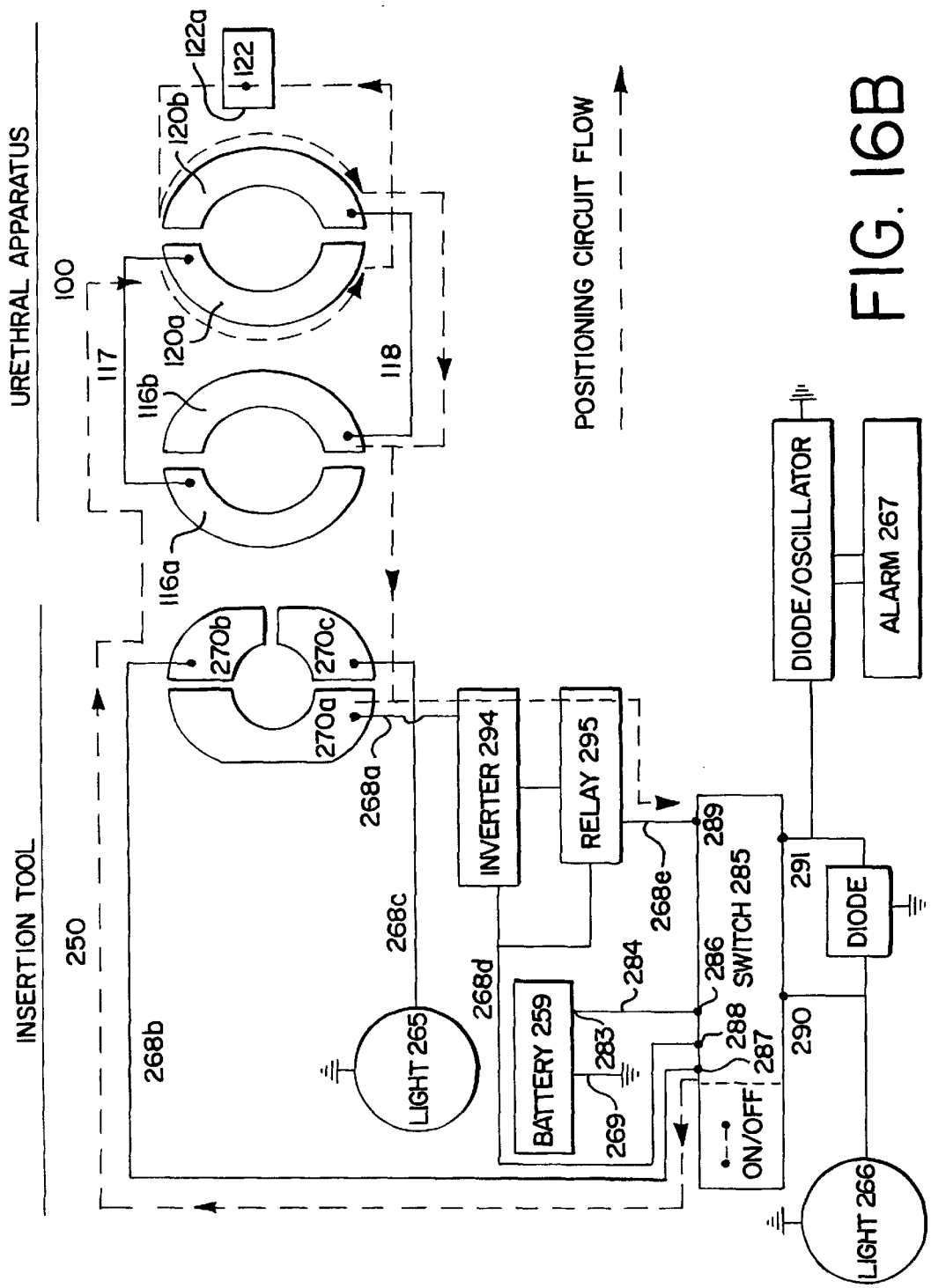
FIG. 16B is a schematic flow diagram illustrating the electrical flow during positioning of the insertion tool and urethral apparatus of FIG. 15.

The electrical circuit flows during coupling and insertion are diagramed in FIGS. 16A and 16B. The circuit flow during coupling is shown in FIG. 16A. The battery 259 is connected to a switch 285 at a first contact 286 by the positive lead 284. A second contact 287 and the conductive surface 270b are interconnected by the lead 268b. When the insertion tool is engaged with or coupled to the urethral apparatus 100, an electrical connection between the insertion tool conductive surfaces 270b and 270c is made when each comes in electrical contact with the conductive surface 116a of the urethral apparatus 100. In this coupled mode, the first light 265 is activated.

Also receiving power through the switch 285 is an inverter 294 and a relay 295, which receive power through a third switch contact 288 and a lead 268d. The switch 285 can be in one of two positions for receiving feedback. The first position is used during coupling, and the second position is used during positioning.

After the urethral apparatus 100 and the insertion tool 250 are coupled, the switch 285 is moved to a second position, and the first light 265 remains lit. FIG. 16B illustrates the circuit flow during insertion and positioning. The sensing component 112 is compressed against the outer surface of the body 101 such that the conductive surface 122a of the third contact component 122 electrically interconnects the second conducting surfaces 120a and 120b of the second contact collar 120. The leads 117 and 118 electrically interconnect the first contact collar 116 with the second contact collar 120. Both the first and second lights 265 and 266 are on unless the switch 285 is in the off position. The inverter 294 translates the electrical signal returning through the lead 268a to indicate when the sensing component 112 becomes uncompressed, i.e. the third contact component 122 located on the sensing component 112 becomes electrically disconnected from the conducting surfaces 120a and 120b when the urethral apparatus 100 enters the bladder, and an electrical signal is transferred through the lead 268e to the switch 285 to activate the second light 266 and/or alarm 267. The second light 266 and the alarm 267 may be selectively activated depending on the user's setting of the switch 285.

In a present embodiment, the switch 285 has four positions. In a first position, the electrical circuitry is off. In a second position (for coupling), the first light 265 is activated when the circuits are completed between the insertion tool contact collar 270 and the first contact collar 116 of the urethral apparatus 100. When the switch 285 is in a third position (for positioning or insertion), the input contact 289 and the light contact 290 are interconnected and the second light 266 activates indicating entrance to a body passageway with increased area (e.g., diameter). In a fourth position, the input contact 289 is interconnected to the light/alarm contact 291 and the second light 266 and the alarm 267 are activated, thereby indicating entrance to a body passageway of increased area (i.e. diameter). The input contact 289 is activated either directly via the voltage source, or with an optional relay 295.

Those skilled in the art will appreciate that the inverter 294 reverses the activation of the second light 266 (or the alarm 267) relative to the operation described in connection with the first embodiment of the insertion tool. Instead of being turned off when a current path between the apparatus conducting surfaces 120*a* and 120*b* and the apparatus component surface 122*a* is interrupted, the inverter 294 causes the second light 266 (or the alarm 267) to be turned on when the current path is interrupted. Thus, the inverter 294 is provided to effect this alternative mode of operation. Accordingly, it is understood that the use of the inverter is optional depending upon the mode desired.

I. Second Embodiment of the Urethral Apparatus:

FIG. 17 shows another embodiment 100A of the urethral apparatus. The urethral apparatus 100A includes a tubular body 101A having a proximal portion 107A terminating in a proximal end 108A. In this embodiment, a sensing component 112A is comprised of a preformed, shape-memory portion incorporating internal electrical switching. The proximal portion 107A includes a preformed portion 131A. The preformed portion 131A is flexible and resilient and has an other-than-straight shape when at rest. A slidable contact 132A is fixed distally at a position 134A and displaced relative to a proximal contact pair 135A as deformation of the preformed portion 131A occurs upon entry into the bladder neck or bladder. This displacement causes the proximal contact pair 135A to open, thus opening an electrical circuit through the apparatus conductive leads 117A and 118A, which interconnect the proximal contact pair 135A and the apparatus first contact collar 116A, which is in contact with the insertion tool 150 (or 250), thereby activating a signal on the indicator unit 164 (or 264) thereof. Optionally, the apparatus proximal contact pair 135A can be located in a more distal position near the apparatus first contact collar 116A. In an alternative embodiment, the preformed portion 131A is incorporated within or utilized with an anchoring mechanism, which provides for an electrical feedback to give an indication of entry into the bladder neck or bladder and to confirm proper positioning in relation to the bladder neck or bladder.

Figure 19A:
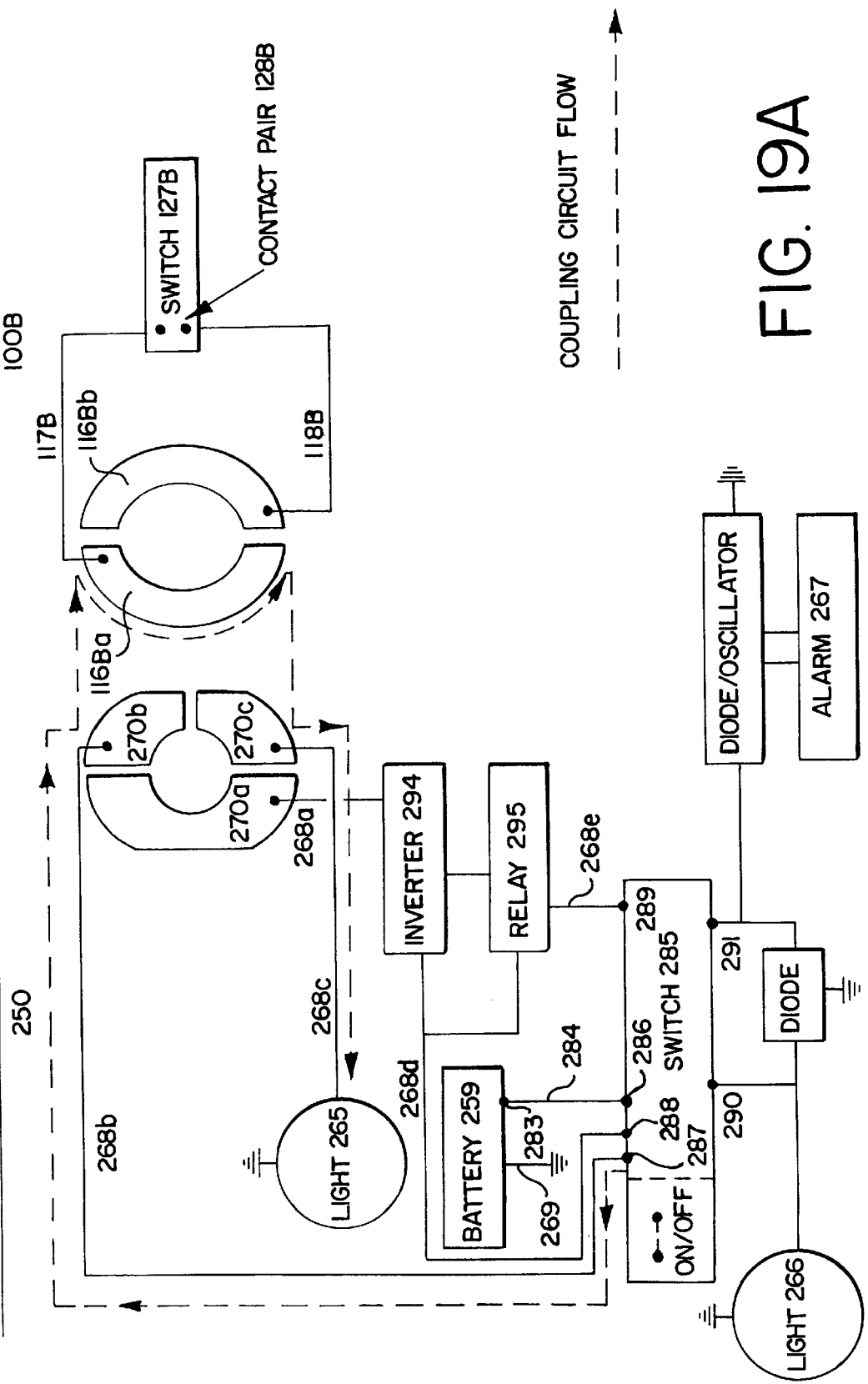
FIG. 19A is a schematic flow diagram illustrating the electrical flow during coupling of the insertion tool and urethral apparatus of FIG. 18.
Figure 19B:
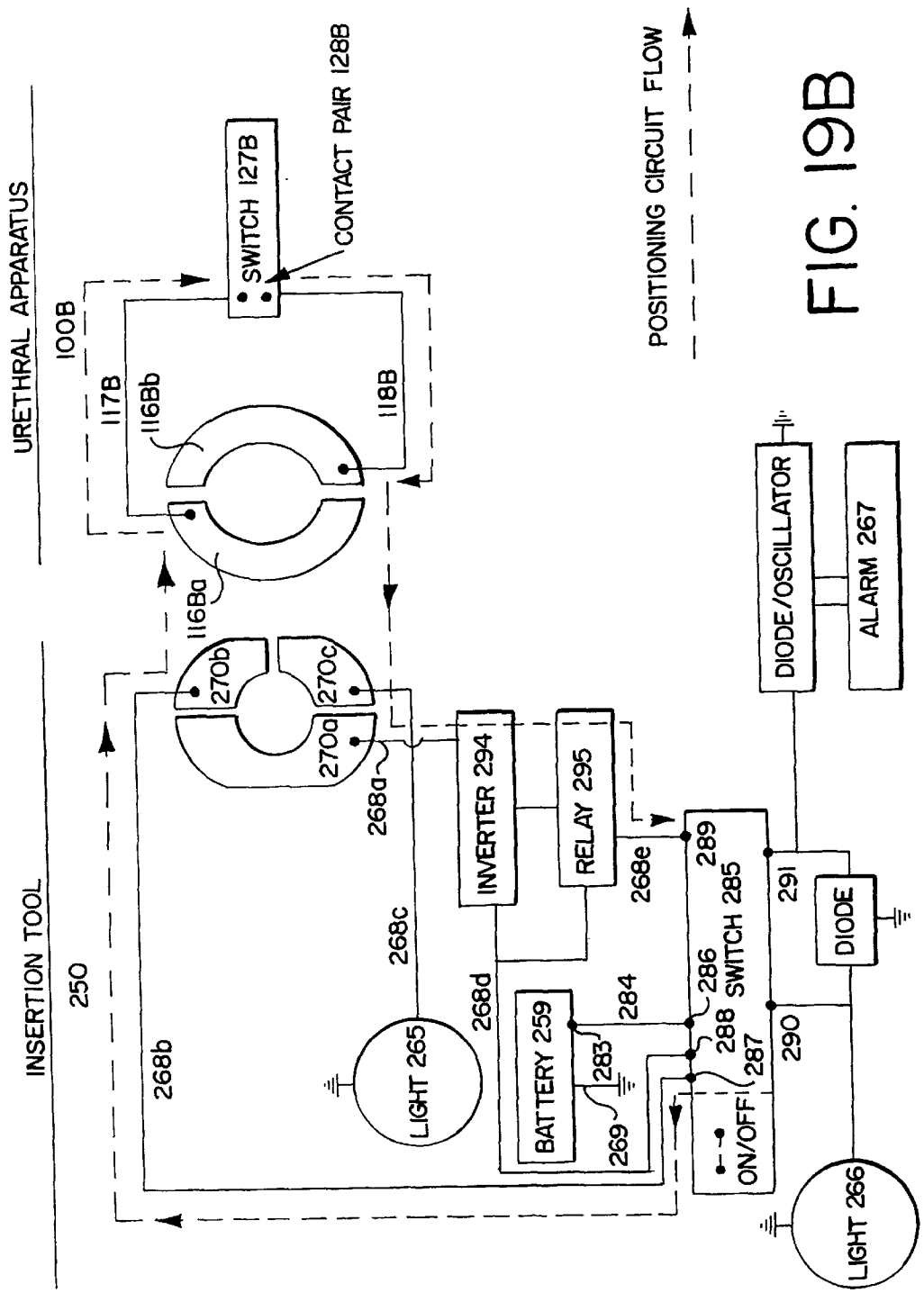
FIG. 19B is a schematic flow diagram illustrating the electrical flow during positioning of the insertion tool and urethral apparatus of FIG. 18.

J. Third Embodiment of Urethral Apparatus:

FIGS. 18, 19A, and 19B show another alternate embodiment of a urethral apparatus 100B. In this embodiment, a sensing component 112B comprises conductive contact terminals that form a switch that can sense entry into a bladder neck or bladder. A proximal portion 107B of a body 101B of the urethral apparatus 100B includes a switch 127B that displaces an internal contact pair 128B (shown in the circuit flow diagram of FIGS. 19A and 19B) as the proximal portion 107B of the urethral apparatus 100B containing the switch 127B enters the bladder neck or bladder. This displacement causes the contact pair 128B to open, thus opening the electrical circuit through the conductive leads 117B and 118B, which interconnect the switch 127B and a first contact collar 116B, which is in contact with the insertion tool 150 (or 250), thereby activating a signal on the indicator unit 164 (or 264) thereof.

III. Embodiments with Acoustic Sensing

A. First Embodiment of a Urethral Apparatus with Acoustic Sensing:

As mentioned above, the sensing component can be designed to sense changes in light, pressure, force, vibration, compression, heat, or other sensed conditions. These alternative embodiments are described below.

Figure 21A:
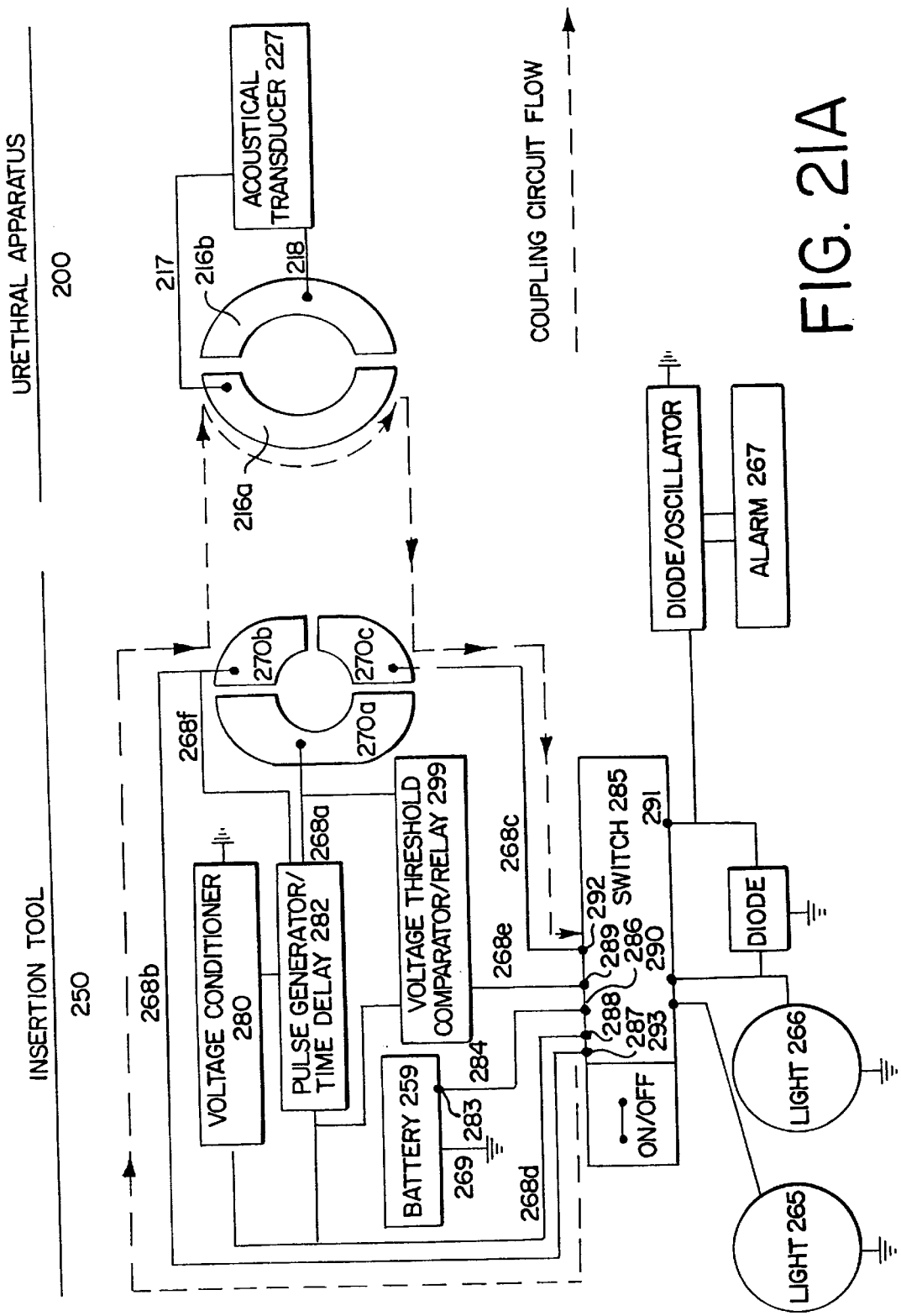
FIG. 21A is a schematic flow diagram illustrating the electrical flow during coupling of the insertion tool and urethral apparatus of FIG. 20.
Figure 21B:
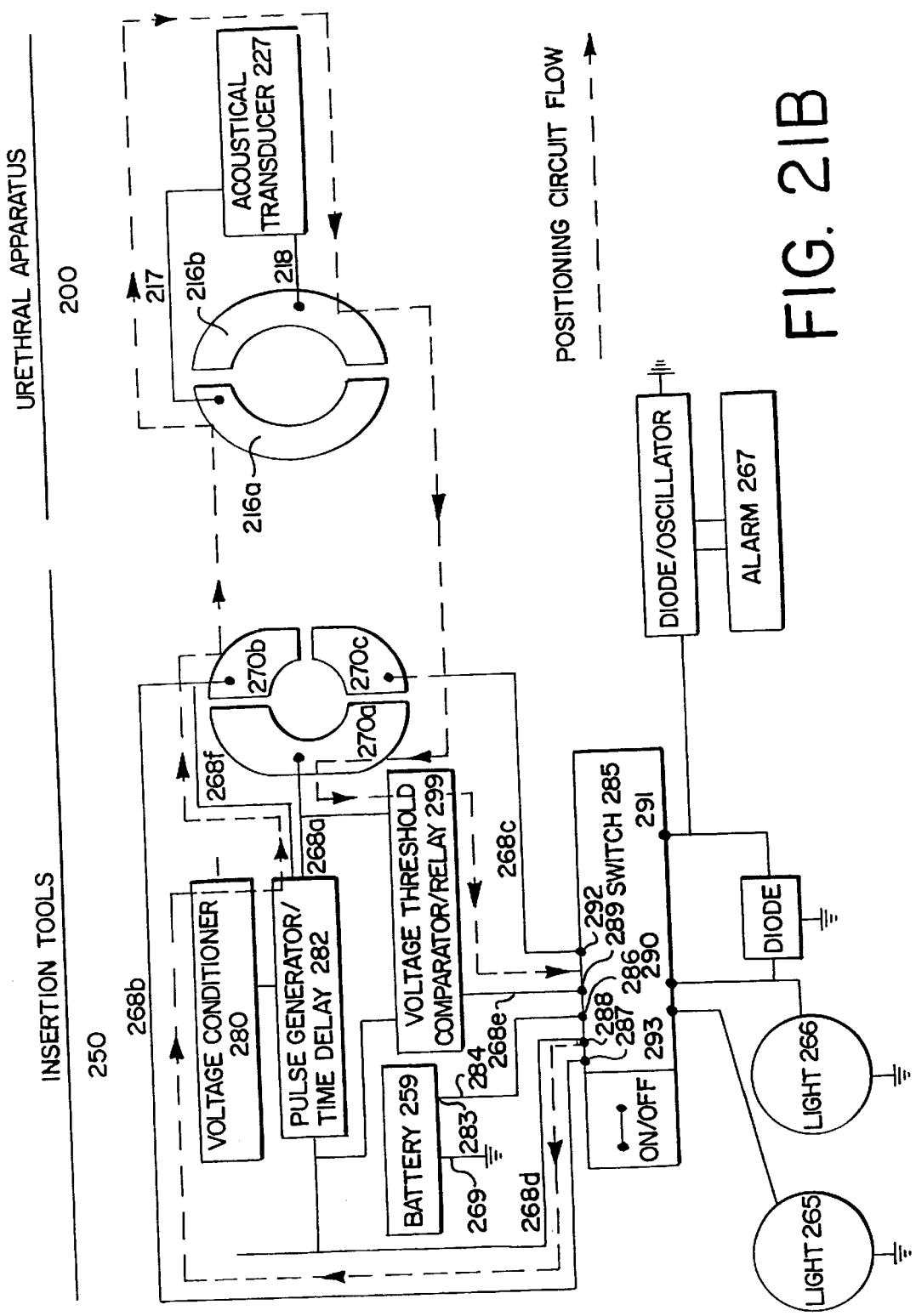
FIG. 21B is a schematic flow diagram illustrating the electrical flow during positioning of the insertion tool and urethral apparatus of FIG. 20.
Figure 24:
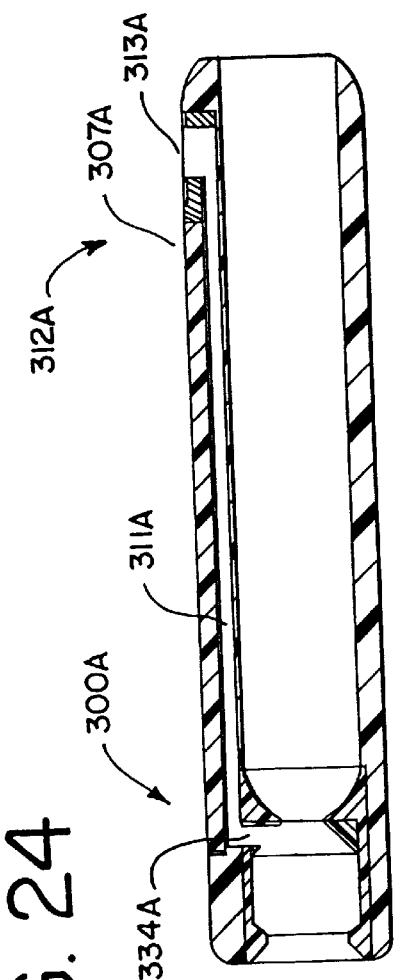
FIG. 24 is a sectional view of a first alternate embodiment of a urethral apparatus that utilizes fluid flow sensing.
Figure 25B:
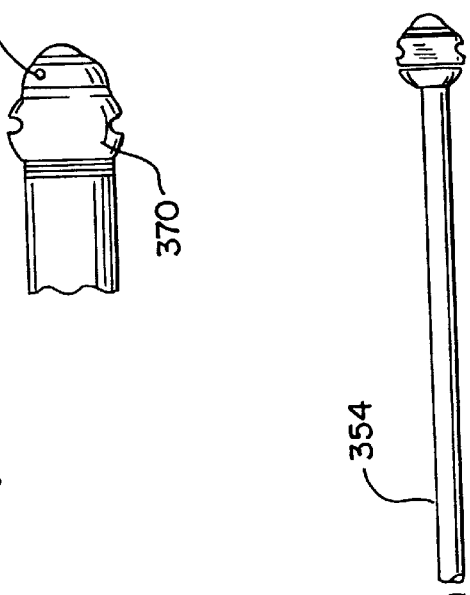
FIG. 25A is a partially cutaway side view of an insertion tool to be used with the embodiment of FIG. 24.
Figure 25A:
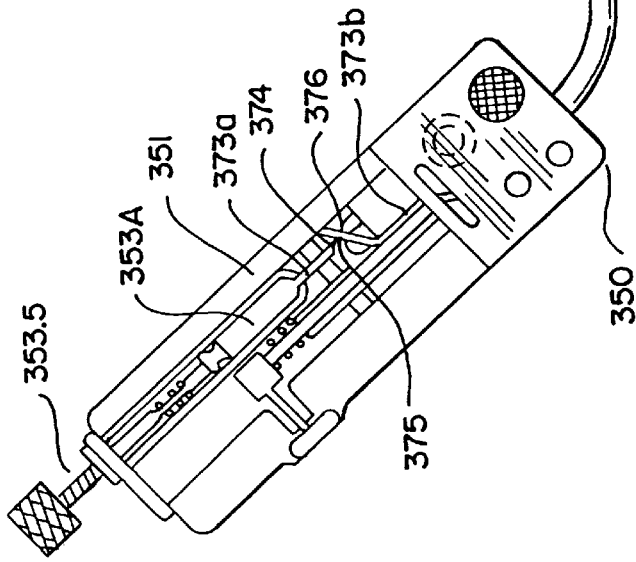
Figure 26B:
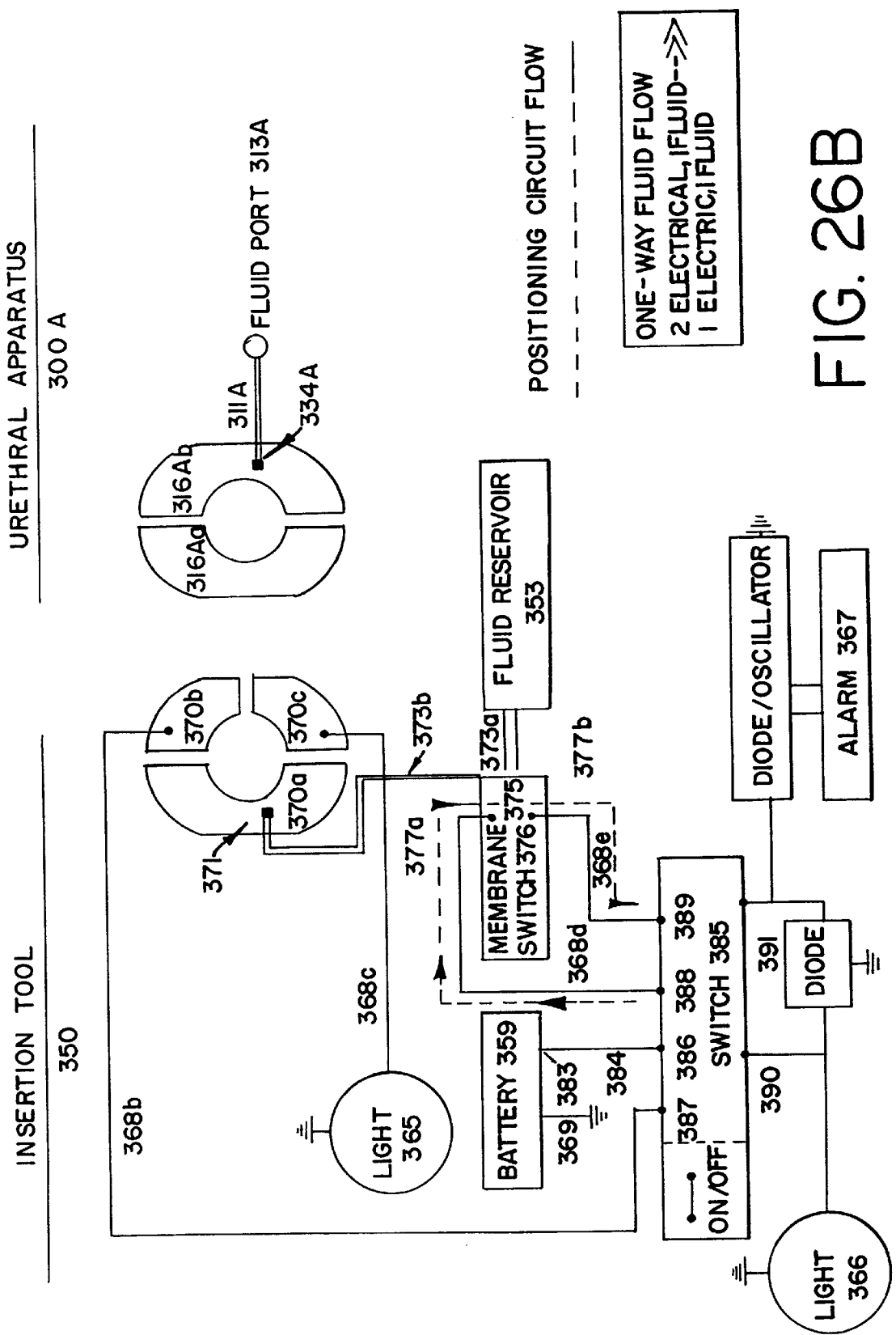
FIG. 26B is a close-up view of the proximal portion of the insertion tool of FIG. 25A.

Referring to FIGS. 20, 21A, and 21B, there is shown an embodiment of a urethral apparatus 200 that utilizes a acoustic sensing component 212 to generate an indication of proper placement. The embodiment of FIGS. 20, 21A, and 21B functions similarly to the embodiment in FIG. 18 except that the switch 127B of FIG. 18 is replaced with an acoustical transducer 227. The acoustical transducer 227 is preferably a piezoelectric acoustical transducer, but alternatively, may be a magnestrictive acoustical transducer. The acoustic transducer 227 is preferably located within the body 201 of the urethral apparatus 200. The acoustic transducer 227 is activated to generate a pulsed mode signal and receive an acoustical signal.

FIG. 21B shows the electrical current flow path during positioning of the embodiment of the urethral apparatus 200 shown in FIG. 20 operating in a pulsed echo mode. Current flows from a third contact 288 of a switch 285 through a lead 268*d* to a voltage conditioner 280. The voltage conditioner 280 (which may optionally be a component of the pulse generator/time delay 282) provides for the necessary preamplification. Following voltage preamplification, the pulse generator/time delay 282 provides for the formation of the excitation impulse wave form used to resonate the acoustical transducer 227. The impulse wave form is transmitted through a lead 268*f* to a conducting surface 270*b* of the insertion tool contact collar 270 and then to the conductive surface 216*a* of the first contact collar 216 of the urethral apparatus 200. The wave form is then transmitted through the lead 217 to the acoustical transducer 227.

The acoustical transducer 227 is resonated at the characteristic frequency of the transducer which may range from as low as approximately 1 Kilohertz to as much as approximately 100 Megahertz. In one embodiment, a range of resonate frequencies within two orders of magnitude of 1 Megahertz is appropriate. The resonate frequency of the transducer is dependent on its material properties and thickness. The pulse generator wave form is a triangular or square wave with amplitudes ranging up to approximately 100 volts. The pulse generator/time delay 282 provides for an excitation voltage followed by a wait state prior to re-initiation of the next resonance. The resonance of the transducer 227 provides for an energy transmission into the adjacent materials; this transmission is in the form of an acoustical beam as the energy is transmitted through the adjacent material at the speed of sound of the material itself.

The surrounding materials either reflect, absorb, or transmit the energy. The energy that is reflected provides an indication of the surrounding environment. The initial reflections which impact the acoustical transducer surface 204 following the completion of the resonance from the initial excitation re-resonate the transducer 227. This resonance produces an electrical potential (voltage) at the surfaces which is conducted back through leads 217 and 218 to the conductive surfaces 216*a* and 216*b* of the first contact collar 216, through the conductive surfaces 270*a* and 270*b* of the insertion tool contact collar 270, and to the pulse generator/time delay 282 through leads 268*a* and 268*f*.

The voltage differential between the leads 268*a* and 268*f* diminishes substantially during the pulsed echo cycle when the acoustical transducer 227 enters the regions of increased area in the bladder neck and bladder. Because the distance from the acoustical transducer surface 204 to the body tissue surface increases at the bladder neck and bladder, there is a substantial reduction in the reflected energies compared to the more intimate contact within the tighter areas of the body such as the urethra.

The voltage threshold comparator and a relay 299 register the peak reflected voltage. When the average peak voltage produced by the reflected energy is less than the predetermined threshold (or alternatively a differential between high and low reflected peak voltages), an input contact 289 is activated either directly via the voltage source, or with an optional secondary relay (not shown). When the switch 285 is in a position in which the input contact 289 and the light contact 290 are interconnected, the second light 266 lights indicating entrance to a body cavity with increased area. Alternatively, when the switch 285 is in the position where the input contract 289 and the light/alarm contact 291 are interconnected, both the second light 266 and the alarm 267 are activated.

Upon receipt of the pressure wave on the acoustical transducer 227, a voltage is generated and transmitted to the insertion tool 250 external to the patient's body where the wave form is processed using the analog or digital circuitry contained within insertion tool 250. The distance away from the transducer to the surface of the urethra, bladder neck, or bladder is determined by the elapsed time from the completion of a generated signal until the first wave return. Alternatively, the distance from the transducer to the surface of the urethra, bladder neck, or bladder is determined by the change in intensity of the reflected acoustical waves. In either case, a change in state becomes apparent by the acoustical reflections as the apparatus 200 enters the or bladder. The insertion tool 250 then generates an appropriate audible, visual, analog, or other signal of this change.

B. Alternate Embodiments of Insertion Tool:

Several other embodiments of the sensing component are described below that use other methods of initiating feedback to the caregiver that the urethral apparatus is properly positioned. Among these other embodiments are the use of one- and two-way fluid flows, fiber optics, electrical resistance, thermoelectric semiconductors, and two-transducer acoustic mechanisms. These embodiments use an alternate embodiment of the insertion tool electrical contact collar.

Referring now to FIGS. 22A through FIG. 22D, an alternate embodiment of an insertion tool contact collar 270A for use with the urethral apparatus first contact collar (e.g., 116 or 216) allows for additional convenience when coupling. Both contact collars include conducting surfaces and non-conducting surfaces that form circuits to indicate either coupling of the insertion tool with the urethral apparatus or proper positioning within the bladder neck or bladder. In further embodiments, both contact collars are oval-shaped and have additional mating contact points to accommodate various fluid-flow pathways and fiber optics connections. For convenience, there are twice as many of these additional mating contact points on the insertion tool contact collar 270A as there are mating contact points on the urethral apparatus first contact collar (116 or 216) so that either of the two 180-degree orientations are functional.

FIG. 22A shows the proximal portion of the insertion tool 250 and further illustrates the assembly of the contact collar 270A to the contact collar housing 270.5. Also shown in the figure is the contact collar 116 (or 216) of the urethral apparatus 100 (or 200) to illustrate how the contact collars of the insertion tool 250A and the urethral apparatus 100 (or 200 and following embodiments) interface with one another.

The table below shows the number and type of the contact points or mating contact points provided on the insertion tool contact collar 270A, the urethral apparatus first contact collar 116 (or 216), and the number of leads for the various embodiments in this disclosure. As mentioned above, the number of contact points or ports on the insertion tool contact collar 270 may be doubled for convenience when coupling.

| Embodiment | Insertion Tool Contact collar Tool Contacts* | Urethral Apparatus Contact collar Insertable Contacts | Urethral Apparatus Leads |
|---|---|---|---|
| Electrical Switch | 3 electrical | 2 electrical | 2 electrical |
| Acoustic (1 transducer) | 3 electrical | 2 electrical | 2 electrical |
| Fluid - 1 way flow | 2 electrical 1 fluid port | 1 electrical 1 fluid port | 1 fluid port |
| Fluid - 2 way flow | 2 electrical 2 fluid ports | 1 electrical 2 fluid ports | 2 fluid ports |
| Electrical Resistance | 3 Electrical | 2 electrical | 2 electrical |
| Thermoelectric Semiconductor | 3 electrical | 2 electrical | 2 electrical |
| Fiber Optic-Fiber Optic | 2 Electrical 2 Fiber Optic | 1 electrical 2 fiber optic | 2 f. optical |
| Fiber Optic-Photocell | 4 Electrical 1 fiber optic | 3 electrical 1 fiber optic | 2 electrical 1 fiber optic |
| Acoustic (2 transducer) | 5 electrical | 4 electrical | 4 electrical |

(*number of contact points can be doubled.)

C. Second Embodiment of a Urethral Apparatus with Acoustic Sensing:

FIG. 23 illustrates a second acoustic embodiment (apparatus 200A). In this embodiment, a sensing component that uses acoustic sensing in shown generally at 212A. This embodiment utilizes two magnestrictive, or preferably, piezoelectric acoustical transducers 227A(1) and 227A(2) on an exterior surface 203A of the urethral apparatus 200A. These transducers 227A(1) and 227A(2) are activated to respectively generate and receive a continuous mode acoustical signal. This embodiment is similar to the first acoustic embodiment except that in this embodiment, a first transducer 227A(1) generates a continuous mode acoustic signal rather than a pulsed signal, while a second transducer 227A(2) receives the signal. Electrical leads 217Aa, 217Ab, 218Aa, and 218Ab carry an electrical potential (voltage) to and from the transducers 227A(1) and 227A(2), respectively, and are interfaced with electrical leads 268 in the insertion tool 250 through the contact collars 270 and 216A to provide for a feedback signal. Circuitry in the insertion tool is similar to that shown for the first acoustic embodiment (see FIG. 21A) except that the pulse generator is replaced by a continuous mode generator.

As the urethral apparatus 200A is inserted into the urethra, the surrounding materials either reflect, absorb, or transmit the energy. Acoustic energy is emitted by the first acoustical transducer 227A(1), reflected by the urethral wall, and received by the second transducer 227A(2), which resonates and produces an electrical potential (voltage) that provide an indication of the surrounding environment. This voltage diminishes substantially when the transducers enter the bladder neck and bladder where the distance from the transducer surfaces to the body tissue surface increases and causes a substantial reduction in the reflected energies compared to the more intimate contact within tighter areas of the body such as the urethra.

In an alternate embodiment, the two transducers are placed facing each other, separated by a non-reflective, shape-memory member similar to that used in the fiber optic embodiments, described below. A change is acoustic signal is noted when the proximal end of the urethral apparatus carrying the transducers enters the bladder neck and bladder, thereby allowing the shape memory member to be displaced outward which, in turn, permits an unobstructed face-to-face orientation of the two transducers.

Embodiments with Fluid Flow Sensing

Pressurized fluid flow may be used to provide for position feedback to ascertain that the urethral apparatus is properly positioned. Four approaches using pressurized fluids in combination with an insertion tool and urethral apparatus are described below. The first three approaches provide a one-way flow of fluid from an insertion tool, through the urethral apparatus, and into the urethra, bladder, or a fluid reservoir located in urethral apparatus. This flow can be restricted to varying degrees. In these embodiments as the coupled insertion tool and urethral apparatus pass through the urethra, fluid flow is restricted because of the urethra. However, as the proximal portion of the urethral apparatus enters the bladder neck or bladder, the flow becomes less restricted. This change in fluid restriction is detected by circuitry in the insertion tool. The fourth approach, described below, does not permit fluid to escape into the urethra and bladder, but incorporates a two-way flow of fluid from the insertion tool, through the urethral apparatus, and back to the insertion tool.

A. First Embodiment of a Urethral Apparatus with Fluid Flow Sensing:

A first fluid flow embodiment is shown in FIGS. 24, 25a, 25b, 26a and 26b. A urethral apparatus 300A provides for a limited passage of fluid into the urethra or bladder. In this embodiment, the sensing component is shown generally at 312A. In this embodiment, fluid is allowed to pass from an insertion tool 350 and into a urethral apparatus 300A. The fluid is under pressure in a fluid reservoir 353 that is contained within the insertion tool 350. Pressure can be applied by a thumb screw and piston in combination with a biasing spring 353.5 located on the distal end of a handpiece housing 351. Fluid flows through a fluid passageway 373a, through a passageway port 374, against the a flexible conduit wall 375 which contacts a normally closed, pressure-responsive membrane switch 376, and through a fluid passageway 373b that extends through a shaft 354.

When fluid is in stasis due to resistance or complete retention of fluid, the normally closed membrane switch 376 is electrically open. When the fluid pressure diminishes due to a dynamic fluid state, the flexible conduit wall collapses under the pressure of the normally closed membrane switch 376. The fluid then flows through a mating contact point 371 of an insertion tool contact collar 370 through a contact port 334A of the urethral apparatus 300A, through a passageway 311A, and out through a apparatus port 313A, which could be a porous or microporous membrane. The fluid is expelled into the urethra, the bladder neck, or the bladder, depending upon the location of the coupled insertion tool 350 and apparatus 300A.

The change in restriction of flow is detected by the normally closed membrane switch 376. As the apparatus 300A enters the bladder neck or bladder, the fluid encounters less pressure due to the lack of surface contact with the urethra. Since the source of this fluid pressure is within the insertion tool 350, the membrane switch 376 detects the lower system pressure. The pressure-responsive, normally closed membrane switch 376 then returns to the unengaged position and closes the internal contacts, thus completing a circuit between the contacts 377a and 377b, the energizing input contact 389 and the second light 366. Depending on the position of the switch 385, either the light only, or the light and alarm, gives an indication that the proximal portion 307A of the urethral apparatus 300A has entered the bladder neck or bladder as previously described in the other embodiments. The input contact 389 is activated either directly via the voltage source or with an optional secondary relay (not shown).

Figure 27:
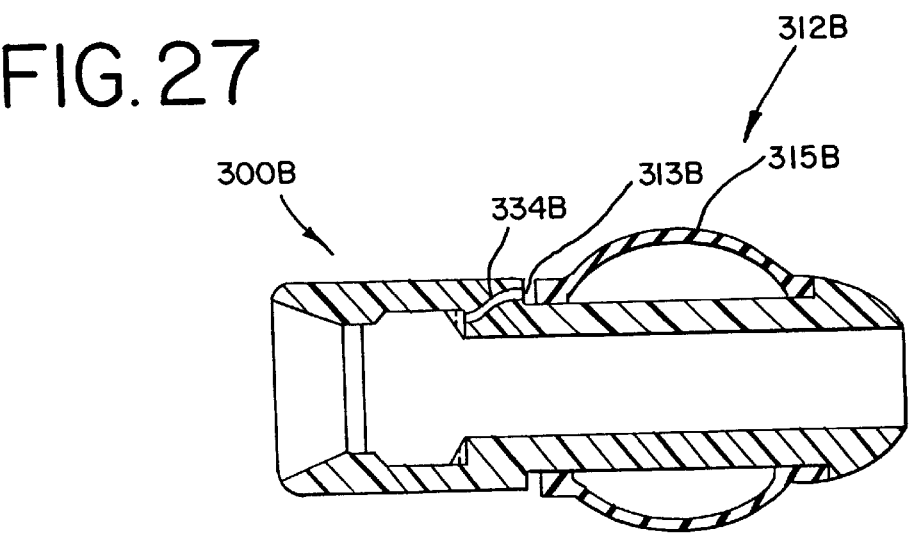
FIG. 27 is a sectional view of a second alternate embodiment of a urethral apparatus that utilizes fluid flow sensing.

B. Second Embodiment of a Urethral Apparatus with Fluid Flow Sensing:

Referring to FIG. 27, there is shown a second embodiment 300B of a urethral apparatus that uses fluid-flow for sensing. In this embodiment, the sensing component is shown generally at 312B. This embodiment provides for a limited passage of fluid into the bladder neck or the bladder when a proximal portion of the apparatus 300B containing a restricted apparatus port 313B enters the bladder neck or bladder. This configuration is similar to the first fluid-flow embodiment 300A except that no fluid is allowed to pass into the urethra during insertion due to the physical contact of the urethra on the flow restrictor valve 315B that thereby closes the apparatus port 313B. The system mechanics and electronics function similarly to the first fluid-flow configuration.

Figure 28:
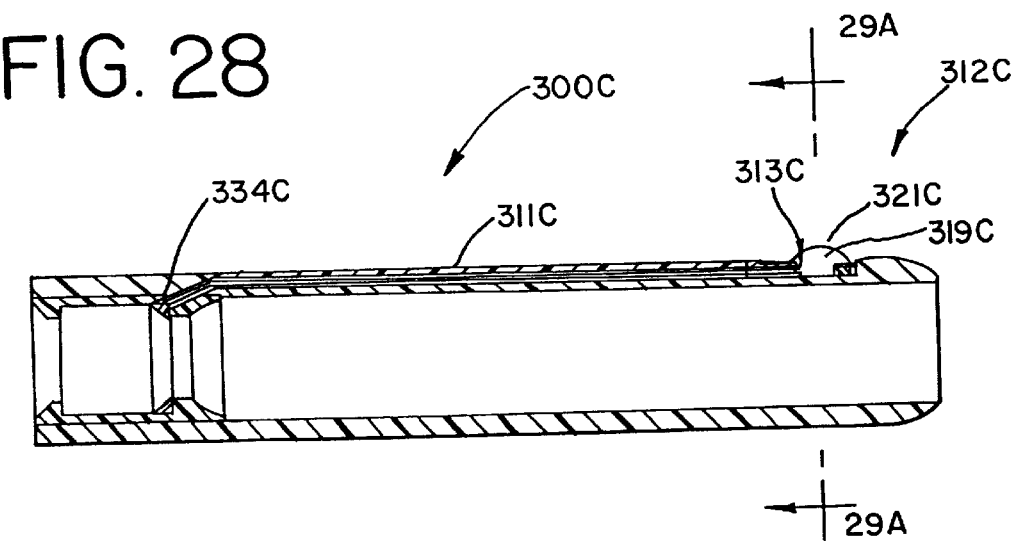
FIG. 28 is a sectional view of a third alternate embodiment of a urethral apparatus that utilizes fluid flow sensing.
Figure 29A:
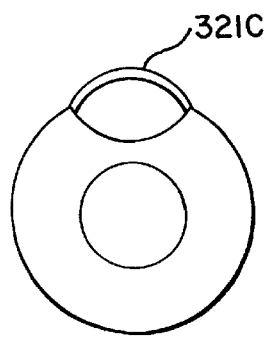
FIG. 29A is a cross-sectional view taken along line 29A–29A' of FIG. 28 showing the volume-deformable member in an expanded configuration.
Figure 29B:
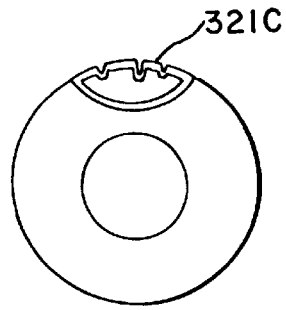
FIG. 29B is the same cross-sectional view as shown in FIG. 29A showing the volume deformable member in a depressed configuration.

C. Third Embodiment of a Urethral Apparatus with Fluid Flow Sensing:

A third embodiment of a urethral apparatus 300C using a fluid-flow configuration is shown in FIG. 28 through FIG. 29B. In this embodiment, the sensing component is shown generally at 312C. This embodiment provides for fluid feedback without the introduction of fluid into either the urethra, bladder neck, or bladder by providing for a one-way fluid flow from the insertion tool 350 into a fluid reservoir 319C located in the urethral apparatus 300C. Adjacent to the fluid reservoir 319C is a volume-deformable member 321C. As in the first two fluid-flow configurations, the fluid is under pressure in the reservoir 353 contained within the insertion tool 350. This fluid flows through the fluid passageway 373a and 373b, through the shaft 354, then through the mating contact point 371 of the insertion tool contact collar 370, through a contact port 334C of the urethral apparatus 300C, through the apparatus passageway 311C and the port 313C, and into a fluid reservoir 319C. As the insertion tool 350 and the urethral apparatus 300C are introduced through the urethra, the volume-deformable member 321C is in a flattened profile, as shown in FIG. 29a. When the portion of the urethral 300C containing the volume-deformable member 321C enters the bladder neck or bladder, fluid pressure within the system causes the volume-deformable member 321C to deform to a second, larger profile as shown in FIG. 29b, thus lowering fluid pressure within the circuit. This change in fluid pressure causes the pressure-responsive, normally closed membrane switch 376 to return to the undeflected position, thus completing a circuit between the contacts 377a and 377b and the energizing input contact 389 and the second light 366. The system electronics function similarly to the first two fluid-flow configurations.

D. Fourth Embodiment of a Urethral Apparatus with Fluid Flow Sensing:

A fourth embodiment of a urethral apparatus 300D that uses fluid-flow sensing is shown in FIG. 30A through FIG. 33B. This embodiment also provides for fluid-initiated feedback without the introduction of fluid into either the urethra, bladder neck, or bladder by providing for a two-way fluid flow from the insertion tool 350 through the urethral apparatus 300D and back to the insertion tool 350. In this embodiment, the sensing component is shown generally at 312D. Like the other embodiments of the fluid-flow configurations, the fluid, which is under pressure in the first fluid reservoir 353a that is contained within the insertion tool 350, flows through the shaft 354 and into the urethral apparatus 300D. In this embodiment, however, fluid is allowed to flow through an input passageway 311Da of the urethral apparatus 300D and return through a return passageway 311Db. The input passageway 311Da and the return passageway 311Db are interconnected (as illustrated in FIG. 32) distal to a depressible contactor 329D, allowing for fluid flow in the fluid circuit when a depressible contactor 329D is open, but preventing fluid flow in the circuit when the depressible contactor 329D is depressed. The depressible contactor 329D is located on the surface of the urethral apparatus 300D and is responsive to the physical contact of the urethra. The depressible contactor 329D serves to restrict the flow of fluid within the fluid circuit by preventing the return flow while the insertion tool 350 and apparatus 300D are being inserted through the urethra.

When the portion of apparatus 300D containing the depressible contactor 329D enters either the bladder neck or the bladder, the depressible contactor 329D is free to move outward, (FIG. 30B) thus allowing the fluid within the fluid circuit to return through the return passageway 311Db and collect in a second fluid reservoir 353b in the insertion tool 350. This change in fluid pressure causes the pressure-responsive, normally closed membrane switch 376 to return to the unengaged position, thus completing a circuit between contacts 377a and 377b and energizing the input contact 389 and the light 366. The system electronics function similarly to the first three fluid-flow configurations.

IV. Embodiments with Electrical Resistance Sensing

Referring to FIG. 34, there is shown an embodiment of a urethral apparatus 400 that uses electrical resistance measurement for position sensing. In this embodiment, the sensing component is shown generally at 412. The electrical resistance between two spaced-apart locations along the urethra will differ from the resistance across the same distance within an aqueous fluid such as urine. For this reason, the embodiment of the urethral apparatus 400 includes two, spaced electrical contacts (a first contact 428a and a second contact 428b positioned along the body 401 thereof. These electrical contacts allow for the passage of a minute current between them as apparatus 400 is installed. The urethra itself allows an electrical conduction as the apparatus 400 is fed through the urethra. When the electrical contacts 428a and 428b reach the or bladder, the electrical resistance between the contacts changes as the apparatus 400 enters a pool of urine in the bladder neck or bladder. This change may be detected electronically with relatively simple analog or digital circuitry and thus activate a feedback signal.

Figure 35A:
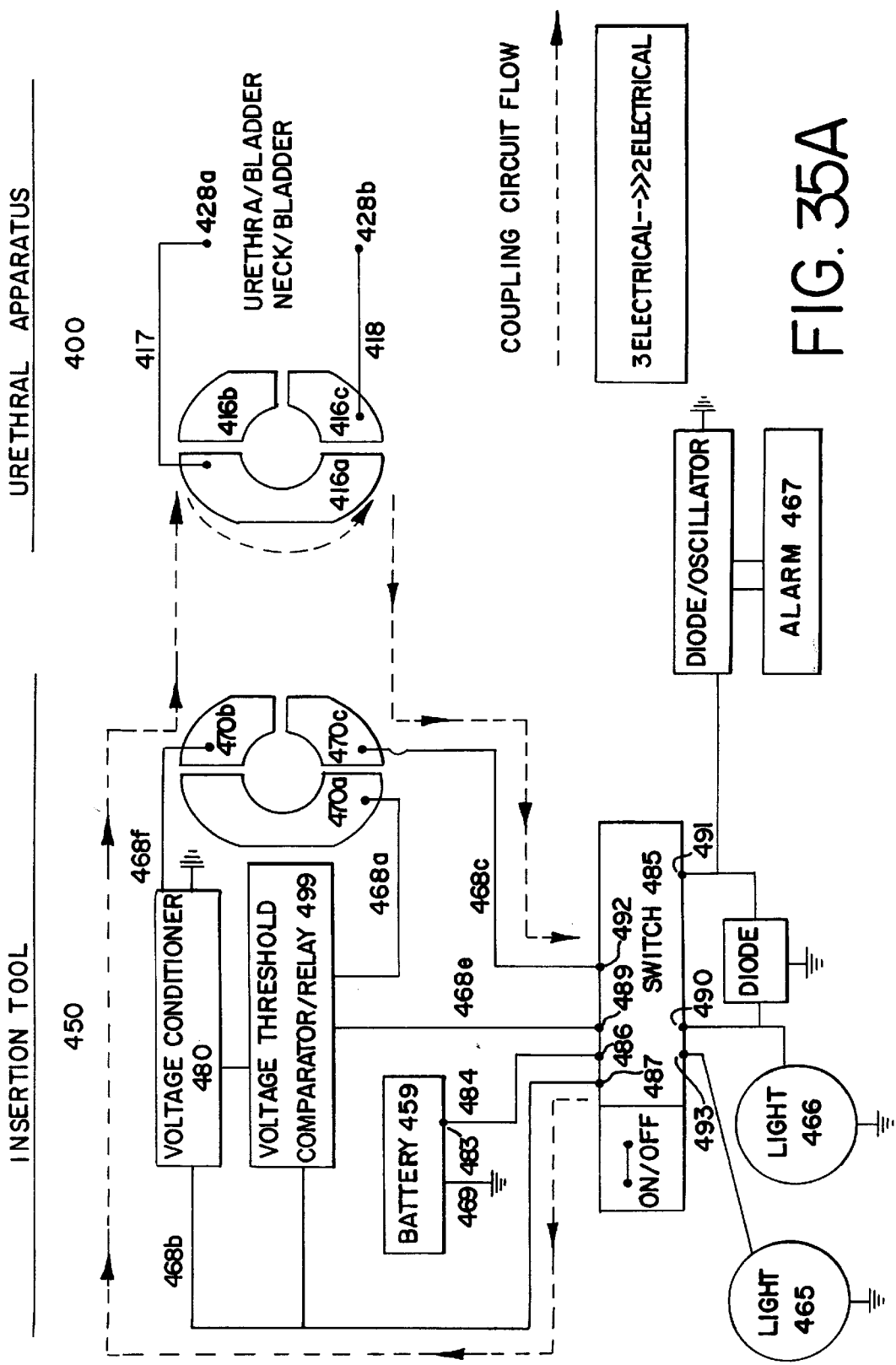
FIG. 35A is a schematic flow diagram illustrating the electrical flow during coupling of the insertion tool and urethral apparatus of FIG. 34.
Figure 35B:
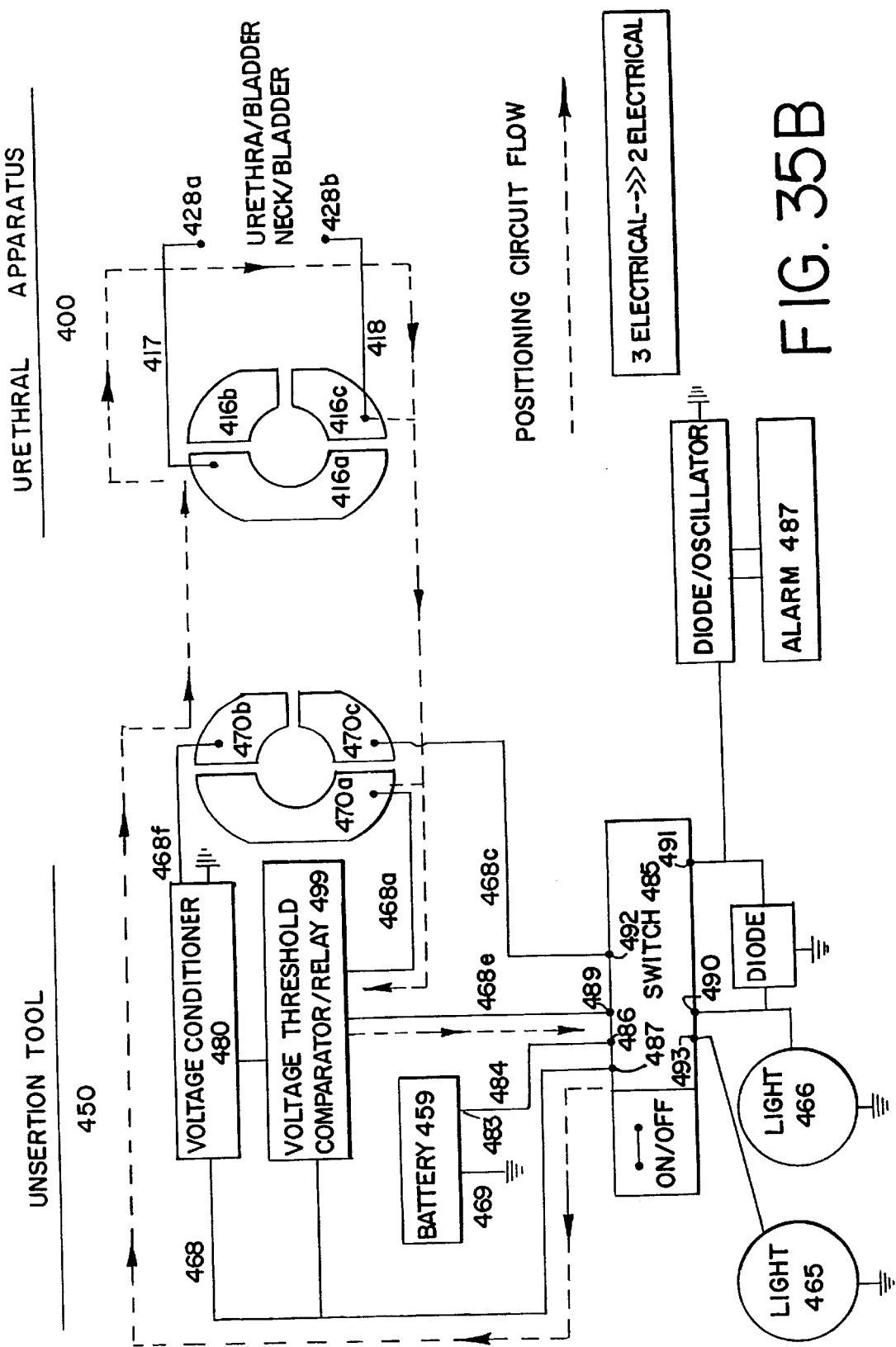
FIG. 35B is a schematic flow diagram illustrating the electrical flow during positioning of the insertion tool and urethral apparatus of FIG. 34.
Figure 36:
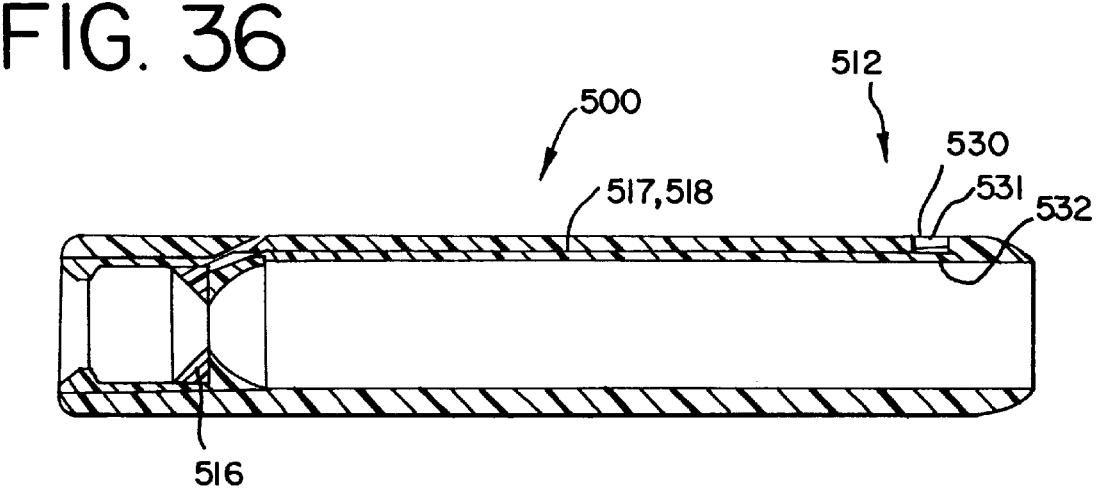
FIG. 36 is a sectional view of an alternate embodiment of a urethral apparatus that uses thermoelectric cooling to provide for position feedback
Figure 37:
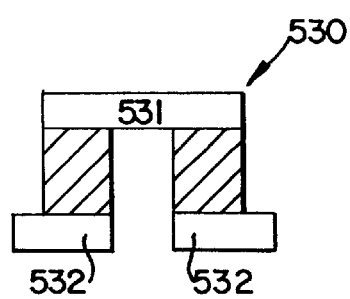
FIG. 37 is an expanded side view of the semiconductor used in the sensing component of FIG. 36.
Figure 39:
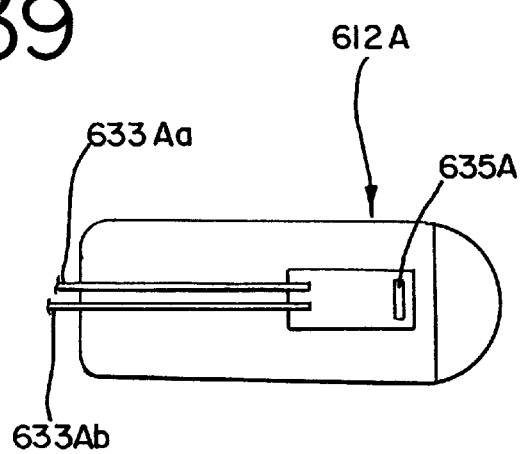
FIG. 39 is an expanded partial top view of an alternate embodiment of a urethral apparatus that uses fiber optics to provide for position feedback

FIGS. 35A is a circuit flow diagram showing the current flows during coupling for this embodiment and aid to further explain the embodiment. FIG. 34B is circuit flow diagram showing the current flows during positioning. The current flows from a battery 459, through a positive lead 484, to a switch 485 in the insertion tool 450, then through a lead 468b to a voltage conditioner 480, which provides the correct voltage. The current flows through an electrical lead 468f, through the contact collars 470 and 416, and through an electrical lead 417 in the urethral apparatus 400 to a first contact 428a on or near the surface 403 of the body 401 of the urethral apparatus. The current is then conducted across the conductive media of the urethra or urine to a second contact 428b, through an electrical lead 418, through the contact collars 416 and 470, and back through the electrical lead 468a in the insertion tool 450 to a voltage threshold comparator and relay 499. When the portion of apparatus 400 that contains the first contact 428a and second contact 428b enters the bladder neck or bladder and is situated in a pool of urine as described above, the change in electrical resistance is detected by the voltage threshold comparator and relay 499 due to the resultant change in voltage. The voltage threshold comparator and relay 499 then compares this voltage with the predetermined, preset voltage. When the voltage value correlates with the preset range, the voltage threshold comparator and relay 499 energizes the input contact 489 through the lead 468e with the line voltage from the battery 459. Depending on the position of the switch 485, either the light only, or the light and alarm gives an indication that the urethral apparatus 400 has entered the bladder neck or bladder as previously described in other embodiments.

V. Embodiments with Thermoelectric Sensing

Referring to FIGS. 36 through 38B, there is shown an alternative embodiment of a urethral apparatus 500 that uses thermoelectric cooling to provide for position feedback. The position of the urethral apparatus in the urinary tract is ascertained in response to feedback from the conduction of current through a thermoelectric module. In this embodiment, the sensing component is shown generally at 512. The thermoelectric module typically is composed of one or more pairs (couples) of semiconductors of Bismuth Telluride that has been negatively or positively doped. The pairs of semiconductor are in a thermally parallel circuit and in an electrical serial circuit. When a low-voltage, direct current is applied to the semiconductor pairs, heat energy is absorbed to one surface, which causes it to become cool, and heat energy is conducted through the semiconductor electrically to the opposite surface, which becomes thermally elevated in temperature causing a liberation of heat to that environment. For this reason the thermoelectric heat transfer effectively performs the function of transferring heat from a donor surface to a receptacle surface. The rate of heat transfer is determined by the semiconductor characteristics as well as the electrical power being transferred through the semiconductor pairs. Given a constant direct voltage, the current increases when more heat is being transferred, and the current decreases when less heat is being transferred between the surfaces.

The Peltier-effect cooling method uses the two junctions of a semiconductor 530 (FIG. 37) which are heat-transfer activity cells in a manner such that a first junction 531 is in contact with the fluid or tissue adjacent to it which transmits heat energy from the urethra to a second heat junction 532 within the body 501. This transmitted heat is quickly reabsorbed by the body 501 and surrounding tissue or fluid surrounding the body 501. Similar to the electrical resistance embodiment above, a voltage threshold comparator and relay 599 then compares this current with the predetermined, preset current. When a change in the rate of heat transfer occurs (dQ/dt=change in heat flow/change in time), it provides an electrical indication that the emergence into the bladder neck or bladder from the urethra (or withdrawal therefrom) has occurred because the thermal conductivity differs when the apparatus 500 is in the urethra or is in the bladder neck or bladder. Electrical circuitry controlling the current flow through the apparatus 500 then generates an appropriate feedback signal as explained below. The emergence into the bladder neck or bladder, which normally contains some residual of fluid, provides for a difference in heat transfer to or from the urethra.

The semiconductor 530 has a thin construction of an overall dimension of approximately 0.008 inch in thickness with width dimensions of 0.020 inch and 0.040 inch. On each of the heat transfer surfaces, a gold or platinum conductive layer is applied using vapor deposition. Alternatively a 0.0008 conductive film may be adhered to the surface 503 of the body 501 using conductive epoxy adhesive. The foil assists in the transfer of heat and provides a noble and biocompatible surface for interface with the surrounding environment. The dimensions of semiconductor 530 determine the ability to transfer heat from the lower temperature junction to the higher temperature junction. In this application the useful determinate indicator of position is derived from the change in power which is used to transfer the heat rather than a measurement of the heat transfer. The power changes as the surrounding environment changes when the first junction 531 of the semiconductor 530 enters the bladder neck or bladder from the urethra.

Figure 38B:
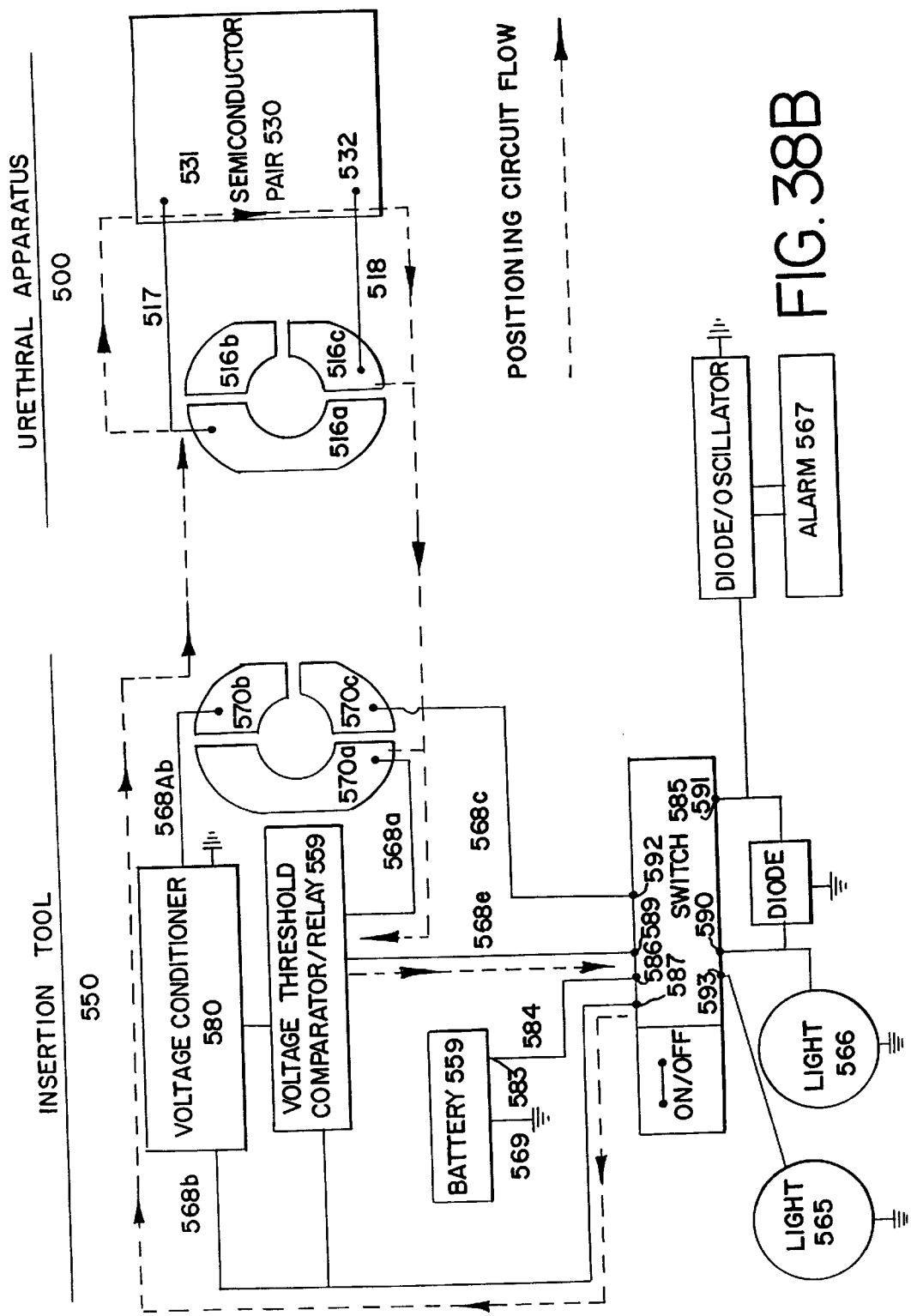
FIG. 38B is a schematic flow diagram illustrating the electrical flow during positioning of the insertion tool and urethral apparatus of FIG. 36.
Figure 40:
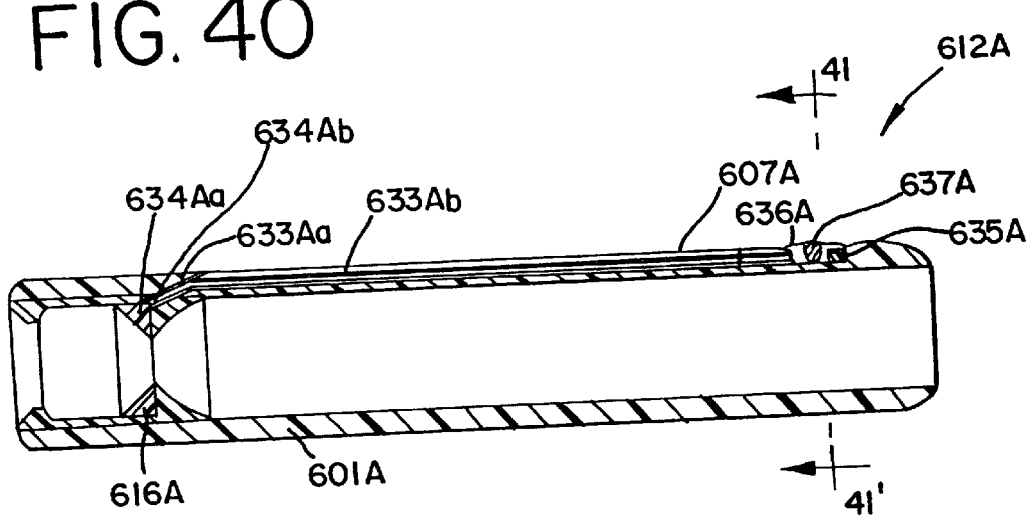
FIG. 40 is a side view of the urethral apparatus of FIG. 39 at one stage of positioning, showing the fiber optic light being block or absorbed.
Figure 41:
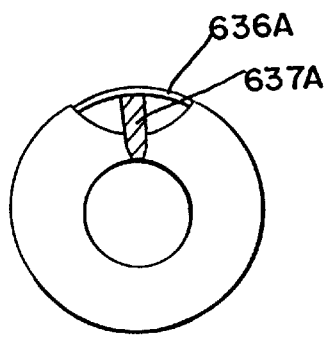
FIG. 41 is a cross-sectional view of the urethral apparatus of FIG. 40 taken along line 41–41'.

FIGS. 38A is a circuit flow diagram showing the current flows during coupling for this embodiment and aids to further explain the embodiment, FIG. 38B is a circuit flow diagram shows the current flows during positioning. Low-voltage, direct current flows from a battery 559 through a positive lead 584 to the switch 585 and then through a lead 568b and is conditioned by a voltage conditioner 580, which provides the desired voltage and current limits. The current flows then through a lead 568Ab, through a contact collar 570 of the insertion tool 550 and a contact collar 516 of the apparatus 500, and through the electrical lead 517 to the semiconductor 530. The current passes through the semiconductor junctions 531 and 532 and is conducted back through the electrical lead 518, through the contact collars 516 and 570, and through the second electrical lead 568a in the insertion tool 550 to the voltage threshold comparator and relay 599. When the insertion tool 550 and apparatus 500 enter the bladder neck or bladder, the change in environment causes the first junction 531 to absorb a different amount of heat, thereby causing a resultant change in current. The voltage threshold comparator and relay 599 then compares this current with the predetermined, preset current. When the current value exceeds the preset level, the voltage threshold comparator and the relay 599 energizes the input contact 589 through the lead 568e with line voltage from the battery 559. Depending on the position of the switch 585, either the light only, or the light and alarm give an indication that the apparatus 500 has entered the bladder neck or bladder as previously described in other embodiments.

VI. Embodiments with Fiber Optic Sensing

FIGS. 39 through 45B show alternative embodiments of urethral apparatus 600A and 600B that use fiber optics for position sensing. In these embodiments, the fiber optics are incorporated into the urethral apparatus to initiate a feedback signal that the apparatus is properly positioned. In this embodiment, the sensing component are shown generally at 612A and 612B, respectively. The embodiment 600A shown in FIGS. 39 through 44B includes two fiber optic strands that provide for signal transmission and return. The fiber optic strands are composed of a central core of diameter of approximately 8 to 10 micron with a total clad or unclad diameter of approximately 125 micron (or approximately 0.005 inch).

Figure 44A:
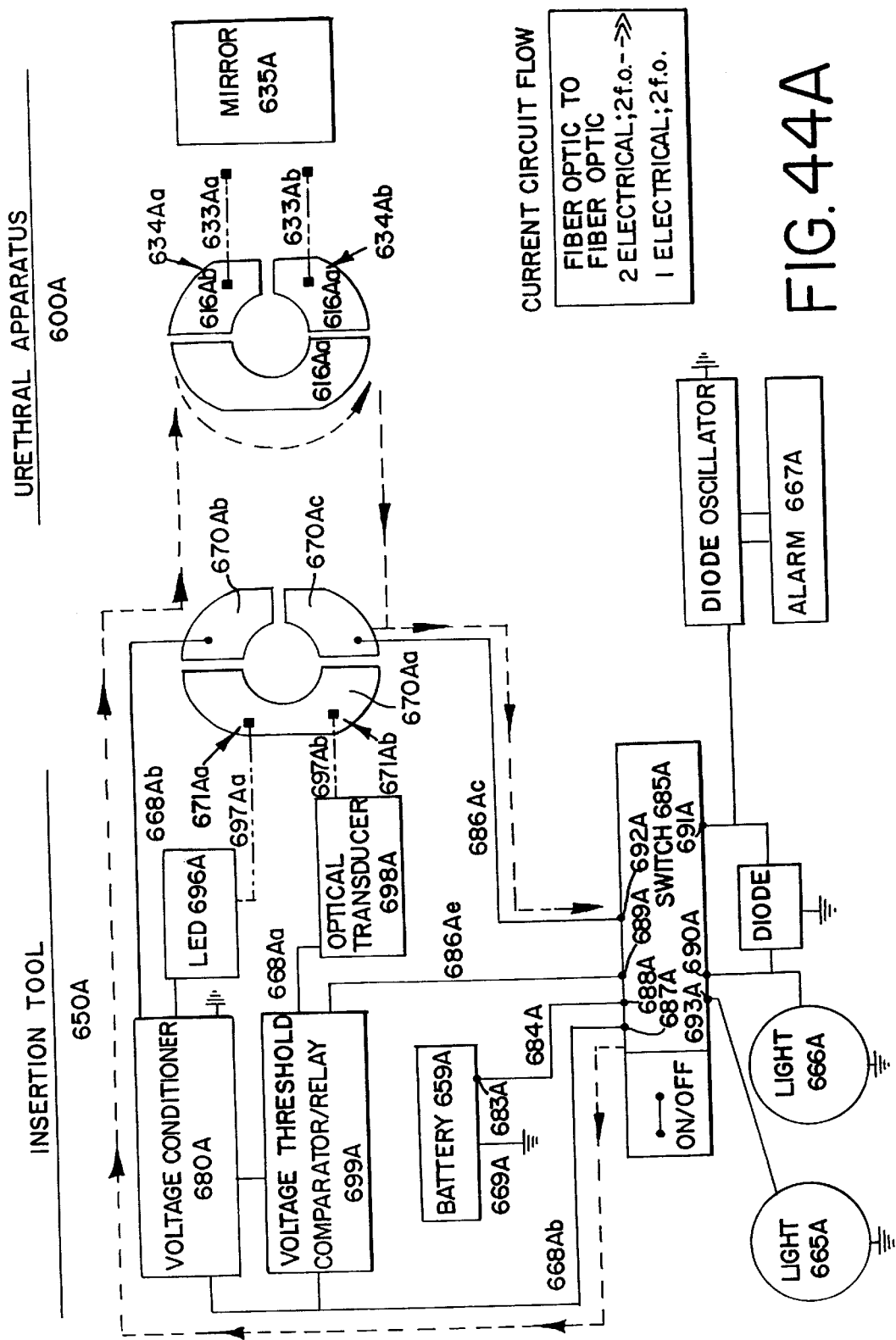
FIG. 44A is a schematic flow diagram illustrating the electrical flow during coupling of the insertion tool and urethral apparatus of FIG. 39.
Figure 44B:
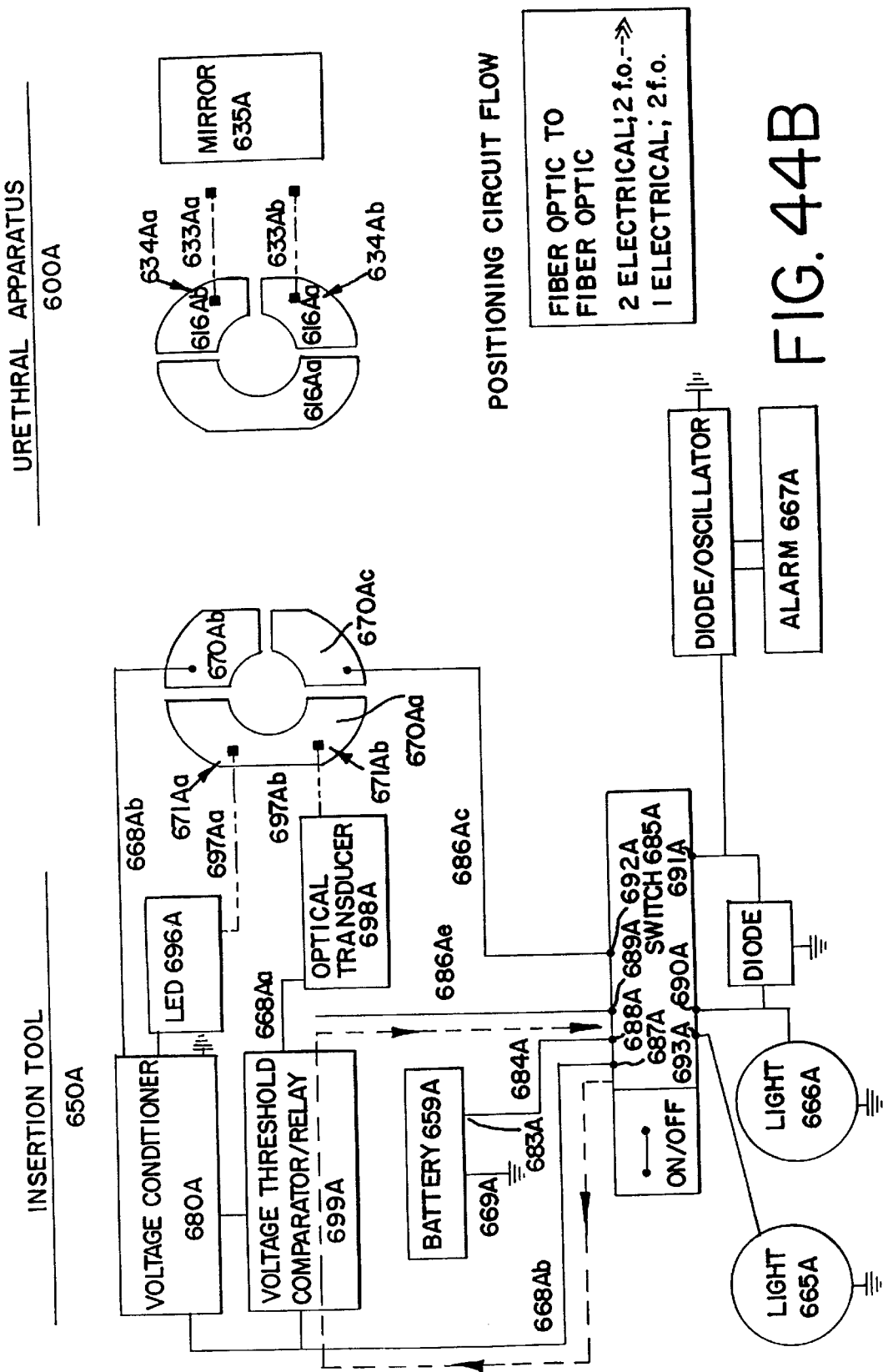
FIG. 44B is a schematic flow diagram illustrating the electrical flow during positioning of the insertion tool and urethral apparatus of FIG. 39.

Referring to FIGS. 44A and 44B, current flows from a battery 659A to a switch 685A, then through a lead 668Ab to a voltage conditioner 680A, which provides the correct voltage and current to an LED696A. A low-energy light wave preferably in the visible light spectrum wavelengths of 400–750 nanometers is transmitted by a bulb or light-emitting diode (LED) 696A or bulb into the first insertion tool fiber optic strand 697Aa to the insertion tool contact collar 670A and terminates there within the strand casing at a mating contact point 671Aa, which may be a similar glass fused contact mounted within the contact collar 670A or a dissimilar material that has been bonded around the perimeter, which in turn is bonded into the insertion tool contact collar 670A.

A first apparatus fiber optic strand 633Aa (FIG. 40) terminates in like manner at a mating contact point 634Aa of an apparatus first contact collar 616A and extends within the body 601A to a location at a proximal portion 607A. A second apparatus fiber optic strand 633Ab lies alongside the first apparatus fiber optic strand 633Aa and is coupled in like manner at a mating contact point 634Ab of the apparatus first contact collar 616A. Facing the terminal ends of the first and second apparatus fiber optic strands 633Aa and 633Ab is a mirror 635A, which reflects light emitting from the first apparatus fiber optic strand 633Aa into the second apparatus fiber optic strand 633Ab. Similarly, a second insertion tool fiber optic strand 697Ab lies alongside the first insertion tool fiber optic strand 697Aa and terminates in a handpiece housing 651A and contact collar 670A at a mating contact point 671Ab.

Figure 43:
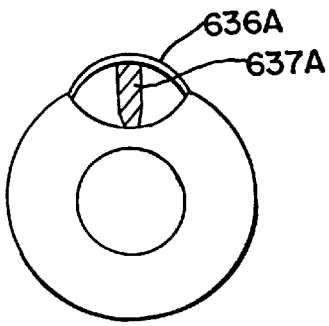
FIG. 43 is a cross-sectional view of the urethral apparatus of FIG. 42 taken along line 43–43'.
Figure 42:
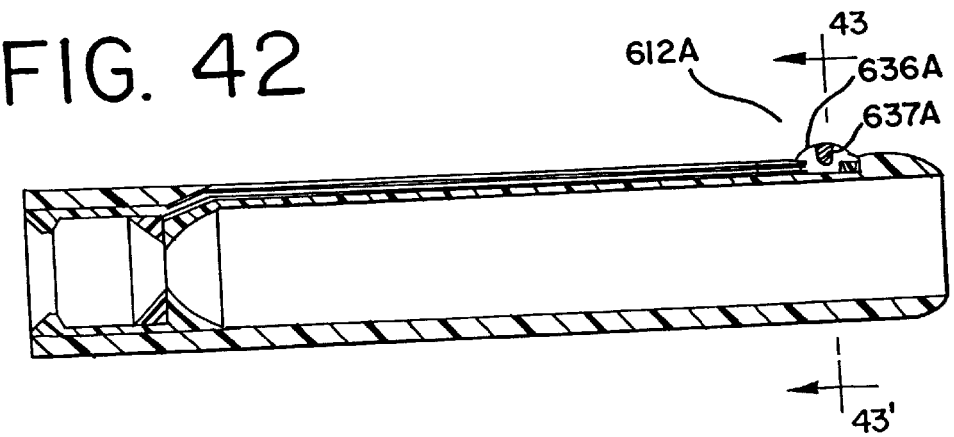
FIG. 42 is a view similar to FIG. 40 showing the urethral apparatus at another stage of positioning and showing the fiber optic light being reflected.

An additional feature of this embodiment is the use of a shape-memory, nonreflective member 636A (FIGS. 40 and 41) that is interposed between the terminal ends of the first and second apparatus fiber optic strands 633Aa and 633Ab and the mirror 635A during insertion of the coupled insertion tool 650A and urethral apparatus 600A, thus, effectively preventing light from being returned through the second apparatus fiber optic strand 633Ab. When the portion of the apparatus 600A containing the nonreflective member 636A enters the bladder neck or bladder, the shape-memory characteristics of the nonreflective member 636A cause it to move outward and therefore allow the light circuit to be completed (FIGS. 42 and 43). The nonreflective member 636A optionally has an additional leaf 637A to ensure complete blockage of the light circuit between the terminal ends of the apparatus fiber optic strands 633Aa and 633Ab and the mirror 635A. Alternately, deformation can take place in response to internal pressure from self-contained fluid in a reservoir adjacent the nonreflective member 636A. Alternately, the reflective and absorptive properties of the leaf 637A and the mirror 635A could be reversed in such a manner that the light from the fiber optic strands is reflected by the leaf 637A and the mirror 635 is replaced by a nonreflective surface.

As the urethral apparatus 600A enters the bladder neck or bladder, the shape-memory characteristics (or, alternately, fluid pressure) cause the nonreflective member 636A to move outward and thereby allow the light circuit to be completed (see FIG. 44b). As the light is returned to the second insertion tool optic fiber strand 697Ab and is incident upon the optical transducer 698A, the light energy is converted into an electrical signal, which is carried by the lead 668Aa to a voltage threshold comparator and relay 699A. The voltage threshold comparator and relay 699A then compares this voltage with the predetermined, preset voltage. When the voltage value exceeds the preset level, the voltage threshold comparator and relay 699A energizes an input contact 689A through the lead 668Ae with line voltage from the battery 659A. Depending on the position of the switch 685A, either the light only, or the light and alarm give an indication that the apparatus 600A has entered the bladder neck or bladder as previously described in other embodiments.

Figure 45A:
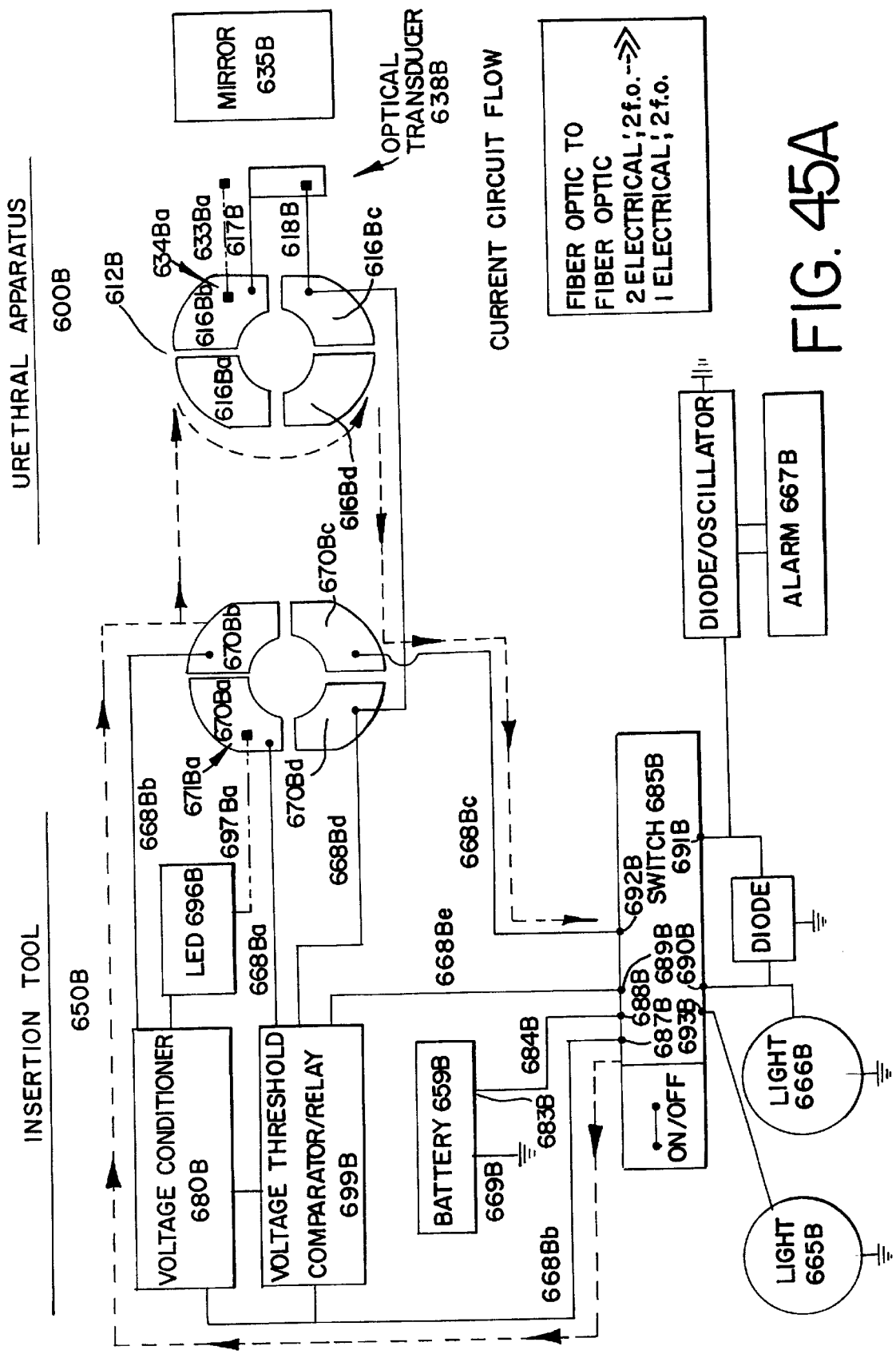
FIG. 45A is a schematic flow diagram illustrating the electrical flow during coupling of the insertion tool and an alternative embodiment of a urethral apparatus that uses only one fiber optic strand and an optical transducer.

In an alternative embodiment shown in FIGS. 45A and 45B, the urethral apparatus 600B has only one fiber optic strand 633Ba and has an optical transducer 638B located in the distal portion 605B of the body 601B with an electrical lead 618B leading from the optical transducer 638B to a conducting surface 616Bc. Current then flows to a contact 670Bd of the insertion tool 650B and to a voltage threshold comparator and relay 699B through the lead 668Bd. When the current value exceeds the preset level, the voltage threshold comparator and relay 699B energizes the input contact 689B through the lead 668Be with line voltage from the battery 659B. Depending on the position of switch 685B, either the light only, or the light and alarm give an indication that the urethral apparatus 600B has entered the bladder neck or bladder as previously described in other embodiments.

Optionally, the mirror 635A (or 635B) may be eliminated in either of the configurations shown in FIGS. 44A and 44B (or 45A and 45B) by orienting the two ends of the fiber optic strands 633Aa and 633Ab (or optionally, first fiber optic strand 633Ba and optical transducer 638B) at a spaced distance across from each other with the non-reflective shape-memory member 636A (or 636B) interposed between the two elements. Similar circuitry to that described above would be employed.

In an alternate embodiment using fiber optics, position sensing can be derived from the reflection of light from the urethral surface. Such reflection is dependent upon the incidence of the surface and the distance to the surface on which the light is imparted. It is not necessary to visualize details of the internal surface of the urethra in order to detect the position of the apparatus within the urethra. Instead, it is important to be able to macroscopically characterize the environment and identify when the environment changes from that of the urethral surface to the urine occupying the bladder neck or bladder.

Use of fiber optics to derive position sensing from intraurethral reflection is provided by incorporating one or more fiber optic strands in two locations along the body of the urethral apparatus or the insertion tool. A first strand illuminates the area to be evaluated. The second strand conducts a surface illumination from the illuminated surface to the insertion tool. Alternately, a first strand illuminates the area to be evaluated, and a photovoltaic cell is used to receive the incidence light and generate an electric voltage that produces a current that is conducted to the indicator unit. There is much information available from this returned illumination; however, little or nothing more is needed than the intensity of the returned signal. This output voltage may then be used to indicate the change in reflection that occurs as the apparatus enters the bladder neck or bladder. This change may be electronically detected, and the caregiver who is inserting the urethral apparatus is thereby alerted.

VII. Advantages of the Disclosed Embodiments

Advantages of the embodiments disclosed herein include ease of use and low cost while providing one critical piece of information—proper positioning. These advantages obviate the need for more expensive equipment or expensive professional medical skills, which would otherwise be necessary to obtain information about the relative position of the urethral apparatus. The disclosed embodiments provide an indication of a change sensed when the sensing component of the urethral apparatus makes the transition from the urethra into the bladder, or more preferably, the bladder neck. The sensing component preferably is not used to obtain any specific measurements, such as urethral pressure profiles and so on. The sensing component responds to a one-time change that results in a signal being emitted to the person, such as the caregiver or even the patient. That signal can be audible, visual, tactile, or any other type of signal that informs the caregiver or patient of the change in the conditions or features surrounding the urethral apparatus as it enters the bladder neck or bladder.

VIII. Further Alternative Embodiments

There are additional alternate embodiments that can be made without departing from the scope and the spirit of the inventive subject matter.

In some of the embodiments described above that use electrical sensing, the sensing component includes a structure (e.g., 123 in FIG. 5) having shape-memory characteristics. Such structure can assume any number of alternate shapes, configurations, or characteristics. For example, the sensing component can be a movable or mechanical structure in the shape of flexible fingers or wings, or can be an electromechanical structure, a pneumatic or hydraulic member, a light-emitting-and-receiving member, an electronic member, a heat-transfer member, or any other type of component or structure that detects a change of the component from a first status to a second status.

It will be appreciated that other mechanisms for sensing a change in the environmental conditions, features, or parameters proximate the urethral apparatus when it passes out of the urethra and into the bladder or the bladder neck fall within the scope and spirit of the disclosed inventive subject matter. The embodiment disclosed herein should not be construed to include all permutations, but instead provide an indication of some of the permutations that are possible. Some of these alternate embodiments are detailed below.

Still other embodiments may incorporate the sensing component as part of the insertion tool. Such embodiments may be adapted to any of the insertion tool embodiments (150, 250, 350, 450, 550, and 650, described above). A purpose of the sensing component 112 is to initiate a feedback chain to indicate the position of the body of the urethral apparatus based upon a change in an environmental condition, feature, or parameter as the proximal portion (e.g., 107 in FIG. 1) or proximal end (e.g., 108 in FIG. 1) of the body of the urethral apparatus passes at least partially out of the urethra and into the bladder or bladder neck. Since the length of the body 101 of the urethral apparatus may be varied, the sensor component can be part of the insertion tool in some alternative embodiments. For example, in an embodiment that uses an optical transducer for position sensing (e.g., FIGS. 39 through 44B), the optical transducer may be included in the proximal end of the insertion tool (e.g., 650A) with fiber optics either on the insertion tool itself or on the body of the urethra apparatus.

Although many of these embodiments teach the placement of the sensing component 112 at or near the proximal end of the body of the urethral apparatus, the sensing component 112 may be located at the distal end or distal portion and still provide an indication of the proper placement of the urethral apparatus in relation to the bladder neck or bladder.

A. DRUG DELIVERY EMBODIMENTS

Figure 46A:
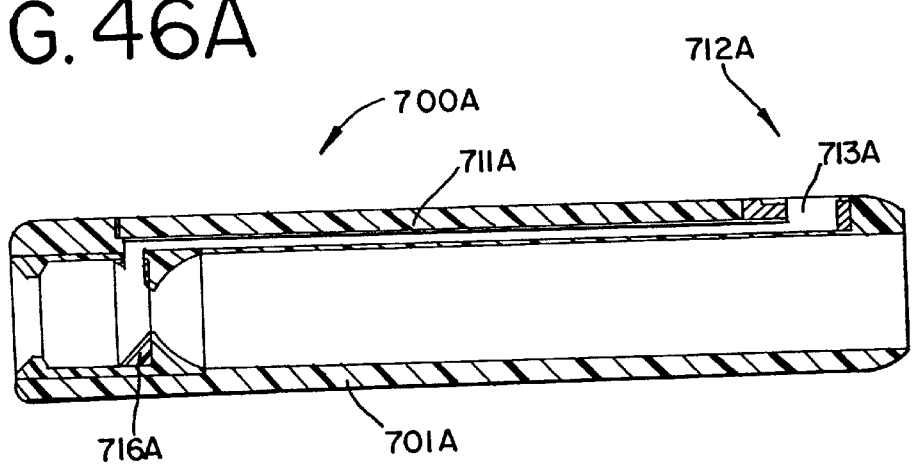
FIG. 46A is a sectional view of an alternate embodiment of a urethral apparatus that incorporates drug delivery.
Figure 46B:
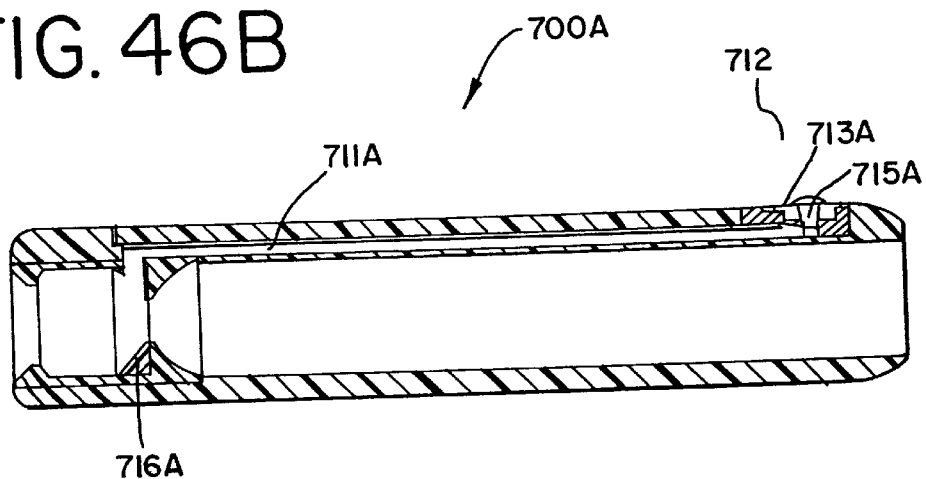
FIG. 46B is sectional view of an alternate embodiment of the urethral apparatus shown in FIG. 46A with a flow-restrictor valve.

Referring to FIGS. 46A and 46B, an embodiment of a urethral apparatus 700A is disclosed. The embodiment 700A provides for drug delivery. For the sake of clarity in the drawings, the sensing component 712A is not illustrated in FIG. 46A or 46B but is considered to be a part of the embodiment described. The body 701A incorporates one or more fluid ports 713A with an optional one-way flow-restrictor valve 715A (FIG. 46*b*) in communication with one or more fluid passageways 711A that pass through the body 701A and that are in communication with corresponding fluid lumens (not shown) in an insertion tool. The insertion tool may be similar to any of the insertion tool embodiments disclosed above.

Figure 47:
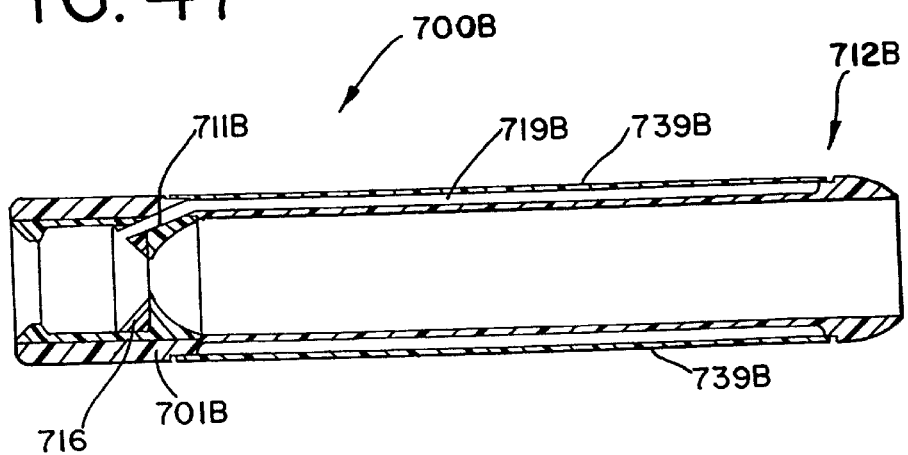
FIG. 47 is a sectional view of another alternate embodiment of a urethral apparatus that incorporates drug delivery.

In an alternative embodiment of the urethral apparatus 700B shown in FIG. 47, the body 701B incorporates a porous or microporous membrane 739B in communication with a fluid lumen 711B (or alternately, a reservoir 719B) in the body 701B. The membrane 739B can extend around part or all of the circumference of body 701B. These ports or membranes are used to introduce drugs, agents, genes, monoclonal antibodies, or other materials either passively or actively, for example, using diffusion, osmosis, iontophoresis, electrophoresis, photodynamic methods, pressure, ultrasound, or other driving or activating forces. Those skilled in the art will recognize that some of these drug-delivery embodiments require the addition of drug reservoirs, electrodes, transducers, or other components necessary to the technology.

In other embodiments the alternate fluid ports or membranes are located in a position along the periphery of the body so that drugs or agents are introduced to the prostate, for example. Similarly, a portion of the alternate body may itself contain drugs or other agents impregnated in a polymer, for example, for a controlled- or time-released therapy. Such drugs could, for example, be an antibiotic agent of oligodynamic metal to counter or modify bacterial growth in the urethra, bladder neck, or bladder.

B. VALVED URETHRAL APPARATUS EMBODIMENT

Referring to FIGS. 48 through 54, there is disclosed another embodiment of a urethral apparatus 800. This embodiment includes a body 801 that incorporates a valving mechanism, such as a magnetic valve 839. (For the sake of clarity in the drawings, the sensing component is not included in the drawings but is considered to be a part of the embodiment described. It will be appreciated that any of the embodiments of the urethral apparatus having position sensing can further incorporate a valve in any manner or iteration possible.) This first valving embodiment uses magnetics and stored energy to control the flow of urine and to dampen pressure impulses arising from momentary, and often sharp, increases in bladder pressure as a result of exercise, coughs, laughing, or other sudden or strenuous responses or reflexes.

Figure 48:
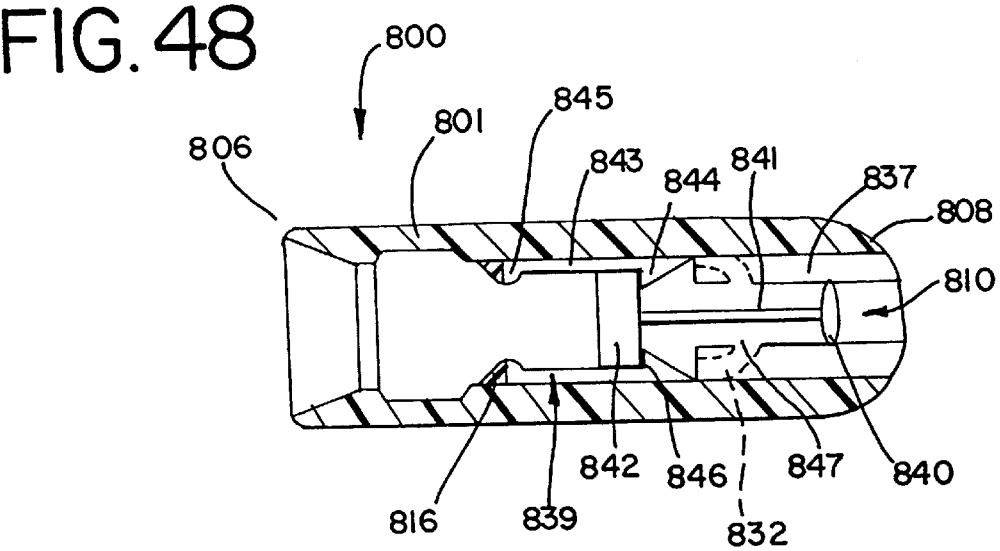
FIG. 48 is a sectional view of an alternate embodiment of a urethral apparatus that incorporates internal valving for fluid flow control and shown in a first, closed stage of operation.
Figure 49:
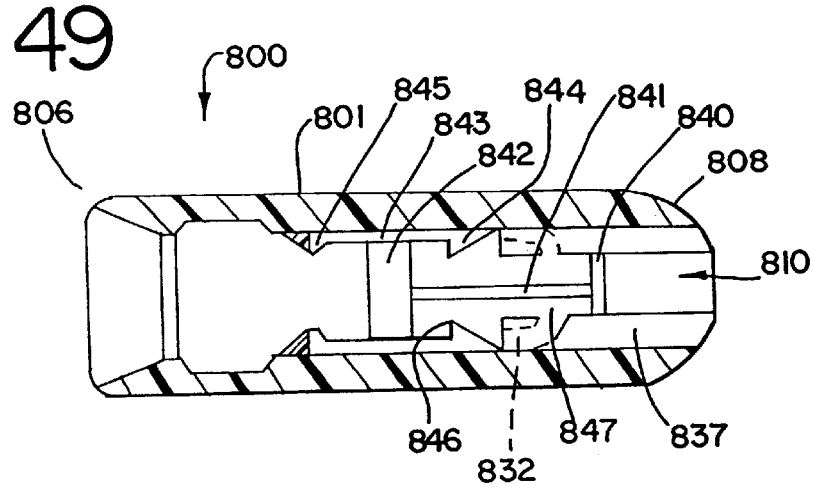
FIG. 49 is a sectional view of the embodiment of FIG. 48 showing the valving components in a second, damping stage of operation.

FIG. 48 shows the magnetic valve 839 in a closed position. The body 801 has an open proximal end 808 that extends into the bladder neck or bladder and comprises a fluid-flow director 837 with a lumen 810. Within the lumen 810, a seal 840 is slidable such that it provides for a fluid-tight seal to prevent leakage of urine through the body 801 of the urethral apparatus when the valve is in a closed position (see for example FIG. 48) or dampened position (see for example FIG. 49) but allows fluid to flow through the body 801 in the open position (see for example FIGS. 50 and 51). Connected distally to the seal 840 is a plunger 841 and a magnet 842. The seal 840, the plunger 841, and the magnet 842 function as a unit to control the flow of urine through the body 801.

The magnet 842 travels axially in a longitudinal direction within a magnetic profiler 843 which has an enlarged proximal end 844, an enlarged distal end 845, and a stop 846, which serves to limit travel of the magnet proximally within the magnetic profiler. As shown in FIGS. 48, 52, and 53, the fluid-flow director 837 has one or more openings 847 that communicate with passageways 832 to allow urine flow. Openings 847 are located distal of the seal 840 when the magnet 842 is positioned in a closed position or is in a damping position. The magnet 842 is shaped to allow urine to flow around its periphery (FIGS. 54A and 54B) and out through the distal end 806 of body 801.

Figure 50:
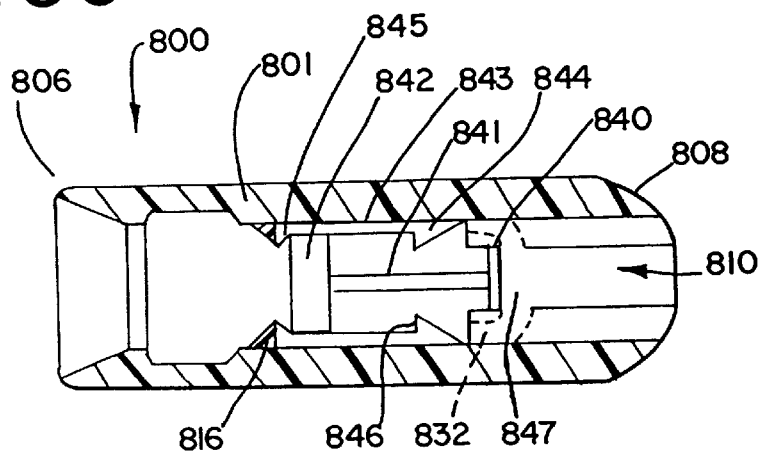
FIG. 50 is a sectional view of the embodiment of FIG. 48 showing the valving components in a third, open stage of operation.

The proximal end 844 and optionally the distal end 845 of the magnetic profiler 843 are made of a material that interacts with the magnet 842 to controllably influence the travel of the magnet 842 in a longitudinal direction. When the magnet 842 is in a closed position (FIG. 48), a magnetic circuit is formed between the magnet 842 and proximal end 844. When bladder pressure is increased above a critical pressure, the force of urine against the seal 840 causes the magnet 842 to move away from the stop 846 in a distal direction. As the magnet 842 moves distally through the magnetic profiler 843, magnetic forces may optionally be exerted by the distal end 845 to interact with the magnet 842 and assist in moving the magnet 842 distally. As bladder pressure is increased to a greater degree, the magnet 842 is physically pushed toward the distal end 845. The seal 840 then moves distally beyond the openings 847 and allows urine to flow distally through the body 801 (FIG. 50). As the urine flow is diminished and pressure is decreased on the seal 840, the magnet 842 is drawn proximally toward the stop 846 by the magnetic forces existing between the magnet 842 and the proximal end 844. The magnetic circuit is again completed between the magnet 842 and the proximal end 844 to hold the valve in a closed position. If the distal end 845 is also constructed of a material that interacts magnetically with the magnet 842, the force of the magnetic flux or circuit between the magnet 842 and the proximal end 844 is greater than the force of the magnetic flux or circuit between the magnet 842 and the distal end 845, thus allowing the magnet 842 to always return to a closed position. Alternately, a member that interacts with the magnet 842 could be located in a position distal to the distal end 845.

If the user experiences a momentary impulse in bladder pressure due to exercise, coughing, or laughing, for example, the seal 840 experiences very high, but very temporal, pressures. The magnetic field formed between the magnet 842 and the proximal end 844 absorbs the energy exerted upon them by the controlled displacement of the plunger 841 and the magnet 842 as the plunger is displaced along the axis of the fluid flow director 837. This displacement provides for energy being stored in the magnetic circuit, which is subsequently returned in the form of work over time as the plunger is repositioned during the pressure impulse and returns to a seated, closed position after the impulse. During this displacement, the seal is moved distally but not far enough distally to permit urine flow through the openings 847. Thus, the length of the plunger 841 and the magnetic profiler 843 are such that the maximum impulse in bladder pressure does not cause the seal 840 to move distally beyond the openings 847. It is this relationship of work over time that allows the apparatus to absorb pressure impulses that may be many times greater than the pressure needed to actuate the valve using the Credé method described below.

To actuate the valve, the user or caregiver simply uses the Credé method by employing his or her hands to exert pressure over the symphysis pubis. This increases the pressures within the bladder and initiates the sequence of events that opens the valve.

As a fail-safe feature, the magnetic circuit between the magnet 842 and the proximal end 844 is over-ridden at a bladder pressure that is less than the point at which urine refluxes into the kidneys. Alternately, the apparatus 800 can be actuated by inserting a magnet into the urethra with enough force to overcome the force of the magnetic circuit formed between the magnet 842 and the proximal end 844.

C. ANCHORING

After positioning, any of the embodiments of the urethral apparatus can be anchored or secured in the urethra, bladder neck, or bladder. This may be facilitated by purposefully selecting the diameter, size, shape, and other characteristics of the body of the urethral apparatus based on physical characteristics of the urethra, bladder neck, or bladder.

First, anchoring of any of these embodiments may be accomplished by the physical compression of the urethral wall against the body of the urethral apparatus. This is the result of the circumferential pressure instilled upon the body by the urethra. These distributed forces should be sufficient to provide for a longitudinal restriction of movement that exceeds the maximum force instilled upon the projected area of the body by the hydraulic pressure of the urine.

Second, anchoring may also be facilitated by selecting a urethral apparatus body with a cross-sectional area that is appropriate for the individual user. In some embodiments, the projection of the surface area combined with the longitudinal surface area, shape, and texture may be sufficient for mechanical anchoring to offset incident hydraulic or physiologic forces that would otherwise shift or expel the urethral apparatus. Designing the longitudinal axis surface to be cylindrical, ellipsoidal, hyperbolic, sinusoidal, helical, or wedge-shaped, or to have various cross-sectional areas or circumferences along the longitudinal axis (including barb-like projections) is effective in acquiring sufficient anchoring.

Third, anchoring can also be accomplished by the addition of various external features to the exterior of the body or modifications in the material characteristics that comprise the body or exterior. These include, but are not limited to, features such as flexible fingers or wings that unfold in the bladder, variation of surface texture and asperity heights, surface compressibility, length, contour, protrusions, grooves, axial stiffness, geometric patterns, tissue entrapment surfaces such as recesses or pressure points, material frictional characteristics, material uniformity (or alternately non-uniformity), regional rigidity, projected area, and other characteristics. The combination of the urethral system dynamics and of the surface characteristics of the apparatus while in contact with the urethral wall ultimately determine the adequacy of the anchoring of the body of the urethra apparatus. In order for the various embodiments to be effective, controllable anchoring is desirable, if not mandatory, and dependably predictable once the user's urethral environment has been clinically characterized. Any of these anchoring techniques can be enhanced by the use of adhesives. In addition, the proximal and distal ends of the body may have radiused, atraumatic edges.

An embodiment having an anchoring structure is disclosed in FIGS. 55 and 56. A urethral apparatus 900 includes a sinusoidal surface 910a along an external surface 903 of the body 901. External surface 903 has lower surface portions 930a and higher surface portions 932a. These higher surface portions 932 a may have varying degrees of compression, ranging from slightly compressible to very compressible. The offset sinusoidal surface 910b (FIG. 56) may also aid in insertion of the urethral apparatus, since during insertion, the insertion tool and the urethral apparatus are coupled together in a locked position and are capable of being rotated as a unit. The offset sinusoidal surface 910b also has lower surface portions 930b and higher surface portions 932b.

FIG. 57 shows the incident forces and hydraulic urine pressures exerted on the body 901. Pressure is incident upon the projected area 941, which is exposed to urine at the bladder neck 42. The urethra 40 contacts the external surface 903 of body 901 along its length. This pressure is a function of length P(L), and circumference is a function of length C(L); either may be variable along the length. (The nomenclature dL indicates an infinitesimal change in length as used in integration.) FIG. 57 illustrates that each variable contributes to anchoring the urethral apparatus 900 within the urethra.

Anchoring is accomplished by the summation of all the forces between the body 901 and the urethra 40 exceeds the maximum peak forces exerted over time by fluid pressures that contact the projected area 941 of the surface. The forces imparted on body 901 are hydraulic and physiological (e.g., spasm). Hydraulic forces may be high pressure, short-duration impulses caused by laughing or coughing or other sudden stresses on the bladder. The body 901 remains stable when the smaller, hydraulic forces resulting from the urine are imparted on the urethral apparatus over long periods of time. These prolonged hydraulic forces may occur in the use of urethral apparatus 900 with a urine-control feature as in the embodiment of the magnetic valve (FIG. 48) at the time just prior to urine release.

Embodiments of the urethral apparatus body with internal flow-restriction components may be retained in the urethra at the bladder neck or bladder when impulses of pressure peaks upon it range from 4 to 268 inches of water for a time duration of up to 3 seconds, or when the urethral apparatus is subjected to prolonged pressurization ranging from 1 to 60 inches of water for up to 8 hours without displacement. The embodiment of the urethral apparatus body 901 with the higher surface 932a as shown in FIG. 55 can be used with changes in amplitudes ranging from approximately 1 percent to approximately 400 percent of the area as measured to the lower surface 930a. The higher amplitudes and variation of surfaces are useful for greater anchoring requirements.

Figure 58A:
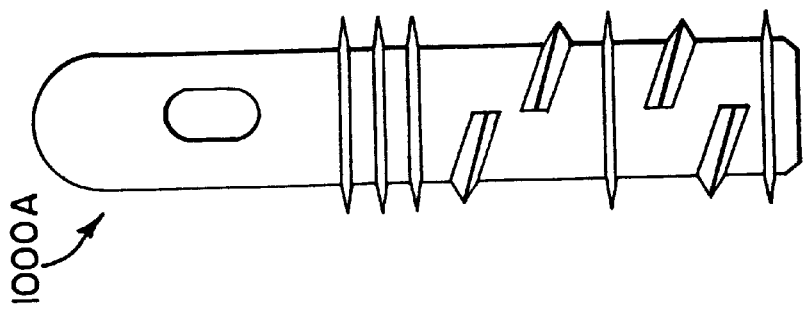
FIGS. 58A, 58B, and 58C show alternative embodiments for females of urethral apparatuses having anchoring structures.
Figure 58B:
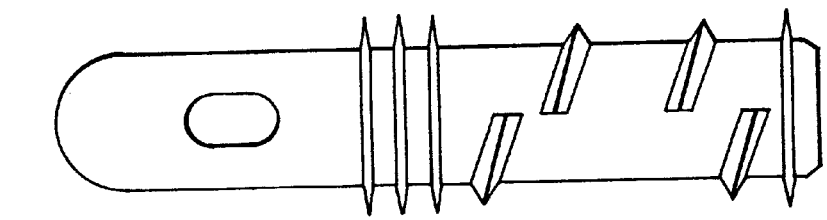
Figure 58C:
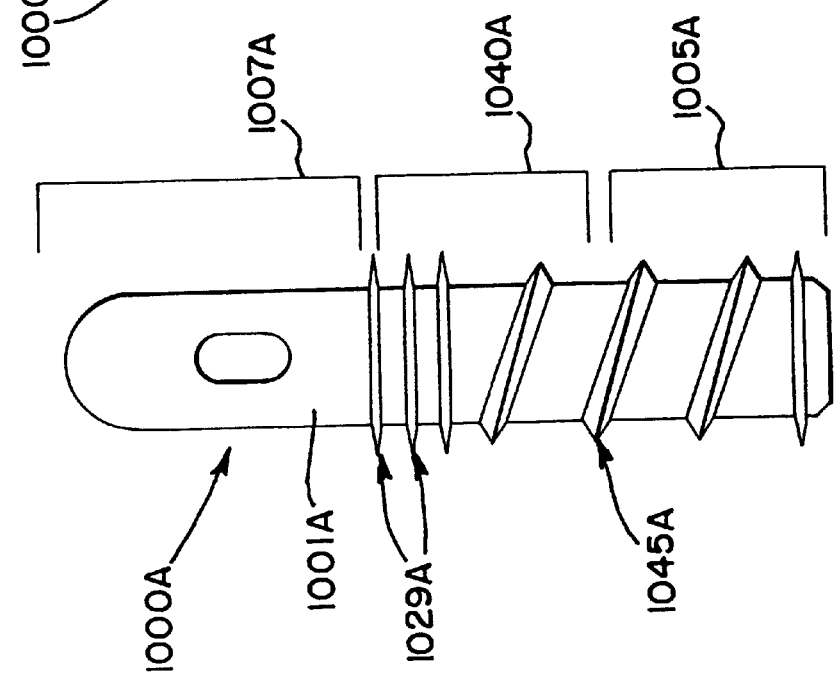

Another alternative structure for anchoring or retaining the urethral apparatus is illustrated in FIGS. 58A–58C and FIGS. 59A–59E. FIGS. 58A–58C illustrate a female version of a urethral apparatus 1000A, and FIG. 59A–59E illustrate a longer, male version 1000B. These embodiments of urethral apparatuses includes external protrusions or anchors 1045A or 1045B. As illustrated, these protrusions 1045A or 1045B may be complete helical ribs or partial helical ribs. These embodiments also include one or more complete circumferential sealer rings 1029A, 1029B located adjacent to or intermixed with these anchors 1045A or 1045B, respectively. The addition of sealer rings 1029A, 1029B aid in preventing urine leakage between the urethral apparatus body 1001 and the urethra. These anchors 1045A, 1045B or sealer rings 1029A, 1029B can vary in height, length, number, compressiveness, axial placement, material characteristics, and helix angle varying from 0 to 300 degrees, and more preferably from 15 to 300 degrees. The maximum amplitude of each anchor may extend along the entire length of a middle portion of the anchor, or may extend along only part of the middle portion of the anchor. These anchors 1045A, 1045B or sealer rings 1029A, 1029B do not interfere with any of the various sensing components described in the alternate embodiments above. Most of the sensing components are preferably located in a proximal portion 1007A (see FIG. 58A), although in alternative embodiments the sensing components may be located in a middle 1040A or distal portion 1005A as well.

Anchor features are cast onto the outer circumference of the tubular body 1001A, 1001B using a Shore A 30 Durometer silicone rubber compound. The specific compounds used for casting the anchoring and sealing features are RTV 430 silicone rubber resin and Beta 11-D 1 silicone catalyst solution, both manufactured by GE Silicones of Waterford, N.Y.

Certain advantages can be gained by using partial helical anchors 1045A, 1045B (as shown in FIGS. 58B and 58C) arranged in such a manner so that as the urethral apparatus is rotated through the urethra, each helical anchor does not come into contact with the urethral surface contacted by the proximally adjacent anchor, thereby eliminating trauma to the urethra while still providing for anchoring and easy insertion.

Any of the above described embodiments are compatible with the implementation of valves or other therapeutic, diagnostic, or urine-control elements. Embodiments without internal urine-flow restrictions, such as for the implementation of a stent or fluid conduit, allow urine flow freely with only a minimal pressure due to the small projected area as explained previously and illustrated in FIG. 57. In embodiments with relatively unrestricted fluid flow, the extent of surface contact (or total force) required for anchoring is substantially less than in embodiments with more restricted fluid flow. Thus, the surface and size modifications of urethral apparatus body can be purposefully made to make it easily insertable and retainable.

Further disclosure regarding anchoring is included in U.S. Pat. No. 5,971,967 issued Oct. 26, 1999.

It is to be understood, however, the even though numerous characteristics and advantages of the present invention have been set forth in the foregoing description, together with details of the structure and function of present invention, the sequence or order of the specific steps, or the actual compositions, environmental conditions, and the like experienced or sensed may vary somewhat. Furthermore, it will be appreciated that this disclosure is illustrative only and that changes may be made in detail, especially in matters of shape, size, arrangement of parts, or sequence of elements of the various aspects of the invention within the principles of the invention to the full extent indicated by the broad general meaning of the terms in which the appended claims are expressed.

I claim:

1. An apparatus for placement in a urethra comprising:

a tubular body sized for placement in the urethra, said tubular body having a proximal portion adapted for placement toward a bladder end and bladder neck end of the urethra and a distal portion opposite from said proximal portion;

a sensor component coupled to said tubular body and responsive to a urethral feature to provide a first indication of proper placement of said proximal portion at the bladder end and bladder neck end of the urethra whereby proper placement of said tubular body can be ascertained, wherein said sensor component comprises:

a fluid passageway extending through said tubular body and communicating with a proximal passageway opening in said proximal portion, said fluid passageway containing a fluid under a higher pressure when flow of the fluid from said proximal passageway opening is restricted and containing fluid under a lower pressure when flow of the fluid from said proximal opening is unrestricted; and a flow restrictor valve at said proximal passageway opening and adapted to prevent flow from said proximal passageway opening while said proximal passageway opening with within the urethra.

2. An apparatus for placement in a urethra comprising:

a tubular body sized for placement in the urethra, said tubular body having a proximal portion adapted for placement toward a bladder end and bladder neck end of the urethra and a distal portion opposite from said proximal portion, a sensor component coupled to said tubular body and responsive to a urethral feature to provide a first indication of proper placement of said proximal portion at the bladder end and bladder neck end of the urethra whereby proper placement of said tubular body can be ascertained; and a plurality of anchors extending outward from an exterior surface of said tubular body.

3. An apparatus for placement in a urethra comprising:

a tubular body sized for placement in the urethra, said tubular body having a proximal portion adapted for placement toward a bladder end and bladder neck end of the urethra and a distal portion opposite from said proximal portion;

a sensor component coupled to said tubular body and responsive to a urethral feature to provide a first indication of proper placement of said proximal portion at the bladder end and bladder neck end of the urethra whereby proper placement of said tubular body can be ascertained; and a plurality of anchors extending outward from an exterior surface of said tubular body wherein each of said plurality of anchors extends less than 360° around said exterior surface.

4. An apparatus for placement in a urethra comprising:

a tubular body sized for placement in the urethra, said tubular body having a proximal portion adapted for placement toward a bladder end and bladder neck end of the urethra and a distal portion opposite from said proximal portion;

a sensor component coupled to said tubular body and responsive to a urethral feature to provide a first indication of proper placement of said proximal portion at the bladder end and bladder neck end of the urethra whereby proper placement of said tubular body can be ascertained; and wherein said tubular body comprises a wall that defines a passageway extending from said proximal portion to said distal portion and further wherein said tubular body has a proximal opening located in said proximal portion and communicating with said passageway and a distal opening located in said distal portion and communicating with said passageway.

5. The invention of claim 4 further comprising a valve located in said passageway.

6. The invention of claim 4 wherein a distal portion of said passageway includes a recess for receiving an insertion tool.

7. An apparatus for placement in a urethra comprising:

a tubular body sized for placement in the urethra, said tubular body having a proximal portion adapted for placement toward a bladder end and bladder neck end of the urethra and a distal portion opposite from said proximal portion;

a sensor component coupled to said tubular body and responsive to a urethral feature to provide a first indication of proper placement of said proximal portion at the bladder end and bladder neck end of the urethra whereby proper placement of said tubular body can be ascertained; and wherein said tubular body defines a passageway extending from said proximal portion to said distal portion and further wherein said distal portion of said passageway includes a recess for receiving an insertion tool.

8. An apparatus for placement in a urethra comprising:

a tubular body sized for placement in the urethra, said tubular body having a proximal portion adapted for placement toward a bladder end and bladder neck end of the urethra and a distal portion opposite from said proximal portion;

a sensor component coupled to said tubular body and responsive to a urethral feature to provide a first indication of proper placement of said proximal portion at the bladder end and bladder neck end of the urethra whereby proper placement of said tubular body can be ascertained; and an anchor extending outward from an exterior surface of said tubular body.

9. An apparatus for placement in a urethra comprising:

a tubular body sized for placement in the urethra, said tubular body having a proximal portion adapted for placement toward a bladder end and bladder neck end of the urethra and a distal portion opposite from said proximal portion;

a sensor component coupled to said tubular body and responsive to a urethral feature to provide a first indication of proper placement of said proximal portion at the bladder end and bladder neck end of the urethra whereby proper placement of said tubular body can be ascertained; and an anchor extending outward from an exterior surface of said tubular body wherein said anchor extends less than 360° around said exterior surface.

* * * * *